(12) United States Patent
Prakash

(10) Patent No.: US 11,634,470 B2
(45) Date of Patent: Apr. 25, 2023

(54) INTEGRIN BINDING PEPTIDES AND USES THEREOF

(71) Applicants: Universiteit Twente, Enschede (NL); Jai Prakash, Enschede (NL)

(72) Inventor: Jai Prakash, Enschede (NL)

(73) Assignees: Jai Prakash, Enschede (NL); Universiteit Twente, Enschede (NL)

( * ) Notice: Subject to any disclaimer, the term of this patent is extended or adjusted under 35 U.S.C. 154(b) by 30 days.

(21) Appl. No.: 15/770,105

(22) PCT Filed: Oct. 21, 2016

(86) PCT No.: PCT/NL2016/050725
§ 371 (c)(1),
(2) Date: Apr. 20, 2018

(87) PCT Pub. No.: WO2017/069627
PCT Pub. Date: Apr. 27, 2017

(65) Prior Publication Data
US 2018/0312567 A1    Nov. 1, 2018

(30) Foreign Application Priority Data

Oct. 23, 2015 (EP) .................................... 15191256

(51) Int. Cl.
| | | |
|---|---|---|
| A61K 38/00 | (2006.01) |
| C07K 14/705 | (2006.01) |
| A61K 49/00 | (2006.01) |
| C07K 14/78 | (2006.01) |
| C07K 7/08 | (2006.01) |
| C07K 7/06 | (2006.01) |
| A61K 47/62 | (2017.01) |
| A61K 47/60 | (2017.01) |
| A61P 1/16 | (2006.01) |

(52) U.S. Cl.
CPC ........ *C07K 14/70546* (2013.01); *A61K 47/60* (2017.08); *A61K 47/62* (2017.08); *A61K 49/0045* (2013.01); *A61K 49/0056* (2013.01); *A61P 1/16* (2018.01); *C07K 7/06* (2013.01); *C07K 7/08* (2013.01); *C07K 14/78* (2013.01); *A61K 38/00* (2013.01); *C07K 2319/00* (2013.01)

(58) Field of Classification Search
CPC ........ A61K 38/00; A61K 47/60; A61K 47/62; A61K 49/0056; C07K 14/70546; C07K 14/78; C07K 2319/00; C07K 7/06; C07K 7/08
See application file for complete search history.

(56) References Cited

U.S. PATENT DOCUMENTS

| | | | |
|---|---|---|---|
| 4,589,881 A | 5/1986 | Pierschbacher et al. | |
| 5,536,814 A * | 7/1996 | Ruoslahti | C07K 14/7055 530/317 |
| 2010/0152063 A1 | 6/2010 | Cappuccilli et al. | |

FOREIGN PATENT DOCUMENTS

| | | | | |
|---|---|---|---|---|
| CN | 1305495 A | 7/2001 | | |
| WO | 95/14714 A1 | 6/1995 | | |
| WO | 9812226 A1 | 3/1998 | | |
| WO | 99/58139 A2 | 11/1999 | | |
| WO | 00/64480 A1 | 11/2000 | | |
| WO | 2013040142 A2 | 3/2013 | | |
| WO | 2013/067029 A2 | 5/2013 | | |
| WO | WO-2013142229 A1 * | 9/2013 | ............. | C07K 14/78 |
| WO | 2014/059213 A1 | 4/2014 | | |
| WO | WO-2014120891 A2 * | 8/2014 | ............. | C07K 14/78 |
| WO | 2017069627 A1 | 4/2017 | | |
| WO | 2013/185027 A2 | 11/2020 | | |

OTHER PUBLICATIONS

Sharma et al. Crystal structure of a heparin-and integrin-binding segment of human fibronectin. 1999. The EMBO Journal vol. 18 No. 6 pp. 1468-1479, 1999 (Year: 1999).*
Sequence listing of WO 2013/142229 (Year: 2013).*
Uniprot sequence (Year: 2020).*
Database Uniprot [Online], Jun. 24, 2015, "SubName: Full= Uncharacterized protein {ECO:0000313}", XP002755037, retrieved from EBI accession No. UniProt:A0A0E9Q1A5, Database accession No. A0A0E9Q1A5.
Aina et al., Canine malignant melanoma alpha-3 integrin binding peptides, Veterinary Immunology and Immunopathology, May 11, 2011, pp. 11-19, vol. 143, No. 1, Elsevier BV, Amsterdam, NL.
Database Uniprot [Online], Oct. 19, 2011, "SubName: Full= Hypothetical membrane protein {ECO:0000313}", XP002755038, retrieved from EBI accession No. Uniprot:G0ADR3, Database accession No. G0ADR3.
Database Uniprot [Online], Oct. 16, 2013, "SubName: Full=HAD super, subIIIB family protein {ECO:0000313}", XP002755039, retrieved from EBI accession No. Uniprot:27IPZ7, Database accession No. S71PZ7.
Navab et al., Prognostic gene-expression signature of carcinoma-associated fibroblasts in non-small cell lung cancer PNAS 2011, 108(17):7160-7165.
Protocol Multiwell Peptide Microarrays of JPT Technologies, Berlin Germany; Manual (20 pages).

(Continued)

*Primary Examiner* — Aradhana Sasan
*Assistant Examiner* — Mercy H Sabila
(74) *Attorney, Agent, or Firm* — TraskBritt

(57) ABSTRACT

The disclosure relates to integrin binding peptides, pharmaceutical compositions comprising the peptides and to uses thereof as therapeutic, diagnostic, imaging and targeting agents.

20 Claims, 18 Drawing Sheets

Specification includes a Sequence Listing.

(56) References Cited

OTHER PUBLICATIONS

Svendsen et al., "The a11β1 Integrin Has a Mechanistic Role in Control of Interstitial Fluid Pressure and Edema Formation in Inflammation" Arterioscler. Thromb. Vasc. Biol. 2009, 29(11):1864-1870.

Talior-Volodarsky et al., "a11 integrin stimulates myofibroblast differentiation in diabetic cardiomyopathy" Cardiovasc. Res. 2012, 96(2):265-275.

Tiger et al. "alpha11beta1 Integrin is a Receptor for Interstitial Collagens Involved in Cell Migration and Collagen Reorganization on Mesenchymal Nonmuscle Cells" Dev. Biol. 2001, 237(1):116-129).

Zhu et al., "Integrin_11 regulates IGF2 expression in fibroblasts to enhance tumorigenicity of human non-small-cell lung cancer cells" PNAS 2007, 104(28):11754-11759.

Atherton et al. "Solid-Phase Peptide Synthesis: A Practical Approach" vol. 265, No. 1,2 FEBS Letters Jun. 1990 (Abstract Only).

European Communication pursuant to Article 94(3) EPC for European Application No. 16794079, dated Sep. 28, 2020, 5 pages.

Japanese Notice of Reasons for Refusal for Japanese Application No. 2018-540362, dated Sep. 23, 2020, 8 pages (English translation only).

Merrifield "Solid Phase Peptide Synthesis. I the Synthesis of a Tetrapeptide" J. Am. Chem. Soc. 1963, 85, 14, 2149-2154, Publication Date:Jul. 1, 1963 https://doi.org/10.1021/ja00897a025 (Abstract Only).

Nagae et al. "Crystal structure of ?5?1 integrin ectodomain: Atomic details of the fibronectin receptor" J. Cell Biol. vol. 197 No. 1 131-140 www.jcb.org/cgi/doi/10.1083/jcb.201111077.

Neubauer et al. Selective Imaging of the Angiogenic Relevant Integrins a5β1 and avβ3, vol. 52, Issue 44, pp. 11656-11659 (2013) Wiley.

Rana et al. "A mixed-alpha,beta miniprotein stereochemically reprogrammed to high-binding affinity for acetylcholine" Biopolymers Nov. 2007; 87(4):231-43. https://doi.org/10.1002/bip.20829.

Rohrbacher et al. "Spontaneous head-to-tail cyclization of unprotected linear peptides with the KAHA ligation" Chem. Sci., 2015, 6, 4889-4896.

Tuin et al. "Structural and biological evaluation of some loloatin C analogues" Bioorganic & Medicinal Chemistry, vol. 17, Issue 17, 2009, pp. 6233-6240, ISSN 0968-0896, https://doi.org/10.1016/j.bmc.2009.07.049.

European Search Report and Search Opinion received for EP Application No. 16794079, dated Sep. 1, 2021, 4 pages.

Intention to Grant for European Application No. 16794079, dated Sep. 23, 2022, 6 pages.

\* cited by examiner

A

B

A

B

C

A

B

C

A

B

A

B

RYYRITY
AYYRITY - ↓
RAYRITY -
RYARITY - ↓↓↓
RYYAITY - ↓↓
RYYRATY - ↑
RYYRIAY - ↑ high unspecific binding
RYYRITA - ↓

A

B

A

B

1. AV3:      Ac-RYYRITY-OH
2. AV3-Cys:  Ac-RYYRITY-Cys-SH
3. AV3.1:    Ac-RAYRITY-OH
4. AV3.2:    Ac-RYYAITY-OH
5. AV3.3:    Ac-RYYRATY-OH
6. AV3.4:    Ac-RYYRIAY-OH
7. AV3-AXl:  Ac-RYYRITYGGGGLTEWLRWF-OH

A

B

INTEGRIN BINDING PEPTIDES AND USES THEREOF

CROSS-REFERENCE TO RELATED APPLICATIONS

This application is a national phase entry under 35 U.S.C. § 371 of International Patent Application PCT/NL2016/050725, filed Oct. 21, 2016, designating the United States of America and published in English as International Patent Publication WO 2017/069627 A1 on Apr. 27, 2017, which claims the benefit under Article 8 of the Patent Cooperation Treaty to European Patent Application Serial No. 15191256.5, filed Oct. 23, 2015.

TECHNICAL FIELD

The disclosure relates to the field of biochemistry and medicine. More specifically, the disclosure relates to the field of integrin binding peptides and to the treatment or prevention of fibrosis, a fibrosis-related disorder, an inflammatory disease or cancer.

BACKGROUND

Integrins are a family of glycoprotein transmembrane receptors that mediate cell-cell and cell-matrix interactions. Integrins are heterodimers having two different chains, the alpha and beta subunits. In mammals, eighteen α and eight β subunits have been described.

ITGA11, integrin alpha11 (α11), is an 1166 amino acid long (145 kDa) membrane-bound receptor. The ITGA11 receptor contains a large extracellular domain with 7 repeats of FG-GAP, a transmembrane region of 23 amino acids and a cytoplasmic tail of 24 amino acids. The cytoplasmic tail is highly conserved compared to other alpha chains. The α11 receptor is associated with a co-receptor integrin beta 1 (β1) and this dimeric receptor α11β1 binds to collagen type I. Integrin β1 is a co-partner with many integrin α receptors and is expressed by many tissues. However, the expression of ITGA11 has been shown to be limited to the mesenchymal non-muscle cells in areas of highly organized interstitial collagen networks (Tiger C. F., et al., Dev. Biol. 2001, 237(1):116-129).

ITGA11 is involved in cell attachment, migration and collagen reorganization on mesenchymal non-muscle cells. Non-muscle mesenchymal cells include mostly myofibroblasts that are found in fibrotic diseases such as liver fibrosis, kidney fibrosis, cardiac fibrosis, atherosclerosis and other fibrotic diseases. In addition, tumors stroma, non-malignant tumor component, is largely composed of myofibroblasts so called cancer-associated fibroblasts (CAFs). CAFs are the most prominent cell type in tumor stroma responsible for the pro-tumorigenic actions of stroma. In lung cancer (small cell lung cancer and non-small cell lung cancer), the expression of ITGA11 has been found upregulated in CAFs (Zhu C. Q., et al., PNAS 2007, 104(28):11754-11759; Navab R., et al., PNAS 2011, 108(17):7160-7165). The possible involvement of ITGA11 in other types of cancer is likely but not yet explored. Furthermore, high levels of ITGA11 expression have been shown in myofibroblasts present in diabetic cardiomyopathy and renal fibrosis (Talior-Volodarsky I., et al., Cardiovasc. Res. 2012, 96(2):265-275; Svendsen O. S., et al., Arterioscler. Thromb. Vasc. Biol. 2009, 29(11):1864-1870). It is likely that there are high expression levels of ITGA11 in other fibrotic diseases such as idiopathic pulmonary disease, liver fibrosis and skin fibrosis.

Integrin α5β1 is composed of subunits ITGA5 (integrin α5) and integrin β1. Several integrins bind to fibronectin, but α5β1 is selective for fibronectin since it requires both the $9^{th}$ and $10^{th}$ type II repeats of fibronectin (FNIII-9 and FNIII-10) for interaction. Expression of α5β1 integrin is mainly in the vasculature and connective tissue. Expression is significantly enhanced in tumor blood vessels, but also in tumor cells itself of many types of cancer, including colon, breast, ovarian, lung and brain tumors. It is further expressed to varying degrees in many cell types including fibroblasts, hematopoietic cell, immune cells, smooth muscle cells, and epithelial cells. High expression of α5β1 integrin has also been observed fibrotic tissue such as pulmonary fibrosis.

In tissues, normal fibroblasts are present in low population of only 4-5%. However, during fibrosis they proliferate and can occupy up to 80-90% of the organ mass. Myofibroblasts in the fibrotic tissue produce large amounts of extracellular matrix proteins that make the tissue scarred and non-functional. Inhibition of myofibroblasts can counteract these processes. In cancer, tumor stroma mainly consist of stromal myofibroblasts (or CAFs) and extracellular matrix can occupy up to 80% of the tumor in some cancer types such as breast cancer and pancreatic cancer. CAFs stimulate tumor growth and metastasis but also provide resistance to cancer cells against chemotherapies. Therefore, inhibition of CAF activity will be a highly interesting approach to block their pro-tumoral activities. In addition, CAFs are stable and largely expressed target and their detection using imaging techniques may lead to new diagnostic system for cancer. Specific delivery of imaging or therapeutic agents to myofibroblasts or CAFs would, therefore, be a highly interesting approach to develop novel diagnostic and therapeutic systems for cancer and fibrotic diseases.

BRIEF SUMMARY

It is an object of the present disclosure to provide integrin binding peptides, in particular ITGA5, ITGA11, α5β1 integrin and α11β1 binding peptides. Such peptides find wide use, for instance, in diagnosis and therapy of tumors and fibrotic diseases, for image-guided surgery, image-guided drug delivery, for targeted delivery of imaging or therapeutic agents.

The disclosure, therefore, provides an isolated or recombinant integrin alpha 11 (ITGA11) binding peptide having 5 to 25 amino acids and—comprising an amino acid sequence SGLTEWLRWFNS (SEQ ID NO:1) or a variant of the sequence, the variant:

consisting of 5-12 consecutive amino acids of the sequence, the 5-12 consecutive amino acids comprising at least the amino acids at positions 7-9 of the sequence, and having up to three substitutions of an amino acid of the 5-12 consecutive amino acids selected from amino acids at positions 1, 2, 4, 5, 6, 7, 8, 9, 11 and 12 of the sequence by another amino acid, or comprising an amino acid sequence SFATWTPNFERN (SEQ ID NO:2) or a variant of the sequence, the variant consisting of 5-12 consecutive amino acids of the sequence and having up to three substitutions of an amino acid by another amino acid.

In a further aspect, the disclosure provides an isolated or recombinant integrin alpha 5 (ITGA5) binding peptide having 6 to 25 amino acids and comprising an amino acid sequence TTVRYYRITYGETGGN (SEQ ID NO:3) or comprising a variant of the amino acid sequence, the variant:

consisting of 6-16 consecutive amino acids of the sequence, the 6-16 consecutive amino acids comprising at least the amino acids at positions 5-10 of the sequence, and having up to three substitutions of an amino acid of the 6-16 consecutive amino acids selected from amino acids at positions 1, 2, 3, 4, 5, 7, 8, 10, 11, 12, 13, 14, 15 and 16 of the sequence by another amino acid.

In a still further aspect, the disclosure provides a multimeric peptide comprising at least two peptides according to the disclosure, preferably a dimeric peptide comprising two peptides according to the disclosure.

In a still further aspect, the disclosure provides a compound comprising a peptide or multimeric peptide according to the disclosure. A preferred compound preferably comprises at least one further moiety, such as a label, a linker, a N- or C-terminal modification or an internal modification. The compound preferably comprises the peptide or multimeric peptide coupled to or encapsulated into a carrier selected from the group consisting of nanoparticles, microparticles, nanocapsules, nanocomplexes, polyplexes, carbon nanotubes, quantum dots, microcapsules, liposomes, microspheres, hydrogels, polymers, micelles, dendrimers, lipid complexes, serum albumin, antibodies, antibody fragments, cyclodextrins and dextran.

In a still further aspect, the disclosure provides a nucleic acid molecule comprising a nucleic acid sequence encoding a peptide according to the disclosure, a vector comprising a nucleic acid molecule according to the disclosure, and a recombinant host cell comprising a nucleic acid molecule and/or a vector according to the disclosure.

In a still further aspect, the disclosure provides a pharmaceutical composition comprising a peptide, a multimeric peptide, a compound or a nucleic acid molecule according to the disclosure, and at least one pharmaceutically acceptable carrier, diluent and/or excipient.

In a still further aspect, the disclosure provides a peptide, a multimeric peptide or nucleic acid molecule according to the disclosure for use as a therapeutic, prophylactic or diagnostic agent. The agent is preferably for use in the treatment or prevention of fibrosis or a fibrosis related disorder, an inflammatory disease or cancer.

In a still further aspect, the disclosure provides a use of a peptide or multimeric peptide according to the disclosure as an imaging or targeting agent.

In a still further aspect, the disclosure provides a method of imaging a tissue expressing integrin alpha 5 (ITGA5) or integrin alpha 11 (ITGA11), preferably expressing α5β1 or α11β1 integrin, by contacting the tissue with a peptide or multimeric peptide according to the disclosure.

In a still further aspect, the disclosure provides a method for the treatment of a subject suffering from fibrosis or a fibrosis related disorder, an inflammatory disease or cancer comprising administering to the subject a therapeutically effective amount of a peptide, multimeric peptide, nucleic acid molecule or a pharmaceutical composition according to the disclosure.

In a still further aspect, the disclosure provides a method for the preparation of a peptide according to the disclosure, the method comprising:

providing a nucleic acid molecule comprising a nucleic acid sequence encoding a peptide according to the disclosure;

transforming a host cell with the nucleic acid molecule;

culturing the host cell under conditions that allow expression of the peptide;

harvesting the peptide from the cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A, ITGA11 in human liver cirrhosis; FIG. 2B, ITGA11 in pancreatic cancer; FIG. 2C, ITGA11 in human kidney fibrosis. Images in FIGS. 2A and 2B show immunofluorescent staining of ITGA11 (green color) and a-SMA (red color) and their merge (yellow color). FIG. 2C shows the immunofluorescent staining of ITGA11 (red color) and a-SMA (green color) and their merge (orange-yellow color). These images show that ITGA11 is strongly expressed in fibrotic regions of all pathological conditions, which is co-localized with fibroblast marker a-SMA, shown with orange-yellow color in merge images.

(1. SEQ ID NO:8, 2. SEQ ID NO: 11, 3. SEQ ID NO:62, 4. SEQ ID NO:63, 5. SEQ ID NO: 64, 6. SEQ ID NO:76, and 7. SEQ ID NO:68.)

Figure 16:
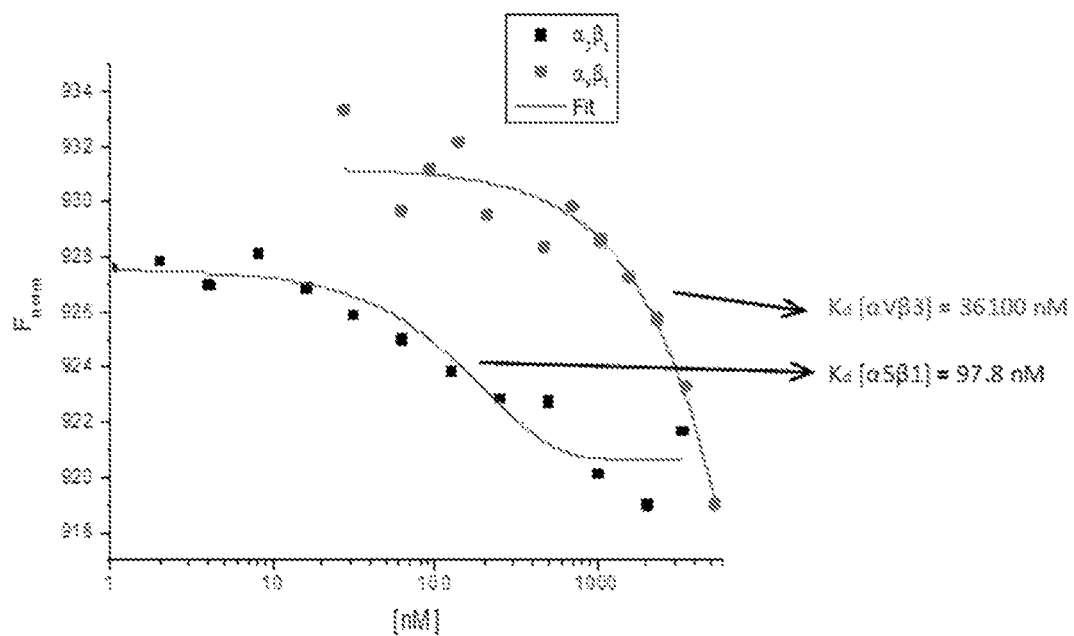
Figure 16:
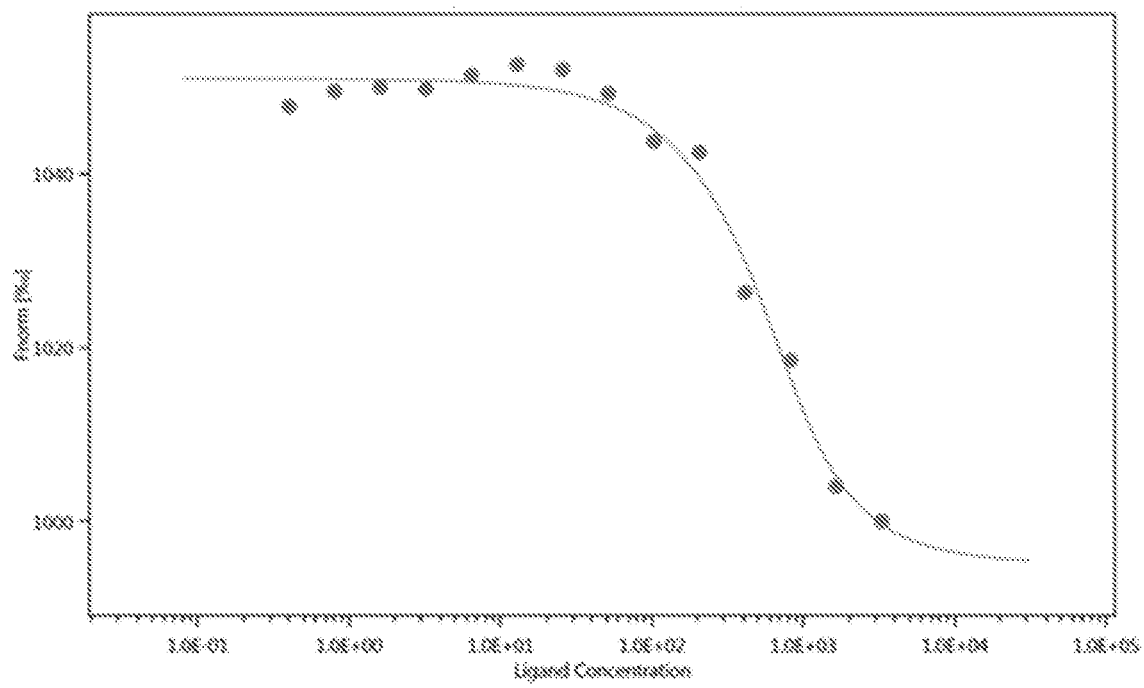

FIG. 16: Specificity of peptides AV3 and AXI-I. Fluorescent labeled peptides (AV3-PEG(6)-5FAM (Panel A) and AXI-I-PEG(6)-FITC (Panel B)) were examined for their binding affinities against α5β1 and α11β1 receptors, respectively.

Figure 17:
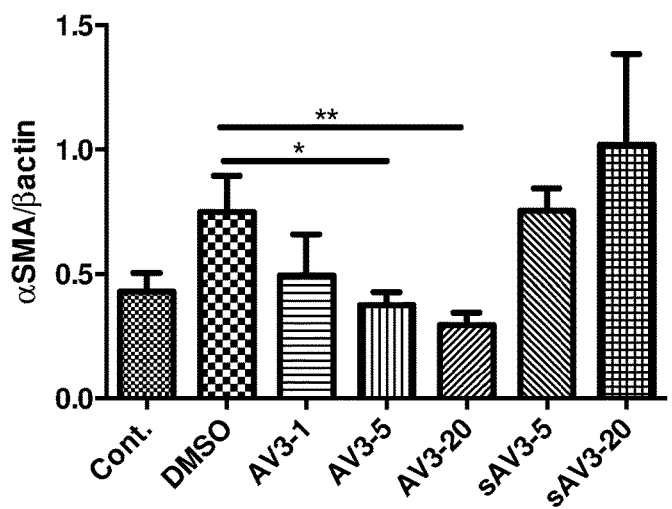

FIG. 17: Concentration response effect of AV3 peptide on the activation of human dermal fibroblasts.

Figure 18:
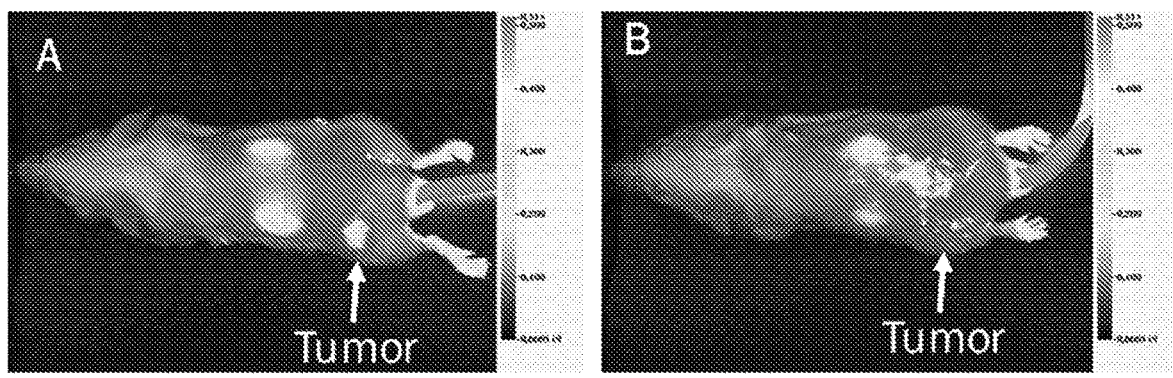

FIG. 18: Tumor imaging using AV3 peptide. Optical images showing the distribution of AV3 peptide labeled with 800CW dye (AV3-800CW). Human pancreatic tumor cells (Panc-1) combined with human pancreatic stellate cells (PSC) were co-injected into the flank of SCID mice and allowed to grow to a size of about 200 mm$^3$. AV3-800CW (1 nmol) was injected intravenously alone (Panel A) or with (Panel B) 50-fold excess of unlabeled AV3 in tumor-bearing mice. Images were captured using Pearl imager (LICOR).

DETAILED DESCRIPTION

It was found that ITGA11 is expressed in liver fibrosis and cirrhosis and pancreatic cancer and that ITGA11 expression in stellate cells is increased after activation with TGFβ1 and in CCl-4 induced liver fibrosis. It was further found that peptides having the sequence SGLTEWLRWFNS (SEQ ID NO:1) or SFATWTPNFERN (SEQ ID NO:2) and variants thereof bind with high affinity to ITGA11. It was also found that shorter variants of peptide SGLTEWLRWFNS (SEQ ID NO:1) having at least 5 consecutive amino acids of this sequence maintain binding capacity or even have increased binding capacity. Such ATGA11 binding peptide according to the disclosure has the advantage that it binds to the a subunit (α1) of integrin but not to β1, the latter of which is present in many integrins. An ATGA11 binding peptide according to the disclosure is, therefore, highly specific for α11β1 integrin. Since ITGA11 is highly expressed by myofibroblasts in tumors and fibrotic diseases, targeting ITGA11 using a ITGA11 binding peptide according to the disclosure is an optimal way to target tumor cells and fibrotic tissue cells.

Figure 8:
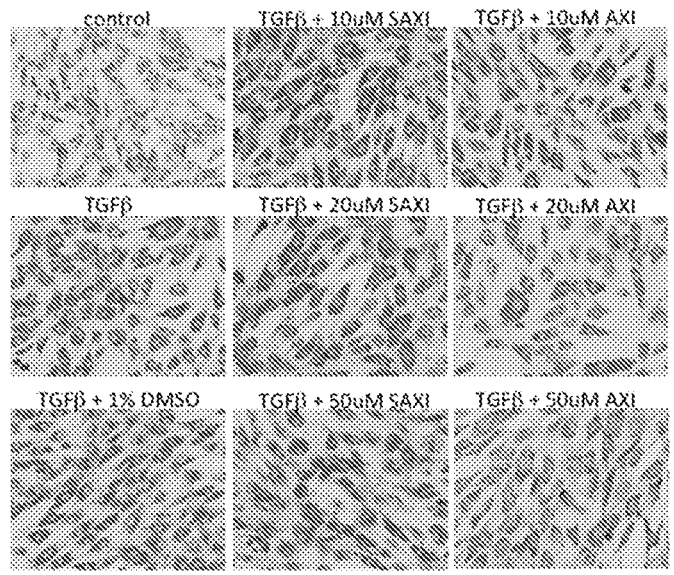
FIG. 8: Effect of AXI-I on activation of LX2 cells in vitro (Panel A) and in vivo in CCl4-induced liver fibrosis model in mice (Panels B and C). Panel A: Treatment with AXI-I inhibited the expression of collagen-I at increasing concentrations in the TGFβ-activated LX2 cells while scrambled peptide (SAXI) remained inactive. Panels B and C: In a CCl4-induced liver fibrosis model, treatment with AXI-I (200 ug/kg/d) i.p. injection led to reduction of fibrogenesis, as indicated by the decrease of gene expression of ITGA5 and ITGA11 (Panel B), markers of myofibroblasts and protein expression of collagen-I and III in livers compared to vehicle control (Panel C). *p<0.05 mean+SEM.
Figure 8:
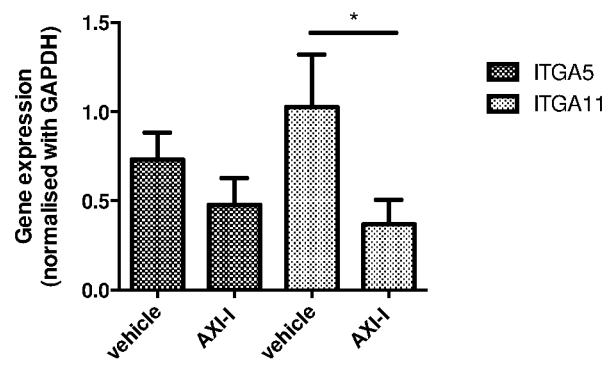
Figure 8:
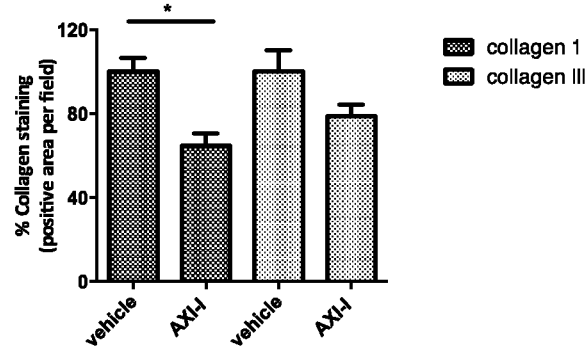

ITGA11 binding peptides of the disclosure were further found to have anti-fibrotic effects. As shown in the Examples, peptide AXI-I (SGLTEWLRWFNS (SEQ ID NO:1)) was shown to inhibit activation of LX2 cells as shown by reduced collagen expression after activation with TGFβ (FIG. 8, Panel A). In addition, this peptide was shown to reduce fibrogenesis, as demonstrated in a CCl4-induced liver fibrosis model by the decrease of gene expression of ITGA5 and ITGA11, markers of myofibroblasts, and decrease in protein expression of collagen-I and III in livers (FIG. 8, Panel B).

Accordingly, in a first aspect, the disclosure provides an isolated or recombinant integrin alpha 11 (ITGA11) binding peptide having 5 to 25 amino acids and comprising an amino acid sequence SGLTEWLRWFNS (SEQ ID NO:1) or a variant of the sequence, the variant:

consisting of 5-12 consecutive amino acids of the sequence, the 5-12 consecutive amino acids comprising at least the amino acids at positions 7-9 of the sequence, and having up to three substitutions of an amino acid of the 5-12 consecutive amino acids selected from amino acids at positions 1, 2, 4, 5, 6, 7, 8, 9, 11 and 12 of the sequence by another amino acid.

The peptide preferably does not consist of the sequence MSLRWFNSGSVRPATTILFP (SEQ ID NO:4).

A variant of the sequence SGLTEWLRWFNS (SEQ ID NO:1) has 5-12 consecutive amino acids of the sequence. Preferably, the variant has 6-12 consecutive amino acids of the sequence, more preferably 7-12 consecutive amino acids of the sequence, more preferably 8-12 consecutive amino acids of the sequence, more preferably 9-12 consecutive amino acids of the sequence, more preferably 10-12 consecutive amino acids of the sequence, such as 10, 11 or 12 consecutive amino acids of the sequence. A particularly preferred ITGA11 binding peptide consists of 5-12, preferably 6-12, such as 7-12, 8-12, 9-12, 10-12, 11-12 or 12, consecutive amino acids of the sequence SGLTEWLRWFNS (SEQ ID NO:1).

A variant of the sequence SGLTEWLRWFNS (SEQ ID NO:1) further comprises at least the amino acids at positions 7-9 of the sequence. Thus, the variant comprises at least the amino acid sequence LRW, optionally having one to three substitutions as defined herein, preferably one or two amino acids substitutions as defined herein, more preferably one amino acid substitutions as defined herein. Preferably, the variant comprises at least the amino acids at positions 6-9 of the sequence, i.e., the variant comprises at least the amino acid sequence WLRW (residues 4-8 of SEQ ID NO:24), optionally having one to three substitutions as defined herein, preferably one or two amino acids substitutions as defined herein, more preferably one amino acid substitutions as defined herein. In one embodiment, the variant comprises at least the sequence WLRW (residues 4-8 of SEQ ID NO:24).

A variant of the sequence SGLTEWLRWFNS (SEQ ID NO:1) further has up to three substitutions of an amino acid of the 5-12 consecutive amino acids by another amino acid. Up to three substitutions are selected from amino acids at positions 1, 2, 4, 5, 6, 7, 8, 9, 11 and 12 of the sequence SGLTEWLRWFNS (SEQ ID NO:1). Preferably, a variant of sequence SGLTEWLRWFNS (SEQ ID NO:1) as defined herein has no amino acid substitutions, or one or two of the amino acid substitutions, more preferably no amino acid substitutions or one of the amino acid substitutions. Further, preferably at most 25% of the amino acids of the variant of the sequence SGLTEWLRWFNS (SEQ ID NO:1) according to the disclosure has been substituted by another amino acid. In a further preferred embodiment, at most 20% of the amino acids of the variant of the sequence SGLTEWLRWFNS (SEQ ID NO:1) according to the disclosure has been substituted by another amino acid. In a further preferred embodiment, at most 150% of the amino acids of the variant of the sequence SGLTEWLRWFNS (SEQ ID NO:1) according to the disclosure has been substituted by another amino acid. In a further preferred embodiment, at most 10% of the amino acids of the variant of the sequence SGLTEWLRWFNS (SEQ ID NO:1) according to the disclosure has been substituted by another amino acid.

The variant of sequence SGLTEWLRWFNS (SEQ ID NO:1) having at least one amino acid substitution in the sequence preferably comprises up to three, more preferably one or two, conservative amino acids substitutions, substitutions with alanine or substitution with a corresponding non-natural amino acid. In a particularly preferred embodiment, the variant has one of the amino acid substitutions or no amino acid substitutions. More preferably, the variant of sequence SGLTEWLRWFNS (SEQ ID NO:1) having at least one amino acid substitution in the sequence preferably comprises up to three, more preferably one or two, more preferably one of the following amino acids substitutions:

serine at position 1 and/or at position 12 of the sequence SGLTEWLRWFNS (SEQ ID NO:1) is replaced by an amino acid selected from the group consisting of threonine, asparagine, glutamine, alanine, valine, isoleucine and leucine or by a corresponding non-natural amino acid, and/or glycine at position 2 of the sequence SGLTEWLRWFNS (SEQ ID NO:1) is replaced by an amino acid selected from the group consisting of proline, alanine, cysteine, serine, threonine, asparagine, aspartic acid and alanine or by a corresponding non-natural amino acid, and/or threonine at position 4 of the sequence SGLTEWLRWFNS (SEQ ID NO:1) is replaced by an amino acid selected from the group consisting of serine, asparagine, glutamine, alanine, valine, isoleucine and leucine or by a corresponding non-natural amino acid, and/or glutamic acid at position 5 of the sequence SGLTEWLRWFNS (SEQ ID NO:1) is replaced by an amino acid selected from the group consisting of aspartic acid, alanine, valine, isoleucine and leucine or by a corresponding non-natural amino acid, and/or tryptophan at position 6 and/or at position 9 of the sequence SGLTEWLRWFNS (SEQ ID NO:1) is replaced by an amino acid selected from the group consisting of alanine, valine, isoleucine, leucine, methionine, phenylalanine and tyrosine or by a corresponding non-natural amino acid, and/or leucine at position 7 of the sequence SGLTEWLRWFNS (SEQ ID NO:1) is replaced by an amino acid selected from the group consisting of arginine, lysine, histidine, alanine, valine and isoleucine or by a corresponding non-natural amino acid, and/or arginine at position 8 of the sequence SGLTEWLRWFNS (SEQ ID NO:1) is replaced by an amino acid selected from the group consisting of lysine, histidine, alanine, valine, isoleucine and leucine or by a corresponding non-natural amino acid, and/or asparagine at position 11 of the sequence SGLTEWLRWFNS (SEQ ID NO:1) is replaced by an amino acid selected from the group consisting of proline, alanine, cysteine, glycine, serine, threonine, aspartic acid and alanine or by a corresponding non-natural amino acid.

More preferably, the variant of sequence SGLTEWLRWFNS (SEQ ID NO:1) having at least one amino acid substitution in the sequence preferably comprises up to three, more preferably one or two, of the following amino acids substitutions:

serine at position 1 and/or at position 12 of the sequence SGLTEWLRWFNS (SEQ ID NO:1) is replaced by an amino acid selected from the group consisting of threonine, asparagine, glutamine and alanine or by a corresponding non-natural amino acid, and/or glycine at position 2 of the sequence SGLTEWLRWFNS (SEQ ID NO:1) is replaced by an amino acid selected from the group consisting of proline, alanine, cysteine, serine, threonine, asparagine and aspartic acid or by a corresponding non-natural amino acid, and/or threonine at position 4 of the sequence SGLTEWLRWFNS (SEQ ID NO:1) is replaced by an amino acid selected from the group consisting of serine, asparagine, glutamine and alanine or by a corresponding non-natural amino acid, and/or glutamic acid at position 5 of the sequence SGLTEWLRWFNS (SEQ ID NO:1) is replaced by an amino acid selected from the group consisting of aspartic acid and alanine or by a corresponding non-natural amino acid, and/or tryptophan at position 6 and/or at position 9 of the
   sequence SGLTEWLRWFNS (SEQ ID NO:1) is
   replaced by an amino acid selected from the group
   consisting of alanine, phenylalanine and tyrosine or by
   a corresponding non-natural amino acid, and/or
leucine at position 7 of the sequence SGLTEWLRWFNS
   (SEQ ID NO:1) is replaced by an amino acid selected
   from the group consisting of alanine, valine, isoleucine
   and methionine or by a corresponding non-natural
   amino acid, and/or
arginine at position 8 of the sequence SGLTEWLRWFNS
   (SEQ ID NO:1) is replaced by an amino acid selected
   from the group consisting of lysine, histidine and
   alanine or by a corresponding non-natural amino acid,
   and/or
asparagine at position 11 of the sequence SGLTEW-
   LRWFNS (SEQ ID NO:1) is replaced by an amino acid
   selected from the group consisting of threonine, serine,
   glutamine and alanine or by a corresponding non-
   natural amino acid.

More preferably, the variant of sequence SGLTEW-
LRWFNS (SEQ ID NO:1) having at least one amino acid
substitution in the sequence preferably comprises up to
three, more preferably one or two, of the following amino
acids substitutions:

serine at position 1 and/or at position 12 of the sequence
   SGLTEWLRWFNS (SEQ ID NO:1) is replaced by an
   amino acid selected from the group consisting of threo-
   nine, asparagine, glutamine and alanine, and/or
glycine at position 2 of the sequence SGLTEWLRWFNS
   (SEQ ID NO:1) is replaced by an amino acid selected
   from the group consisting of proline, alanine, cysteine,
   serine, threonine, asparagine and aspartic acid, and/or
threonine at position 4 of the sequence SGLTEW-
   LRWFNS (SEQ ID NO:1) is replaced by an amino acid
   selected from the group consisting of serine, aspara-
   gine, glutamine and alanine, and/or
glutamic acid at position 5 of the sequence SGLTEW-
   LRWFNS (SEQ ID NO:1) is replaced by an amino acid
   selected from the group consisting of aspartic acid and
   alanine, and/or
tryptophan at position 6 and/or at position 9 of the
   sequence SGLTEWLRWFNS (SEQ ID NO:1) is
   replaced by an amino acid selected from the group
   consisting of alanine, phenylalanine and tyrosine, and/
   or
leucine at position 7 of the sequence SGLTEWLRWFNS
   (SEQ ID NO:1) is replaced by an amino acid selected
   from the group consisting of alanine, valine, isoleucine
   and methionine, and/or
arginine at position 8 of the sequence SGLTEWLRWFNS
   (SEQ ID NO:1) is replaced by an amino acid selected
   from the group consisting of lysine, histidine and
   alanine, and/or
asparagine at position 11 of the sequence SGLTEW-
   LRWFNS (SEQ ID NO:1) is replaced by an amino acid
   selected from the group consisting of threonine, serine,
   glutamine and alanine.

In a preferred embodiment, one, two or three amino acid
substitutions in a variant of sequence SGLTEWLRWFNS
(SEQ ID NO:1), preferably one or two substitutions, more
preferably one substitution, are of amino acid at positions 1,
2, 4, 5, 6, 7, 8, 9, 11 and 12 of the sequence SGLTEW-
LRWFNS (SEQ ID NO:1) with the amino acid alanine.

A variant of the sequence SGLTEWLRWFNS (SEQ ID
NO:1) peptide according to the disclosure preferably con-
sists of all 12 amino acids of the amino acid sequence
SGLTEWLRWFNS (SEQ ID NO:1) with up to three sub-
stitutions, preferably up to two substitution, preferably one
substitution, of amino acids selected from amino acids at
position 1, 2, 4, 5, 6, 7, 8, 9, 11 and 12 of the sequence by
another amino acid as defined herein.

A preferred ITGA11 binding peptide according to the
disclosure comprises an amino acid sequence SGLTEW-
LRWFNS (SEQ ID NO:1) or a variant of the sequence as
defined herein. A particularly preferred ITGA11 binding
peptide of the disclosure consists of the sequence SGLTEW-
LRWFNS (SEQ ID NO:1) or consists of a variant of the
sequence as defined herein.

A particularly preferred variant of the sequence
SGLTEWLRWFNS (SEQ ID NO:1) has a sequence selected
from the sequences in Table 1. A particularly preferred
ITGA11 binding peptide according to the disclosure consists
of a sequence selected from the sequences of Table 1.

In a particularly preferred embodiment is provided an
isolated or recombinant integrin alpha 11 (ITGA11) binding
peptide having 6-12 amino acids and comprising an amino
acid sequence SGLTEWLRWFNS (SEQ ID NO:1) or a
variant of the sequence, the variant:

consisting of 6-12 consecutive amino acids of the
   sequence, the 6-12 consecutive amino acids comprising
   at least the amino acids at positions 6-9 of the sequence,
   and
optionally having up to three substitutions, preferably one
   or two substitutions, more preferably one substitution,
   of an amino acid of the 6-12 consecutive amino acids
   whereby the amino acid substitutions are selected from
   the group consisting of:
   substitution of serine at position 1 or at position 12 of
      the sequence SGLTEWLRWFNS (SEQ ID NO:1) by
      an amino acid selected from the group consisting of
      threonine, asparagine, glutamine and alanine, pref-
      erably alanine,
   substitution of glycine at position 2 of the sequence
      SGLTEWLRWFNS (SEQ ID NO:1) by an amino
      acid selected from the group consisting of proline,
      alanine, cysteine, serine, threonine, asparagine and
      aspartic acid, preferably alanine,
   substitution of threonine at position 4 of the sequence
      SGLTEWLRWFNS (SEQ ID NO:1) by an amino
      acid selected from the group consisting of serine,
      asparagine, glutamine and alanine, preferably ala-
      nine,
   substitution of glutamic acid at position 5 of the
      sequence SGLTEWLRWFNS (SEQ ID NO:1) by an
      amino acid selected from the group consisting of
      aspartic acid and alanine, preferably alanine,
   substitution of tryptophan at position 6 or at position 9
      of the sequence SGLTEWLRWFNS (SEQ ID NO:1)
      by an amino acid selected from the group consisting
      of alanine, phenylalanine and tyrosine, preferably
      alanine,
   substitution of leucine at position 7 of the sequence
      SGLTEWLRWFNS (SEQ ID NO:1) by an amino
      acid selected from the group consisting of alanine,
      valine, isoleucine and methionine, preferably ala-
      nine,
   substitution of arginine at position 8 of the sequence
      SGLTEWLRWFNS (SEQ ID NO:1) by an amino
      acid selected from the group consisting of lysine,
      histidine and alanine, preferably alanine, and
   substitution of asparagine at position 11 of the sequence
      SGLTEWLRWFNS (SEQ ID NO:1) by an amino acid selected from the group consisting of threonine, serine, glutamine and alanine, preferably alanine.

In a further aspect, the disclosure provides an isolated or recombinant integrin alpha 11 (ITGA11) binding peptide having 5 to 25 amino acids and comprising an amino acid sequence SFATWTPNFERN (SEQ ID NO:2) or a variant of the sequence, the variant consisting of 5-12 consecutive amino acids of the sequence and having up to three substitutions of an amino acid by another amino acid.

A variant of the sequence SFATWTPNFERN (SEQ ID NO:2) has 5-12 consecutive amino acids of the sequence. Preferably, the variant has 6-12 consecutive amino acids of the sequence, more preferably 7-12 consecutive amino acids of the sequence, more preferably 8-12 consecutive amino acids of the sequence, more preferably 9-12 consecutive amino acids of the sequence, more preferably 10-12 consecutive amino acids of the sequence, such as 10, 11 or 12 consecutive amino acids of the sequence. A particularly preferred ITGA11 binding peptide consists of 5-12, preferably 6-12, such as 7-12, 8-12, 9-12, 10-12, 11-12 or 12, consecutive amino acids of the sequence SFATWTPNFERN (SEQ ID NO:2). In one embodiment, an ITGA11 binding peptide consists of the sequence SFATWTPNFERN (SEQ ID NO:2).

A variant of the sequence SFATWTPNFERN (SEQ ID NO:2) further has up to three substitutions of an amino acid of the 5-12 consecutive amino acids by another amino acid. Preferably, a variant of sequence SFATWTPNFERN (SEQ ID NO:2) as defined herein has no amino acid substitutions, or one or two of the amino acid substitutions, more preferably no amino acid substitutions or one of the amino acid substitutions. Further, preferably at most 25% of the amino acids of the variant of the sequence SFATWTPNFERN (SEQ ID NO:2) according to the disclosure has been substituted by another amino acid. In a further preferred embodiment, at most 20% of the amino acids of the variant of the sequence SFATWTPNFERN (SEQ ID NO:2) according to the disclosure has been substituted by another amino acid. In a further preferred embodiment, at most 150% of the amino acids of the variant of the sequence SFATWTPNFERN (SEQ ID NO:2) according to the disclosure has been substituted by another amino acid. In a further preferred embodiment, at most 10% of the amino acids of the variant of the sequence SFATWTPNFERN (SEQ ID NO:2) according to the disclosure has been substituted by another amino acid.

The amino acid substitutions are preferably conservative amino acids substitutions, substitutions with alanine or substitutions with a corresponding non-natural amino acid. In a particularly preferred embodiment, the variant has one of the amino acid substitutions or no amino acid substitution.

More preferably, the variant of sequence SFATWTPNFERN (SEQ ID NO:2) having at least one amino acid substitution in the sequence preferably comprises up to three, more preferably one or two, more preferably one of the following amino acids substitutions:
  serine at position 1 of the sequence is replaced by an amino acid selected from the group consisting of threonine, asparagine, glutamine, alanine, valine, isoleucine and leucine or by a corresponding non-natural amino acid, and/or
  phenylalanine at position 2 and/or at position 9 of the sequence is replaced by an amino acid selected from the group consisting of alanine, valine, isoleucine, leucine, methionine, tyrosine and tryptophan or by a corresponding non-natural amino acid, and/or
  alanine at position 3 of the sequence is replaced by an amino acid selected from the group consisting of valine, isoleucine, leucine, methionine, phenylalanine, tyrosine and tryptophan or by a corresponding non-natural amino acid, and/or
  threonine at position 4 and/or at position 6 of the sequence is replaced by an amino acid selected from the group consisting of serine, asparagine, glutamine, alanine, valine, isoleucine and leucine or by a corresponding non-natural amino acid, and/or
  tryptophan at position 5 of the sequence is replaced by an amino acid selected from the group consisting of alanine, valine, isoleucine, leucine, methionine, phenylalanine and tyrosine or by a corresponding non-natural amino acid, and/or
  proline at position 7 of the sequence is replaced by an amino acid selected from the group consisting of alanine, cysteine, glycine, serine, threonine, asparagine and aspartic acid or by a corresponding non-natural amino acid, and/or
  asparagine at position 8 and/or at position 12 of the sequence is replaced by an amino acid selected from the group consisting of threonine, serine, glutamine, alanine, valine, isoleucine and leucine or by a corresponding non-natural amino acid, and/or
  glutamic acid at position 10 of the sequence is replaced by an amino acid selected from the group consisting of aspartic acid, alanine, valine, isoleucine and leucine or by a corresponding non-natural amino acid, and/or
  arginine at position 11 of the sequence is replaced by an amino acid selected from the group consisting of lysine, histidine, alanine, valine, isoleucine and leucine or by a corresponding non-natural amino acid.

More preferably, the variant of sequence SFATWTPNFERN (SEQ ID NO:2) having at least one amino acid substitution in the sequence preferably comprises up to three, more preferably one or two, more preferably one of the following amino acids substitutions:
  serine at position 1 of the sequence is replaced by an amino acid selected from the group consisting of threonine, asparagine, glutamine and alanine or by a corresponding non-natural amino acid, and/or
  phenylalanine at position 2 and/or at position 9 of the sequence is replaced by an amino acid selected from the group consisting of tyrosine, tryptophan and alanine or by a corresponding non-natural amino acid, and/or
  alanine at position 3 of the sequence is replaced by an amino acid selected from the group consisting of valine, isoleucine, leucine and methionine or a corresponding non-natural amino acid, and/or
  threonine at position 4 and/or at position 6 of the sequence is replaced by an amino acid selected from the group consisting of serine, asparagine, glutamine and alanine or by a corresponding non-natural amino acid, and/or
  tryptophan at position 5 of the sequence is replaced by an amino acid selected from the group consisting of alanine, phenylalanine and tyrosine or by a corresponding non-natural amino acid, and/or
  asparagine at position 8 and/or at position 12 of the sequence is replaced by an amino acid selected from the group consisting of threonine, serine, glutamine and alanine or by a corresponding non-natural amino acid, and/or
  glutamic acid at position 10 of the sequence is replaced by an amino acid selected from the group consisting of aspartic acid and alanine or by a corresponding non-natural amino acid, and/or arginine at position 11 of the sequence is replaced by an amino acid selected from the group consisting of lysine, histidine and alanine or by a corresponding non-natural amino acid.

More preferably, the variant of sequence SFATWTPN-FERN (SEQ ID NO:2) having at least one amino acid substitution in the sequence preferably comprises up to three, more preferably one or two, more preferably one of the following amino acids substitutions:

serine at position 1 of the sequence is replaced by an amino acid selected from the group consisting of threonine, asparagine, glutamine and alanine, and/or phenylalanine at position 2 and/or at position 9 of the sequence is replaced by an amino acid selected from the group consisting of tyrosine, tryptophan and alanine, and/or alanine at position 3 of the sequence is replaced by an amino acid selected from the group consisting of valine, isoleucine, leucine and methionine, and/or threonine at position 4 and/or at position 6 of the sequence is replaced by an amino acid selected from the group consisting of serine, asparagine, glutamine and alanine, and/or tryptophan at position 5 of the sequence is replaced by an amino acid selected from the group consisting of alanine, phenylalanine and tyrosine, and/or asparagine at position 8 and/or at position 12 of the sequence is replaced by an amino acid selected from the group consisting of threonine, serine, glutamine and alanine or by a corresponding non-natural amino acid, and/or glutamic acid at position 10 of the sequence is replaced by an amino acid selected from the group consisting of aspartic acid and alanine, and/or arginine at position 11 of the sequence is replaced by an amino acid selected from the group consisting of lysine, histidine and alanine.

In a preferred embodiment, one, two or three amino acid substitutions in a variant of sequence SFATWTPNFERN (SEQ ID NO:2), preferably one or two substitutions, more preferably one substitution, substitutions with the amino acid alanine.

A variant of the sequence SFATWTPNFERN (SEQ ID NO:2) peptide according to the disclosure preferably consists of all 12 amino acids of the amino acid sequence SGLTEWLRWFNS (SEQ ID NO:1) with up to three amino acid substitutions as defined herein, preferably up to two substitution as defined herein, more preferably one substitution as defined herein.

A preferred ITGA11 binding peptide of the disclosure comprises the sequence SFATWTPNFERN (SEQ ID NO:2) or comprises a variant of the sequence as defined herein. A particularly preferred ITGA11 binding peptide of the disclosure consists of the sequence SFATWTPNFERN (SEQ ID NO:2) or consists of a variant of the sequence as defined herein.

The present inventors further found that ITGA5 is expressed in pancreatic cancer, kidney fibrosis, skin fibroblasts and pancreatic stellate cells, where expression is enhanced following activation with TGFβ1. It was further found that peptides with overlapping sequences TTVRYYRITYGE (SEQ ID NO:7) and YYRITYGETGGN (SEQ ID NO:56) and variants thereof bind with high affinity to ITGA5. It was also found that shorter peptide variants of these sequences maintain binding capacity or even have increased binding capacity. Such ATGA5 binding peptide according to the disclosure has the advantage that it binds to the α subunit (α5) of integrin but not to β1, the latter of which is preffigursent in many integrins. An ATGA5 binding peptide according to the disclosure is, therefore, highly specific for α5β1 integrin.

Figure 14:
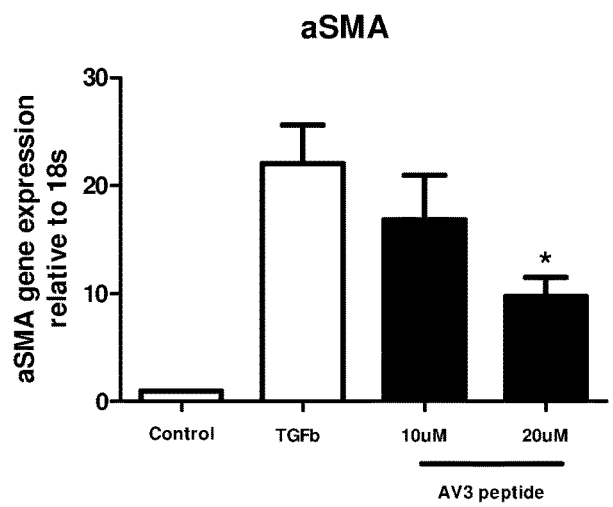
FIG. 14: Panel A, Anti-fibrotic effect of AV3 peptide. Panel B, AV3-cys peptide effect on PSC activation in vitro (20 μM concentration, 20× magnification). Panel A, Activation of PSCs with TGFβ led to activation of these cells as indicated by α-SMA expression. Treatment with AV3 peptide significantly inhibited the α-SMA expression at 20 μM. Panel B, Incubation of PSCs with TGFβ1 enhanced the expression of fibrotic markers such as α-SMA, Col-1a1 and vimentin, as shown with immunostainings. Treatment with AV3-cys peptide clearly inhibited the expression of these biomarkers. In contrast, scrambled AV3-cys did not show any inhibitory effects.
Figure 14:
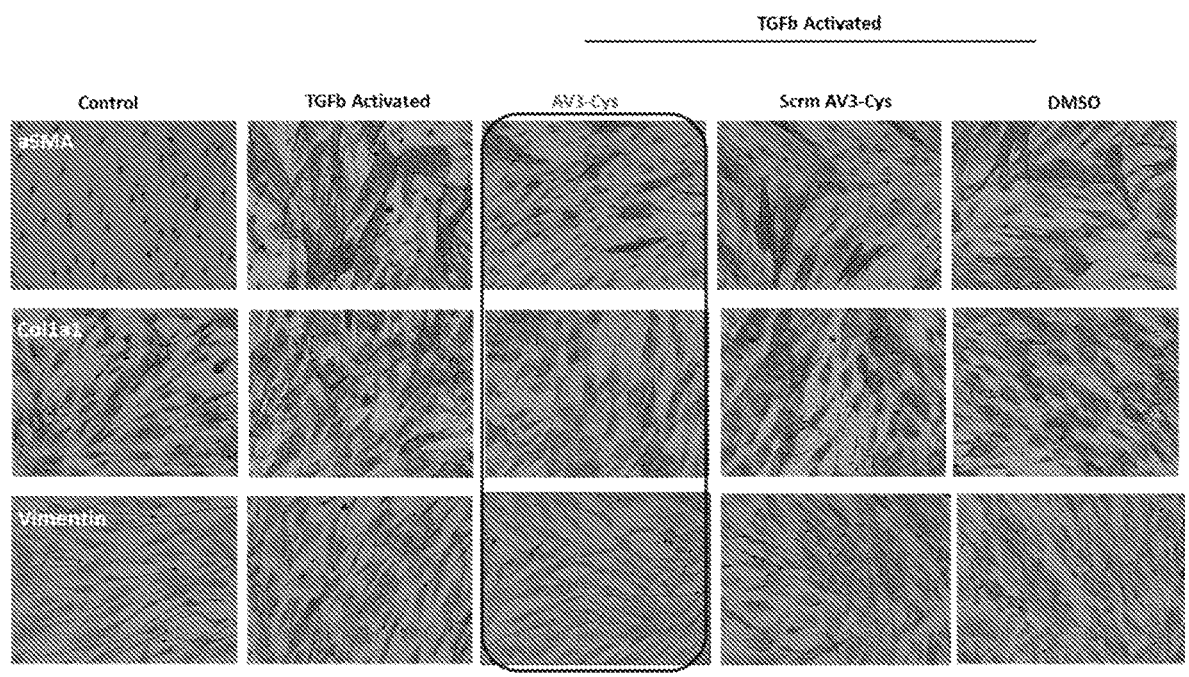
Figure 15:
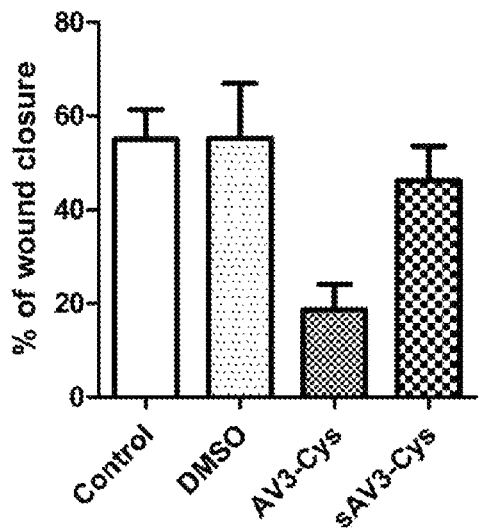
FIG. 15: Effect of peptides on migration of human fibroblasts. Human skin fibroblasts BJhtert were grown to full confluency and a scratch (wound) was made and effects of peptides were determined on the wound closure (migration of fibroblasts) after 24 hours. Panel A shows that AV3-cys significantly inhibited the migration of fibroblasts while its scrambled version did not show any effect. Panel B shows the effect of different peptides on the migration of the fibroblasts. Only AV3.3 showed about 30% reduction on migration while other versions showed slight or no effects.
Figure 15:
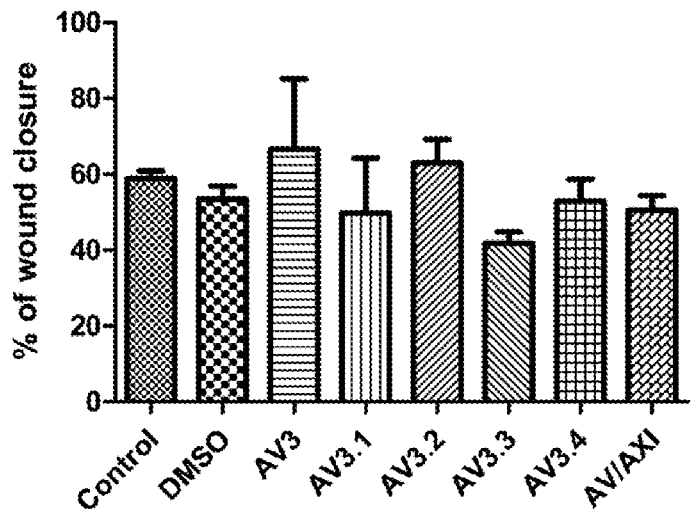

The ITGA5 binding peptides of the disclosure were further found to have anti-fibrotic effects. As shown in the Examples, peptide AV3 (RYYRITY (SEQ ID NO:8)) was shown to inhibit pancreatic stellate cell activation as shown by inhibition of αSMA expression after activation with TGFβ (FIG. 14, Panel A) and expression of fibrotic markers such as α-SMA, Col-1a1 and vimentin (FIG. 14, Panel B). In addition, IGTA5 binding peptides were shown to inhibit migration of human fibroblasts (FIG. 15).

In a further aspect, the disclosure therefor provides an isolated or recombinant integrin alpha 5 (ITGA5) binding peptide having 6 to 25 amino acids and comprising an amino acid sequence TTVRYYRITYGETGGN (SEQ ID NO:3) or comprising a variant of the amino acid sequence, the variant:

consisting of 6-16 consecutive amino acids of the sequence, the 6-16 consecutive amino acids comprising at least the amino acids at positions 5-10 of the sequence, and having up to three substitutions of an amino acid of the 6-16 consecutive amino acids selected from amino acids at positions 1, 2, 3, 4, 5, 7, 8, 10, 11, 12, 13, 14, 15 and 16 of the sequence by another amino acid.

A variant of the sequence TTVRYYRITYGETGGN (SEQ ID NO:3) has 6-16 consecutive amino acids of the sequence. Preferably, the variant has 7-16 consecutive amino acids of the sequence. In a further embodiment, the variant has 8-16, 9-16, 10-16, 11-16 or 12-16 consecutive amino acids of the sequence. A particularly preferred ITGA5 binding peptide consists of a variant having 6-16, preferably 7-16, consecutive amino acids of the sequence TTVRYYRITYGETGGN (SEQ ID NO:3), such as 6, 7, 8, 9, 10, 11, 12, 13, 14, 15 or 16, consecutive amino acids of the sequence TTVRYYRITYGETGGN (SEQ ID NO:3).

A variant of the sequence TTVRYYRITYGETGGN (SEQ ID NO:3) further comprises at least the amino acids at positions 5-10 of the sequence. Thus, the variant comprises at least the amino acid sequence YYRITY, optionally having up to three, preferably up to two, preferably up to one, amino acid substitutions as defined herein. Preferably, the variant comprises at least the amino acids at positions 4-10 of the sequence, i.e., the variant comprises at least the amino acid sequence RYYRITY, optionally having one to three substitutions as defined herein, more preferably one or two amino acids substitutions as defined herein, more preferably one amino acid substitutions as defined herein. In one embodiment, the variant comprises at least the sequence YYRITY, preferably the sequence RYYRITY (SEQ ID NO:8).

A variant of the sequence TTVRYYRITYGETGGN (SEQ ID NO:3) further has up to three substitutions of an amino acid of the 6-16 consecutive amino acids by another amino acid. Up to three substitutions are selected from amino acids at positions 1, 2, 3, 4, 5, 7, 8, 10, 11, 12, 13, 14, 15 and 16 of the sequence TTVRYYRITYGETGGN (SEQ ID NO:3). Further, preferably at most 25% of the amino acids of the variant of the sequence TTVRYYRITYGETGGN (SEQ ID NO:3) according to the disclosure has been substituted by another amino acid. In a further preferred embodiment, at most 20% of the amino acids of the variant of the sequence TTVRYYRITYGETGGN (SEQ ID NO:3) according to the disclosure has been substituted by another amino acid. In a further preferred embodiment, at most 150% of the amino acids of the variant of the sequence TTVRYYRITYGETGGN (SEQ ID NO:3) according to the disclosure has been substituted by another amino acid. In a further preferred embodiment, at most 10% of the amino acids of the variant of the sequence TTVRYYRITY-GETGGN (SEQ ID NO:3) according to the disclosure has been substituted by another amino acid. Preferably, a variant of sequence TTVRYYRITYGETGGN (SEQ ID NO:3) as defined herein has no amino acid substitutions, or one or two of the amino acid substitutions, more preferably no amino acid substitutions or one of the amino acid substitutions. One or two substitutions are preferably substitutions of one or both amino acids at position 5 and 8 of the sequence TTVRYYRITYGETGGN (SEQ ID NO:3).

The variant of sequence TTVRYYRITYGETGGN (SEQ ID NO:3) having at least one amino acid substitution in the sequence preferably comprises up to three, more preferably one or two, conservative amino acids substitutions, substitutions with alanine or substitution with a corresponding non-natural amino acid. In a particularly preferred embodiment, the variant has one of the amino acid substitutions or no amino acid substitutions. Up to three, preferably up to two, more preferably up to one, amino acid substitutions are preferably substitutions of the amino acids at positions 5-10 of the sequence.

More preferably, the variant of sequence TTVRYYRITY-GETGGN (SEQ ID NO:3), preferably of sequence RYYRITY (SEQ ID NO:8), having at least one amino acid substitution in the sequence preferably comprises up to three, more preferably one or two, more preferably one of the following amino acids substitutions:

arginine at position 4 and/or at position 7 of the sequence is replaced by an amino acid selected from the group consisting of lysine, histidine, alanine, valine, isoleucine and leucine or by a corresponding non-natural amino acid, and/or tyrosine at position 5 and/or at position 10 of the sequence is replaced by an amino acid selected from the group consisting of alanine, valine, isoleucine, leucine, methionine, phenylalanine and tryptophan or by a corresponding non-natural amino acid, and/or isoleucine at position 8 of the sequence is replaced by an amino acid selected from the group consisting of alanine, valine, leucine, methionine, phenylalanine, tyrosine and tryptophan or by a corresponding non-natural amino acid.

More preferably, the variant of sequence TTVRYYRITY-GETGGN (SEQ ID NO:3), preferably of sequence RYYRITY (SEQ ID NO:8), having at least one amino acid substitution in the sequence preferably comprises up to three, more preferably one or two, most preferably one, of the following amino acids substitutions:

arginine at position 4 and/or at position 7 of the sequence is replaced by an amino acid selected from the group consisting of lysine, histidine and alanine or by a corresponding non-natural amino acid, and/or tyrosine at position 5 and/or at position 10 of the sequence is replaced by an amino acid selected from the group consisting of alanine, phenylalanine and tryptophan or by a corresponding non-natural amino acid, and/or isoleucine at position 8 of the sequence is replaced by an amino acid selected from the group consisting of alanine, valine, leucine and methionine or by a corresponding non-natural amino acid.

More preferably, the variant of sequence TTVRYYRITY-GETGGN (SEQ ID NO:3), preferably of sequence RYYRITY (SEQ ID NO:8), having at least one amino acid substitution in the sequence preferably comprises up to three, more preferably one or two, of the following amino acids substitutions:

arginine at position 4 and/or at position 7 of the sequence is replaced by an amino acid selected from the group consisting of lysine, histidine and alanine, and/or tyrosine at position 5 and/or at position 10 of the sequence is replaced by an amino acid selected from the group consisting of alanine, phenylalanine and tryptophan, and/or isoleucine at position 8 of the sequence is replaced by an amino acid selected from the group consisting of alanine, valine, leucine and methionine.

In a preferred embodiment, one, two or three amino acid substitutions in a variant of sequence RYYRITY (SEQ ID NO:8), preferably one or two substitutions, more preferably one substitution, are of amino acid at positions 1, 2, 4, 5 or 7 of the sequence RYYRITY (SEQ ID NO:8) with the amino acid alanine.

In a preferred embodiment is provided an isolated or recombinant integrin alpha 5 (ITGA5) binding peptide having 6-16 amino acids and comprising an amino acid sequence TTVRYYRITYGETGGN (SEQ ID NO:3) or a variant of the sequence, the variant:

consisting of 6-16 consecutive amino acids of the sequence, the 6-16 consecutive amino acids comprising at least the amino acids at positions 5-10 of the sequence, and optionally having up to three substitutions, preferably one or two substitutions, more preferably one substitution, of an amino acid of the amino acids at positions 5-10 of the sequence whereby the amino acid substitutions are selected from the group consisting of:

arginine at position 4 of the sequence is replaced by an amino acid selected from the group consisting of lysine, histidine and alanine, preferably alanine, arginine at position 7 of the sequence is replaced by an amino acid selected from the group consisting of lysine, histidine and alanine, preferably alanine, tyrosine at position 5 of the sequence is replaced by an amino acid selected from the group consisting of alanine, phenylalanine and tryptophan, preferably alanine, tyrosine at position 10 of the sequence is replaced by an amino acid selected from the group consisting of alanine, phenylalanine and tryptophan, preferably alanine, and isoleucine at position 8 of the sequence is replaced by an amino acid selected from the group consisting of alanine, valine, leucine and methionine, preferably alanine.

In a further preferred embodiment is provided an isolated or recombinant integrin alpha 5 (ITGA5) binding peptide having 6-16 amino acids and comprising an amino acid sequence TTVRYYRITYGETGGN (SEQ ID NO:3) or a variant of the sequence, the variant:

consisting of 6-16 consecutive amino acids of the sequence, the 6-16 consecutive amino acids comprising at least the amino acids at positions 5-10 of the sequence, and optionally having one or two substitutions, more preferably one substitution, of an amino acid of the amino acids at positions 5-10 of the sequence whereby the amino acid substitutions are selected from the group consisting of:

tyrosine at position 5 of the sequence is replaced by an amino acid selected from the group consisting of alanine, phenylalanine and tryptophan, preferably alanine, isoleucine at position 8 of the sequence is replaced by an amino acid selected from the group consisting of alanine, valine, leucine and methionine, preferably alanine.

A particularly preferred variant of the sequence TTVRYYRITYGETGGN (SEQ ID NO:3) has a sequence selected from the sequences in Table 2. A particularly preferred ITGA5 binding peptide according to the disclosure consist of a sequence selected from the sequences of Table 2. The ITGA5 binding peptide, for instance, consists of an amino acid sequence selected from the group consisting of RYYRITY (SEQ ID NO:8), RYYRITYC (SEQ ID NO:11), TTVRYYRITYGE (SEQ ID NO:7) and YYRITYGETGGN (SEQ ID NO:56).

In amino acid sequences or variants thereof as defined herein amino acids are denoted by single-letter symbols. These single-letter symbols and three-letter symbols are well known to the person skilled in the art and have the following meaning: A (Ala) is alanine, C (Cys) is cysteine, D (Asp) is aspartic acid, E (Glu) is glutamic acid, F (Phe) is phenylalanine, G (Gly) is glycine, H (His) is histidine, I (Ile) is isoleucine, K (Lys) is lysine, L (Leu) is leucine, M (Met) is methionine, N (Asn) is asparagine, P (Pro) is proline, Q (Gln) is glutamine, R (Arg) is arginine, S (Ser) is serine, T (Thr) is threonine, V (Val) is valine, W (Trp) is tryptophan, Y (Tyr) is tyrosine.

A "conservative amino acid substitution" as used herein is a substitution in which an amino acid is substituted by another amino acid having a side chain with similar chemical properties, in particular charge or hydrophobicity. A conservative amino acid substitution typically does not substantially change the ATGA5 or ATGA11 binding properties of the peptide. The following five groups each list amino acids that are conservative substitutions for one another:

1) serine, threonine asparagine, glutamine;
2) aspartic acid, glutamic acid;
3) histidine, arginine, lysine;
4) isoleucine, leucine, methionine, alanine, valine, and
5) phenylalanine, tyrosine, tryptophan.

As used herein, a "corresponding non-natural amino acid" refers to a non-natural amino acid that is a derivative of the reference natural amino acid. For instance, a natural amino acid is substituted by the corresponding β-amino acid. β-amino acids have their amino group bonded to the R carbon rather than the α carbon as in the natural amino acids. For instance, α-alanine is substituted by β-alanine, etc. Other preferred examples of substitution of a natural amino acid by a non-natural amino acid that is a derivative of the natural amino acid are the following. A preferred non-natural amino acid substituent for alanine is selected from the group consisting of beta-alanine, t-butylalanine, 2-napthylalanine; L-3-(2-naphthyl)alanine and 2-aminoisobutyric acid. A preferred non-natural amino acid substituent for arginine is selected from the group consisting of homoarginine, ornithine, N5-carbamoylornithine and 3-amino-propionic acid. A preferred non-natural amino acid substituent for asparagine is N-ethylasparagine. A preferred non-natural amino acid substituent for aspartic acid is 4-tert-butyl hydrogen 2-azidosuccinate. A preferred non-natural amino acid substituent for cysteine is selected from the group consisting of cysteic acid and homocysteine. A preferred non-natural amino acid substituent for glutamic acid is selected from the group consisting of γ-carboxy-DL-glutamic acid and 4-fluoro-DL-glutamic acid. A preferred non-natural amino acid substituent for glutamine is selected from the group consisting of D-citrulline and thio-L-citrulline. A preferred non-natural amino acid substituent for glycine is selected from the group consisting of N-methylglycine, t-butylglycine, N-methylglycine and D-allylglycine. A preferred non-natural amino acid substituent for histidine is 3-(3-methyl-4-nitrobenzyl)-L-histidine methyl ester. A preferred non-natural amino acid substituent for isoleucine is selected from the group consisting of isodesmosine, N-methylisoleucine and allo-isoleucine. A preferred non-natural amino acid substituent for leucine is selected from the group consisting of norleucine, desmosine and 5,5,5-trifluoro-leucine. A preferred non-natural amino acid substituent for lysine is selected from the group consisting of 6-N-methyllysine, 2-aminoheptanoic acid, N-acetyl lysine, hydroxylysine and allo-hydroxylysine. A preferred non-natural amino acid substituent for methionine is methionine sulfoxide. A preferred non-natural amino acid substituent for phenylalanine is selected from the group consisting of p-amino-L-phenylalanine, 3-benzothienyl alanine p-bromophenylalanine, p-acyl-L-phenylalanine, 2-fluorophenylalanine, 3-fluorophenylalanine and 4-fluorophenylalanine. A preferred non-natural amino acid substituent for proline is selected from the group consisting of 3-hydroxyproline, 4-hydroxyproline and 1-acetyl-4-hydroxy-L-proline. A preferred non-natural amino acid substituent for serine is selected from the group consisting of homoserine, isoserine and 3-phenylserine. A preferred non-natural amino acid substituent for threonine is selected from the group consisting of D-thyroxine and allo-threonine. A preferred non-natural amino acid substituent for tryptophan is selected from the group consisting of 5-hydroxy-tryptophan, 5-methoxy-tryptophan and 5-fluoro-tryptophan. A preferred non-natural amino acid substituent for tyrosine is selected from the group consisting of O-methyl-L-tyrosine, O-4-allyl-L-tyrosine and 3-chloro-tyrosine. A preferred non-natural amino acid substituent for valine is selected from the group consisting of norvaline, N-methylvaline and 3-fluoro-valine.

As used herein a "peptide" refers to a peptide or polypeptide that comprise multiple amino acids. The terms "peptide" and "polypeptide" are used interchangeably. The smallest peptide according to the disclosure demonstrated to bind ITGA11 has a length of 5 amino acids. The smallest peptide according to the disclosure demonstrated to bind ITGA5 has a length of 6 amino acids. However, the amino acid sequence or variant thereof can be part of a larger peptide, i.e., of a peptide that has been N terminally and/or C-terminally extended by a one or more additional amino acids. The amino acid sequence or variant thereof of a peptide of the disclosure may also be N-terminally and/or C-terminally modified, preferably by comprising an N- and/or C-terminal elongating group. Alternatively, the amino acid sequence or a variant thereof is N- and/or C-terminally extended.

An ITGA11 binding peptide according to the disclosure, therefore, comprises at least 5 amino acids, preferably at least 6 amino acids, and may comprise up to 25 amino acids. Hence, an ITGA11 binding peptide according to the disclosure preferably consists of 5 to 25 amino acids, more preferably 6 to 25 amino acids. More preferably, an ITGA11 binding peptide according to the disclosure consists of 7 to 25 amino acids, more preferably 8 to 25 amino acids. The Examples show that an ITGA11 binding peptide of 8 amino acids showed stronger binding to ITGA11 that smaller peptides. In a further embodiment, an ITGA11 binding peptide according to the disclosure preferably consists of 9-25, 10-25, 11-25, 12-25 amino acids. An ITGA5 binding peptide comprises at least 6 amino acids and may comprise up to 25 amino acids. Hence, an ITGA5 binding peptide according to the disclosure preferably consists of 6 to 25 amino acids, more preferably 6 to 25 amino acids. More preferably, an ITGA11 binding peptide according to the disclosure consists of 7 to 25 amino acids. The Examples show that an ITGA5 binding peptide of 7 amino acids (AV3) has a high affinity for the receptor. In a further embodiment, an ITGA5 binding peptide according to the disclosure preferably has a length of 9-25, 10-25, 11-25, 12-25 amino acids. However, smaller peptides are preferred. A preferred peptide according to the disclosure is, therefore, 5-20 amino acids in length, more preferably 5-16 amino acids, more preferably 5-15 amino acids, more preferably 5-14 amino acids, more preferably 5-13 amino acids, more preferably 5-12 amino acids. For instance, a peptide according to the disclosure comprises 5-16 amino acids, i.e., 5, 6, 7, 8, 9, 10, 11, 12, 13, 14, 15 or 16 amino acids. Preferably, the peptide comprises at least 6 amino acids, such as 6-20, 6-16 or 6-15, 6-14, 6-13, 6-12 amino acids. A particularly preferred peptide has 6-20 amino acids, 6-16 amino acids or 6-12 amino acids. Further particularly preferred peptides according to the disclosure consist of 7-20 amino acids, 7-16 amino acids or 7 to 12 amino acids. Further particularly preferred peptides according to the disclosure consist of 8-20 amino acids, 8-16 amino acids or 8 to 12 amino acids. Further particularly preferred peptides according to the disclosure consist of 10-20 amino acids, 10-16 amino acids or 10 to 12 amino acids.

A peptide according to the disclosure may further have an N-terminal, C-terminal modification and/or an internal modification. Provided, therefore, is a peptide according to the disclosure comprising an N-terminal modification, C-terminal modification and/or an internal modification. Also provided is a compound comprising a peptide according to the disclosure, wherein the peptide has an N-terminal modification, a C-terminal modification or an internal modification. A preferred N-terminal modification is acetylation. A preferred C-terminal modification is amidation. A preferred internal modification is cyclization or bicyclization, for instance, as a result of formation of a disulfide bond between two cysteine residues. Provided, therefore, are peptides according to the disclosure comprising an N-terminal, C-terminal modification and/or an internal modification.

Also provided is a multimer of at least one peptide of the disclosure comprising the amino acid sequence SGLTEWLRWFNS (SEQ ID NO:1), or a variant thereof as defined herein and/or of the amino acid sequence SFATWTPNFERN (SEQ ID NO:2) or a variant thereof as defined herein and/or the amino acid sequence TTVRYYRITYGETGGN (SEQ ID NO:3) or a variant thereof as defined herein, for instance, a dimer, trimer, tetramer, pentamer, hexamer, heptamer or octamer. A preferred multimer is a dimer of two peptides according to the disclosure. Such multimer, preferably dimer, can be a homomultimer, comprising multiple of the same peptide according to the disclosure, such as a homodimer of two identical peptides according to the disclosure. Alternatively, such multimer can be a heteromultimer, comprising at least two different peptides according to the disclosure, such as a heterodimer of two different peptides of the disclosure. For instance, provided is a dimer of two different ITGA11 binding peptides comprising the amino acid sequence SGLTEWLRWFNS (SEQ ID NO:1), or a variant thereof as defined herein according to the disclosure. As another example, a dimer of two different ITGA5 binding peptides comprising the amino acid sequence TTVRYYRITYGETGGN (SEQ ID NO:3), or a variant thereof as defined herein according to the disclosure. As yet a further example, a dimer of one ITGA11 binding peptide comprising the amino acid sequence SGLTEWLRWFNS (SEQ ID NO:1), or a variant thereof as defined herein according to the disclosure and one ITGA5 binding peptide comprising the amino acid sequence TTVRYYRITYGETGGN (SEQ ID NO:3), or a variant thereof as defined herein according to the disclosure is provided. Dimers are, for instance, formed as a result of disulfide bond formation between two cysteine residues present in the peptide monomers. Therefore, a peptide according to the disclosure, preferably comprises a cysteine residue. A preferred dimer according to the disclosure comprises two peptides according to the disclosure, wherein each peptides comprises at least one cysteine residue. A particularly preferred peptide according to the disclosure is, therefore, RYYRITYC (SEQ ID NO:11). As demonstrated in the Examples (see FIG. 15) this peptide is particularly active in inhibiting migration of fibroblasts. Without wishing to be bound by theory it is believed that dimers are formed of this peptide as a result of formation of a disulfide bond between two cysteine residues in two different peptide molecules and that dimeric forms of the peptide are more effective. Provided, therefore, is a dimer comprising two peptides according to the disclosure. The peptides preferably each comprise a cysteine residue. The two peptides are further preferably identical.

In one embodiment, a peptide of the disclosure is a peptide that does not occur as such in nature, i.e., a peptide of the disclosure is a non-naturally occurring peptide. "Non-naturally occurring" as used herein means that the peptide is not found in nature in that form, preferably that the amino acid sequence of the peptide is not found in nature. Hence, in such embodiment, a peptide of the disclosure preferably comprises at least one amino acid substitution in the amino acid sequence as defined herein.

A peptide of the disclosure is advantageously incorporated in a controlled release and/or targeted delivery carrier. As used herein, the term "controlled release" refers to the release of the peptide of the disclosure in time-dependent manner. In one embodiment, controlled release refers to slow release. As used herein, the term "targeted delivery" refers to the release of the peptide of the disclosure in a site-directed manner. Use of a controlled release vehicle has the advantage that frequent administration such as by injection of the peptide of the disclosure can be avoided. Use of a targeted delivery vehicle has the advantage that the peptide of the disclosure is effectively delivered to and/or retained at a site of interest in a subject's body, such as a site of inflammation or a site of infection. Preferably, a peptide of the disclosure is targeted to a site infected by microorganisms including bacteria, fungi, viruses and parasites. Controlled release and/or targeted delivery carriers are well known in the art. Non-limiting examples of controlled release and/or targeted delivery vehicles are nanoparticles, microparticles, nanocapsules, nanocomplexes, polyplexes, carbon nanotubes, quantum dots, microcapsules, liposomes, microspheres, hydrogels, polymers, micelles, dendrimers, lipid complexes, serum albumin, antibodies, antibody fragments, cyclodextrins and dextran. Controlled release is, for instance, provided by incorporating a peptide of the disclosure in or on the surface of such carrier. The carriers are of materials that form particles that capture a peptide of the disclosure and slowly degrade or dissolve in a suitable environment, such as aqueous, acidic or basic environment or body fluids, and thereby release the peptide. Targeted delivery is, for instance, achieved by providing a carrier with targeting groups on the surface thereof. Examples of such carrier comprising targeting groups are antibody-functionalized carriers, carriers having a site-specific ligand and carriers having a positive or negative surface charge. Preferred particles for controlled release and/or targeted delivery are nanoparticles, i.e., particles in the range of about 1 to 500 nm in diameter, preferably up to about 200 nm in diameter, and liposomes, optionally provided with targeting groups. The disclosure further provides a compound comprising a peptide according to the disclosure or multimeric, preferably dimeric, peptide according to the disclosure. The component preferably comprises at least one further moiety. The compound preferably comprises a label, a linker, such as a PEG linker, an N-terminal modification, a C-terminal modification or an internal modification or the compound comprises the peptide or multimeric peptide coupled to or encapsulated into a carrier selected from the group consisting of nanoparticles, microparticles, nanocapsules, nanocomplexes, polyplexes, carbon nanotubes, quantum dots, microcapsules, liposomes, microspheres, hydrogels, polymers, micelles, dendrimers, lipid complexes, serum albumin, antibodies, antibody fragments, cyclodextrins and dextran.

Salts of peptides according to the disclosure are also provided. Such salts include, but are not limited to, acid addition salts and base addition salts. As used herein, "pharmaceutically acceptable salt" of a peptide refers to a salt that retains the desired ITGA11 or ITGA5 binding activity of the peptide, and is suitable for administration to humans or animals. Methods for the preparation of salts of peptides are known in the art and generally involve mixing of the peptide with a pharmaceutically acceptable acid or base, for instance, by reacting the free acid or free base forms of the product with one or more equivalents of the appropriate acid or base in a solvent or medium in which the salt is insoluble, or in a solvent such as water, which is then removed in vacuo or by freeze-drying, or by exchanging the cations of an existing salt for another cation on a suitable ion exchange resin. Examples of pharmaceutically acceptable acids and bases include organic and inorganic acids such as formic acid, acetic acid, propionic acid, lactic acid, glycolic acid, oxalic acid, pyruvic acid, succinic acid, maleic acid, malonic acid, trifluoroacetic acid, cinnamic acid, sulfuric acid, hydrochloric acid, hydrobromic acid, nitric acid, perchloric acid, phosphoric acid, and thiocyanic acid, which form ammonium salts with free amino groups of peptides, and bases that form carboxylate salts with free carboxylic groups of peptides, such as ethylamine, methylamine, dimethylamine, triethylamine, isopropylamine, diisopropylamine, and other mono-, di- and trialkylamines, and arylamines.

Peptides according to the disclosure can be prepared by various methods. For instance, a peptide can be synthesized by commonly used solid-phase synthesis methods, e.g., methods that involve t-BOC or FMOC protection of alpha-amino groups that are well known in the art. Here, amino acids are sequentially added to a growing chain of amino acids. Such methods are, for instance, described in Merrifield (1963), J. Am. Chem. Soc. 85: 2149-2156; and Atherton et al., "Solid Phase Peptide Synthesis," IRL Press, London, (1989). Solid-phase synthesis methods are particularly suitable for synthesis of peptides or relatively short length, such as peptides with a length of up to about 70 amino acids in large-scale production. Alternatively, a peptide of the disclosure can be prepared using recombinant techniques well known in the art in which a nucleotide sequence encoding the peptide is expressed in host cells.

The disclosure further provides a nucleic acid molecule comprising a nucleic acid sequence encoding a peptide according to the disclosure, which is herein also referred to as a nucleic acid molecule according to the disclosure. As used herein, a nucleic acid molecule or nucleic acid sequence of the disclosure comprises a chain of nucleotides, preferably DNA and/or RNA.

Further provided is a vector comprising a nucleic acid sequence molecule according to the disclosure. The term "vector" as used herein refers to a nucleic acid molecule, such as a plasmid, bacteriophage or animal virus, capable of introducing a heterologous nucleic acid sequence into a host cell. A vector according to the disclosure allows the expression or production of a peptide of the disclosure encoded by the heterologous nucleic acid sequence in a host cell. A vector used in accordance with the disclosure is, for instance, derived from an animal virus, examples of which include, but not limited to, vaccinia virus (including attenuated derivatives such as the Modified Vaccinia virus Ankara, MVA), Newcastle Disease virus (NDV), adenovirus or retrovirus. A vector according to the disclosure preferably comprises an expression cassette comprising a promoter that is suitable for initiation of transcription of a peptide according to the disclosure in the selected host cells. Examples of suitable promoters for expression of peptides according to the disclosure in eukaryotic host cells include, but are not limited to, beta-actin promoter, immunoglobulin promoter, 5S RNA promoter, or virus derived promoters such as cytomegalovirus (CMV), Rous sarcoma virus (RSV) and Simian virus 40 (SV40) promoters for mammalian hosts.

Further provided by the disclosure is a recombinant host cell comprising a nucleic acid molecule and/or a vector according to the disclosure. A host cell is a cell that has been transformed, or is capable of transformation, by a nucleic acid molecule such as a vector according to the disclosure. "Transformation" refers to the introduction of a foreign nucleic acid into a recipient cell. Transformation of a host cell can result in transient expression of a recombinant protein by the cell, meaning that the recombinant protein is only expressed for a defined period of time. Alternatively, transformation of a recipient cell can result in stable expression, meaning that the nucleic acid is introduced into the genome of the cell and thus passed on to next generations of cells. Additionally, inducible expression of a recombinant protein can be achieved. An inducible expression system requires the presence or absence of a molecule that allows for expression of a nucleic acid sequence encoding a peptide of the disclosure. Examples of inducible expression systems include, but are not limited to, Tet-On and Tet-Off expression systems, hormone inducible gene expression system such as, for instance, an ecdysone inducible gene expression system, an arabinose-inducible gene expression system, and a *Drosophila* inducible expression system using a pMT/BiP vector (Invitrogen), which comprises an inducible metallothioneine promoter. A host cell used in a method for the preparation of a peptide according to the disclosure is, for instance, a Gram-positive prokaryote, a Gram-negative prokaryote or a eukaryote. Preferably, the host cell is a eukaryotic cell, such as a plant cell, a yeast cell, a mammalian cell or an insect cell, most preferably an insect cell or a mammalian cell. Examples of suitable host cells include plant cells such as corn cells, rice cells, duckweed cells, tobacco cells (such as BY-2 or NT-1 cells), and potato cells. Examples of yeast cells are *Saccharomyces* and *Pichia*. Examples of insect cells are *Spodoptera frugiperda* cells, such as Tn5, SF-9 and SF-21 cells, and *Drosophila* cells, such as *Drosophila* Schneider 2 (S2) cells. Examples of mammalian cells that are suitable for expressing a peptide according to the disclosure include, but are not limited to, African Green Monkey kidney (Vero) cells, baby hamster kidney (such as BHK-21) cells, Human retina cells (for example, PerC6 cells), human embryonic kidney cells (such as HEK293 cells), Madin Darby Canine kidney (MDCK) cells, Chicken embryo fibroblasts (CEF), Chicken embryo kidney cells (CEK cells), blastoderm-derived embryonic stem cells (e.g., EB14), mouse embryonic fibroblasts (such as 3T3 cells), Chinese hamster ovary (CHO) cells, and derivatives of these cell types.

The disclosure thus provides a method for the preparation of peptide according to the disclosure comprising:
  providing a nucleic acid molecule comprising a nucleic acid sequence encoding peptide according to the disclosure;
  transforming a host cell with the nucleic acid molecule;
  culturing the host cell under conditions that allow expression of the peptide;
  harvesting the peptide from the cells.

A method according to the disclosure preferably further comprises a step of purifying and/or isolating peptides according to the disclosure. Obtained peptides according to the disclosure are preferably used in human therapy, optionally after additional purifying, isolation or processing steps, for instance, purification using gel electrophoresis or chromatography methods.

In one embodiment, peptides according to the disclosure bind to ITGA11 and/or α11β1 integrin. In another embodiment, peptides according to the disclosure bind to ITGA5 and/or α5β1 integrin. Binding of peptides to ITGA11, α11β1 integrin, ITGA5 and/or α5β1 integrin is, for instance, determined using coated receptor (ITGA11, α11β1 integrin, ITGA5 or α5β1 integrin) or peptide microarrays as described in the Examples. In the first assay, the relevant receptor is coated on, for instance, an ELISA plate and subsequently incubated with a peptide. In the second assay, a peptide is immobilized on an array and subsequently incubated with the relevant receptor.

An ITGA11 binding peptide according to the disclosure preferably has α11β1 integrin and/or ITGA11 inhibitory activity. The inhibiting activity preferably comprises inhibition of binding of α11β1 integrin and/or ITGA11 to fibroblasts, stellate cells, myofibroblasts, pericytes and/or other cells of mesenchymal origin, inhibition of migration of fibroblasts, stellate cells, myofibroblasts, pericytes and/or other cells of mesenchymal origin, inhibition of differentiation of fibroblasts, stellate cells, myofibroblasts, pericytes and/or other cells of mesenchymal origin and/or inhibition of extracellular matrix synthesis and/or deposition.

An ITGA5 binding peptide according to the disclosure preferably has α5β1 integrin and/or ITGA5 inhibitory activity. The inhibiting activity preferably comprises inhibition of binding of α5β1 integrin and/or ITGA5 to fibroblasts, stellate cells, myofibroblasts, pericytes and/or other cells of mesenchymal origin, preferably of fibroblasts, myofibroblasts and/or stellate cells, inhibition of migration of fibroblasts, stellate cells, myofibroblasts, pericytes and/or other cells of mesenchymal origin, preferably of fibroblasts, myofibroblasts and/or stellate cells, inhibition of differentiation of fibroblasts, stellate cells, myofibroblasts, pericytes and/or other cells of mesenchymal origin, preferably of fibroblasts, myofibroblasts and/or stellate cells, and/or inhibition of extracellular matrix synthesis and/or deposition. Stellate cells include, but are not limited to, hepatic stellate cells, pancreatic stellate cells and podocytes. The inhibiting activity more preferably comprises at least inhibition of migration of fibroblasts, stellate cells, myofibroblasts, pericytes and/or other cells of mesenchymal origin, preferably of fibroblasts, myofibroblasts and/or stellate cells, more preferably of fibroblasts.

A peptide or compound according to the disclosure can be advantageously used in both therapeutic and nontherapeutic applications. In particular, peptides and compounds according to the disclosure are useful as therapeutic, prophylactic, diagnostic or targeting agents.

Further provided, therefore, is a pharmaceutical composition comprising a peptide according to the disclosure or a multimeric, preferably dimeric, peptide according to the disclosure or a pharmaceutically acceptable salt thereof or a nucleic acid molecule according to the disclosure and at least one pharmaceutically acceptable carrier, diluent and/or excipient. Such pharmaceutical composition may comprise an ITGA11 binding peptide or multimeric peptide according to the disclosure, an ITGA5 binding peptide or multimeric peptide according to the disclosure or a combination thereof. Alternatively, a pharmaceutical composition comprises more than one ITGA11 binding peptide or multimeric peptide according to the disclosure and/or more than one ITGA5 binding peptide or multimeric peptide according to the disclosure or combinations thereof.

Also provided is a pharmaceutical composition comprising a compound according to the disclosure comprising a peptide according to the disclosure or a multimeric, preferably dimeric, peptide according to the disclosure and at least one pharmaceutically acceptable carrier, diluent and/or excipient. Such pharmaceutical composition may comprise one or more compounds comprising an ITGA11 binding peptide or multimeric peptide according to the disclosure, one or more compounds comprising an ITGA5 binding peptide or multimeric peptide according to the disclosure or combinations thereof.

The disclosure further provides a peptide according to the disclosure or multimeric, preferably peptide according to the disclosure for use as a medicament. Further provided is a nucleic acid molecule comprising a nucleic acid sequence encoding a peptide according to the disclosure for use as a medicament. Further provided is a compound according to the disclosure comprising a peptide according to the disclosure or multimeric, preferably peptide according to the disclosure for use as a medicament. The medicament can be a therapeutic or a prophylactic agent.

The pharmaceutical compositions described herein can be administered in a variety of different ways. Examples include administering a pharmaceutical composition comprising a peptide according to the disclosure or multimeric, preferably peptide according to the disclosure and containing a pharmaceutically acceptable carrier via oral, intranasal, rectal, topical, intraperitoneal, intravenous, intramuscular, subcutaneous, subdermal, transdermal, intrathecal, and intracranial methods. For oral administration, the active ingredient can be administered in solid dosage forms, such as capsules, tablets, and powders, or in liquid dosage forms, such as elixirs, syrups, and suspensions.

Pharmaceutical compositions according to the disclosure comprise at least one pharmaceutically acceptable carrier, diluent or excipient. Examples of suitable carriers, for instance, comprise keyhole limpet hemocyanin (KLH), serum albumin (e.g., BSA or RSA) and ovalbumin. In a preferred embodiment, the suitable carrier is a solution, for example, saline. Examples of excipients that can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor. A pharmaceutical composition according to the disclosure is preferably suitable for human use.

Sterile compositions for injection can be formulated according to conventional pharmaceutical practice by dissolving or suspending the peptide of the disclosure in a vehicle for injection, such as water or a naturally occurring vegetable oil like sesame oil, coconut oil, peanut oil, cottonseed oil, etc., or a synthetic fatty vehicle like ethyl oleate or the like. Buffers, preservatives, antioxidants and the like may also be incorporated.

Compositions for topical administration can also be formulated according to conventional pharmaceutical practice. "Topical administration" as used herein refers to application to a body surface such as the skin or mucous membranes to locally treat conditions resulting from microbial or parasitic infections. Examples of formulations suitable for topical administration include, but are not limited to a cream, gel, ointment, lotion, foam, suspension, spray, aerosol, powder aerosol. Topical medicaments can be epicutaneous, meaning that they are applied directly to the skin. Topical medicaments can also be inhalational, for instance, for application to the mucosal epithelium of the respiratory tract, or applied to the surface of tissues other than the skin, such as eye drops applied to the conjunctiva, or ear drops placed in the ear. The pharmaceutical composition formulated for topical administration preferably comprises at least one pharmaceutical excipients suitable for topical application, such as an emulsifier, a diluent, a humectant, a preservatives, a pH adjuster and/or water.

A peptide according to the disclosure or multimeric, preferably dimeric, peptide according to the disclosure is particularly useful in the treatment or prevention of fibrosis and/or a fibrosis related disorder, an inflammatory disease and/or cancer. Preferably, a peptide according to the disclosure or multimeric, preferably dimeric, peptide according to the disclosure is used in the treatment of fibrosis and/or a fibrosis related disease or cancer, more preferably in the treatment of fibrosis or a fibrosis related disease. The present inventors have developed novel ITGA5 and ITGA11 binding peptides. Without wishing to be bind by theory it is believed that these peptides can be used to block ITGA5 or ITGA11 in, e.g., fibroblasts, stellate cells, myofibroblasts, pericytes and/or other cells of mesenchymal origin and thereby inhibit their differentiation. During tissue repair, cells such as fibroblasts and stellate cells change their phenotype from the normal relatively quiescent state in which they are involved in turnover of the extracellular matrix to myofibroblast, which have a more proliferative and contractile phenotype. During normal tissue repair processes, scars are formed and myofibroblasts undergo apoptosis. In pathological fibroses, myofibroblasts remain in the tissue and are responsible for fibrosis via increased matrix synthesis and contraction of the tissue. Inhibition of differentiation of, e.g., fibroblasts, stellate cells, myofibroblasts, pericytes and/or other cells of mesenchymal origin, therefore, contribute to counteracting the development and/or progression of fibrosis. The peptides of the disclosure can thus be used as anti-fibrotic agents and anti-cancer agents.

Provided, therefore, is a method for the treatment of a subject suffering from fibrosis or a fibrosis related disorder, an inflammatory disease or cancer comprising administering to the subject a therapeutically effective amount of a peptide according to the disclosure or multimeric, preferably peptide according to the disclosure or a pharmaceutical composition according to the disclosure. Also provided is a method for the treatment of a subject suffering from fibrosis or a fibrosis related disorder, an inflammatory disease or cancer comprising administering to the subject a therapeutically effective amount of a nucleic acid molecule according to the disclosure.

Also provided is a peptide according to the disclosure or multimeric, preferably peptide according to the disclosure for use in the treatment or prevention of fibrosis and/or a fibrosis related disorder, an inflammatory disease and/or cancer. Further provided is a compound comprising a peptide according to the disclosure or multimeric, preferably peptide according to the disclosure for use in the treatment or prevention of fibrosis and/or a fibrosis related disorder, an inflammatory disease and/or cancer.

Also provided is the use of a peptide according to the disclosure or multimeric, preferably peptide according to the disclosure for the preparation of a medicament for the treatment or prevention of fibrosis and/or a fibrosis related disorder, an inflammatory disease and/or cancer. Further provided is the use of a compound comprising a peptide according to the disclosure or multimeric, preferably peptide according to the disclosure for the preparation of a medicament for the treatment or prevention of fibrosis and/or a fibrosis related disorder, an inflammatory disease and/or cancer.

As used herein, a "subject" is a human or an animal. Subjects include, but are not limited to, mammals such as humans, pigs, ferrets, seals, rabbits, cats, dogs, cows and horses. In a preferred embodiment of the disclosure a subject is a mammal. In a particularly preferred embodiment the subject is a human.

The peptides, compounds and compositions containing the peptides or compounds can be administered for prophylactic and/or therapeutic treatments. In a preferred embodiment, the peptides, compounds and compositions containing the peptides or compounds are administered for therapeutic treatments. In therapeutic applications, peptides or compositions are administered to a subject, preferably a human, already suffering from fibrosis, or a fibrosis related disorder, an inflammatory disease or cancer in an amount sufficient to counteract the disease and its complications. The peptide or compound is typically present in a pharmaceutical composition according to the disclosure in a therapeutic amount, which is an amount sufficient to remedy a condition or disease, particularly fibrosis, or a fibrosis related disorder, an inflammatory disease or cancer. Typical doses of administration of a peptide according to the disclosure or multimeric, preferably peptide according to the disclosure are between 0.01 and 10 mg peptide per kg body weight, depending on the size of the peptide.

The term "fibrosis" as used herein refers to a condition characterized by a deposition of extracellular matrix components in the skin or organs, including lungs, kidneys, heart, liver, skin and joints, resulting in scar tissue. The term also refers to the process of formation of scar tissue. Treatment of fibrosis or a fibrosis related disorder refers to treatment of subjects who have already developed a fibrotic condition. Prevention of fibrosis or a fibrosis related disorder refers to prognostic treatment of subjects at risk of developing a fibrotic condition. The term "fibrosis-related disorder" is herein defined as a disorder or condition that may occur as a result of fibrosis or that is associated with fibrosis. Fibrosis and/or a fibrosis-related disorders preferably refers to a disease or condition selected from the group consisting of kidney fibrosis, liver fibrosis, liver cirrhosis, pulmonary fibrosis, skin fibrosis, biliary fibrosis, peritoneal fibrosis; myocardial fibrosis; pancreatic fibrosis, reperfusion injury after hepatic or kidney transplantation, Interstitial Lung Disease (ILD), cystic fibrosis (CF), atherosclerosis, systemic sclerosis, osteosclerosis, spinal disc herniation and other spinal cord injuries, fibromatosis, fibromyalgia, arthritis, restenosis. Pulmonary fibrosis includes idiopathic pulmonary fibrosis and scleroderma lung fibrosis. Skin fibrosis includes scleroderma, keloid, hypertrophic scar, dermatofibroma, wounds, chronic wounds, skin scarring, psoriasis and burns. In a preferred embodiment, the fibrosis and/or a fibrosis-related disorder is selected from the group consisting of liver fibrosis, skin fibrosis, idiopathic pulmonary fibrosis, kidney fibrosis and atherosclerosis.

Inflammation can be an initial stage of fibrosis. For example, hepatitis leads to liver fibrosis and nephritis leads to renal fibrosis. An "inflammatory disease" as used herein refers to any disease associated with an excessive or unregulated inflammatory response. An inflammatory disease treated in accordance with the disclosure preferably is an inflammatory disease causing tissue damage and fibrosis. Preferably an inflammatory disease treated in accordance with the disclosure is selected from the group consisting of arthritis, such as rheumatoid arthritis (RA), psoriatic arthritis, ankylosing spondylitis and juvenile idiopathic arthritis; inflammatory bowel diseases, such as ulcerative colitis, Crohn's disease, Coeliac disease, enteritis, necrotizing enterocolitis, and gluten-sensitive enteropathy; inflammatory diseases of the respiratory system, such as asthma, including bronchial asthma, allergic asthma, intrinsic asthma, extrinsic asthma and dust asthma, idiopathic interstitial pneumonia, adult respiratory distress syndrome, allergic rhinitis, chronic obstructive airway disease, reversible obstructive airway disease, hypersensitivity lung diseases, airway hyper-responsiveness and bronchiolitis; inflammatory diseases of the skin, such as psoriasis, scleroderma, eczema, atopic dermatitis, contact dermatitis, seborrhoeic dermatitis, dermatomyositis, dermatitis erythema multiforme and urticaria; hepatitis, including autoimmune hepatitis and viral hepatitis; nephritis, including glomerulonephritis, interstitial nephritis and pyelonephritis; pancreatitis, vasculitis, gingivitis, periodontitis sarcoidosis, thyroiditis, otitis, conjunctivitis, sinusitis, sarcoidosis and infectious diseases caused by pathogenic microorganisms. In a particularly preferred embodiment, the inflammatory disease is selected from the group consisting of nephritis, hepatitis, pancreatitis, inflammatory diseases of the skin and inflammatory diseases of the respiratory system.

The term "cancer" refers to any type of malignant tumor or malignant neoplasm. Cancer treated in accordance with the present disclosure is preferably selected from the group consisting of lung cancer, pancreatic cancer, breast cancer, liver cancer, brain cancer, skin cancer, colon cancer, cancer of the small intestine, stomach cancer, uterine cancer, kidney cancer, renal cell carcinoma, prostate cancer, gall bladder cancer, cancer of the head or neck, ovarian cancer, cervical cancer, glioblastoma, melanoma, chondrosarcoma, fibrosarcoma, desmoplastic small round cell tumor, endometrial, esophageal, eye or gastrointestinal stromal tumor, liposarcoma, nasopharyngeal, thyroid, vaginal and vulvar tumors, and other tumors with desmoplasia. In a preferred embodiment, cancer treated in accordance with the disclosure is a tumor with desmoplasia. "Tumor with desmoplasia" as used herein refers to a tumor associated with the growth of fibrous or connective tissue. In a particularly preferred embodiment, the cancer is selected from the group consisting of lung cancer, pancreatic cancer, liver cancer, breast cancer, prostate cancer, kidney cancer. Treatment of cancer encompasses reduction of tumor size, inhibition of tumor growth and inhibition of metastasis formation.

Peptides of the disclosure are suitably used as targeted delivery agents, for instance, to deliver a therapeutic molecule or an imaging agent to a site of interest. Provided, therefore, is a use of a peptide according to the disclosure or multimeric, preferably peptide according to the disclosure as an imaging or targeting agent. Also provided is a peptide according to the disclosure or multimeric, preferably peptide according to the disclosure for use as a targeting agent. Also provided is a method of imaging a tissue expressing integrin alpha 11 (ITGA11), preferably expressing α11β1 integrin, by contacting the tissue with a ITGA binding peptide or multimeric, preferably dimeric, peptide according to the disclosure. In one embodiment, the method is an in vitro method, e.g., for imaging tissue or cell samples. In another embodiment, the method is an in vivo method, e.g., for imaging tissues or cells in vivo. An ITGA11 binding peptide is preferably used to deliver a therapeutic or imaging agent to a tissue expressing ITGA11 and/or α11β1 integrin, such as fibrotic tissue or tumor tissue. Also provided is a method of imaging a tissue expressing integrin alpha 5 (ITGA5), preferably expressing α5β1, by contacting the tissue with an ITGA5 binding peptide or multimeric, preferably dimeric, peptide according to the disclosure. In one embodiment, the method is an in vitro method, e.g., for imaging tissue or cell samples. In another embodiment, the method is an in vivo method, e.g., for imaging tissues or cells in vivo. An ITGA5 binding peptide is preferably used to deliver a therapeutic or imaging agent to a cell or tissue expressing ITGA5 and/or α5β1 integrin, such as (cells in) fibrotic tissue or tumor tissue.

Therapeutic molecules that can be targeted to a site of interest using a peptide of the disclosure are, for instance, proteins or peptides, cytokines, drug-containing nanoparticles, small molecule therapeutics and/or chemotherapeutic agents. Such therapeutic molecule is, for instance, coupled to a peptide according to the disclosure or multimeric, preferably peptide according to the disclosure. In one embodiment, a peptide according to the disclosure or multimeric, preferably peptide according to the disclosure is preferably used to target a therapeutic molecule to fibrotic tissue or cells in fibrotic tissue expressing ITGA11 and/or α11β1 integrin and/or ITGA5 and/or α5β1 integrin. The therapeutic agent can be any agent known in the art suitable for treatment of fibrosis or a fibrosis related disorder, such as those selected from the group consisting of pirfenidone (5-Methyl-1-phenylpyridin-2-one), tranilast (2-{[(2E)-3-(3, 4-dimethoxyphenyl)prop-2- enoyl]amino}benzoic acid), interferon-β1a, interferon-γ, colchicine, D-penicillamine, relaxin, lovastatin, acetylcysteine, keratinocyte growth factor, hepatocyte growth factor, captopril, bilirubin and imatinib. In another embodiment, a peptide according to the disclosure or multimeric, preferably peptide according to the disclosure, is preferably used to target a therapeutic molecule to tumor cells expressing ITGA11 and/or α11β1 integrin and/or ITGA5 and/or α5β1 integrin. The therapeutic agent can be any anticancer agent known in the art, such as hormonal therapeutic agents, chemotherapeutic agents, immunotherapeutic agents, including, but not limited to, those selected from the group consisting of dexamethasone, prednisolone, betamethasone, triamcinolone, abiraterone, liarozole, cyclophosphamide, ifosfamide, fosfestrol, diethylstylbestrol, chlorotrianisene, medroxyprogesterone acetate, megestrol acetate, chlormadinone, cyproterone acetate, danazol, allylestrenol, gestrinone, mepartricin, raloxifene, ormeloxifene, levormeloxifene, tamoxifen, toremifene, fulvestrant, gonadotropin, follicle stimulating hormone, mepitiostane, testrolactone, aminoglutethimide, goserelin, buserelin, leuprorelin, droloxifene, epitiostanol, ethinylestradiol, anastrozole, retrozole, exemestane, vorozole, formestane, flutamide, finasteride, dutasteride, epristeride, thiotepa, carboquone, improsulfan, busulfan, nimustine, mitobronitol, melphalan, dacarbazine, ranimustine, estramustine, carmustine, lomustine, streptozocin, etoglucid, carboplatin, cisplatin, miboplatin, nedaplatin, oxaliplatin, altretamine, ambamustine, dibrospidium, fotemustine, prednimustine, pumitepa, ribomustin, temozolomide, treosulphan, trophosphamide, zinostatin stimalamer, adozelesin, cystemustine, bizelesin, mercaptopurine, 6-mercaptopurine riboside, thioinosine, methotrexate, enocitabine, cytarabine, cytarabine, ancitabine, fluorouracil, doxifluridine, carmofur, gallocitabine, emmitefur, aminopterin, butocine, folinate calcium, levofolinate calcium, cladribine, emitefur, fludarabine, gemcitabine, pentostatin, piritrexim, idoxuridine, mitoguazone, thiazophrine, ambamustine, actinomycin D, actinomycin C, mitomycin C, chromomycin A3, bleomycin, bleomycin sulfate, daunorubicin, doxorubicin, pirarubicin, epirubicin, neocarzinostatin, mithramycin, sarcomycin, carzinophilin, mitotane, zorubicin, mitoxantrone, idarubicin, etoposide, etoposide phosphate, vinblastine, vincristine, vindesine, teniposide, paclitaxel, docetaxel, vinorelbine, picibanil, krestin, sizofiran, lentinan, ubenimex, interferons, interleukins, macrophage colony-stimulating factor, granulocyte colony-stimulating factor, erythropoietin and lymphotoxin.

A peptide according to the disclosure or multimeric, preferably peptide according to the disclosure may be provided with an imaging label. Examples of imaging labels that can be used include enzymes, fluorescent compounds, radioisotopes, chemiluminescent compounds and bioluminescent compounds. Such imaging labels are well known in the art generally available. Non-limiting examples of labels are biotin, fluorescein, dansyl, 7-methoxycoumarin acetic acid (Mca), palmitic acid. Such label is, for instance, attached to the N-terminus or C-terminus of a peptide using available methods well known in the art. Provided, therefore, is a compound comprising a peptide according to the disclosure and a label, preferably an imaging label. Preferred examples of labels are an enzyme, a fluorescent label, a radioisotope, a chemiluminescent label and a bioluminescent label. A particularly preferred label is a fluorescent label.

Peptides according to the disclosure provided with an imaging label can be used both in vitro and in vivo. In vitro use, for instance, encompasses labeling of ITGA11 and/or α11β1 integrin and/or ITGA5 and/or α5β1 integrin in tissue samples of an individual, e.g., for research or diagnostic purposes. Examples of in vivo use of a peptide according to the disclosure or multimeric, preferably peptide according to the disclosure are image-guided surgery and image-guided drug delivery. Image-guided surgery refers to a surgical procedure where, e.g., tissue of interest is labeled real-time in order to assist in or guide de surgical procedure. In image-guided drug delivery tumor localization and drug delivery are guided and monitored through (noninvasive) imaging.

Provided, therefore, is a peptide according to the disclosure or multimeric, preferably peptide according to the disclosure or compound according to the disclosure comprising such peptide for use as a diagnostic agent. Such peptide is, for instance, coupled to an imaging label as described herein. The diagnostic agent is preferably for use in diagnosis of fibrosis or a fibrosis related disorder, an inflammatory disease or cancer. Provided is also a method for diagnosis of fibrosis or a fibrosis related disorder, an inflammatory disease or cancer, the method comprising contacting a sample from a subject suspected of suffering from fibrosis or a fibrosis related disorder, an inflammatory disease or cancer with a peptide according to the disclosure or multimeric, preferably peptide according to the disclosure or compound according to the disclosure comprising such peptide. Further provided is a peptide according to the disclosure or multimeric, preferably peptide according to the disclosure or compound according to the disclosure comprising such peptide for use as an imaging agent. Such peptide is, for instance, coupled to an imaging label as described herein. The imaging agent is preferably for use in diagnosis of fibrosis or a fibrosis related disorder, an inflammatory disease or cancer.

Features may be described herein as part of the same or separate aspects or embodiments of the present disclosure for the purpose of clarity and a concise description. It will be appreciated by the skilled person that the scope of the disclosure may include embodiments having combinations of all or some of the features described herein as part of the same or separate embodiments.

The disclosure will be explained in more detail in the following, non-limiting examples.

EXAMPLES

Example 1

Materials and Methods
Materials

Peptide Phage Display Ph.D.12™ Library was originally obtained by New England Biolabs. *E. coli* ER2738 host strain were purchased from New England Biolabs. The target protein rhIntegrin α11β1 and control protein rhIntegrin α4/β1 was purchased from R&D systems.

Biopanning

ER2738 host cells were cultivated overnight to use them freshly. 100 μl of the target protein α11β1 (50-100 μg/mL) in coating buffer (0.1 M NaHCO$_3$) was incubated in 96-well plates at 4° C. overnight. Then, each well was blocked with 300 μL of blocking buffer 0.1 M NaHCO$_3$ (pH 8.6), 5 mg/mL BSA, 0.02% NaN3, 0.1 μg/mL streptavidin at 37° C. for 2 hours. The blocked wells were then washed 6 times with 2% skimmed milk in PBST with 0.1-0.3% TWEEN®-20. Thereafter, the pre-subtracted phages were transferred into the wells and incubated at 37° C. for 1 hour. The wells were washed 10 times with 2% Milk in PBST (0.1-0.3% TWEEN®-20). The bound phages were eluted with acidic elution buffer and neutralize with 1 M Tris-HCl (pH 9.1).

Titration of the Eluate

In brief, 1 μL of eluate was diluted in 100 μL of LB medium and serial dilutions were prepared. The dilutions were mixed with 200 μL of mid-log host cells in test tubes at first and then added the mixture into 3 mL pre-warmed Agarose Top (45° C.), vortexed quickly and poured onto a pre-warmed LB/IPTG/Xgal plate immediately to spread Agarose Top evenly. After cooling at room temperature for about 5 minutes, plates were inverted and then incubated at 37° C. overnight. At last, plates were inspected and blue plaques (carrying phage vectors) on plates were counted having about 100 plaques. The pfu (plaque forming units) per mL were determined by multiplying each number by the dilution factor.

Amplification of the Eluate

The rest of the eluate of the $1^{st}$ or $2^{nd}$ round of screening were amplified by infecting 20 mL ER2738 cell culture and incubating at 37° C. for 4.5 hours. Amplified phages contained in the cell supernatant were precipitated by adding ⅙ volume of PEG/NaCl and incubate at 4° C. overnight. The precipitated phages were titrated on LB/IPTG/X-gal plates and preserved for the next round of screening.

Phage ELISA Assay

For each clone, 20 mL of LB medium was inoculated with ER2738 and incubated at 37° C. until slightly turbid. Single plaque of phages were inoculated to each culture and then incubated at 37° C. with vigorous aeration for 4.5 hours. The cultures were transferred to a fresh centrifuge tube and centrifuged for 10 minutes at 10,000 rpm. The upper 80% of the supernatant was transferred to a fresh tube and precipitated with PEG/NaCl twice. Then the pellet was suspended in 250 μL TBS. The 96-well ELISA plate was coated with 100 μL of 1 μg/mL target in coating buffer and incubated at 4° C. overnight. Then, the plate was washed once with the washing buffer (0.1% TWEEN® in TBS). All wells were blocked with 250 μL of blocking buffer at 4° C. for 1-2 hours. Then, the plate was washed 6 times with the washing buffer and slapping on a paper towel to remove excess buffer. Thereafter, 100 μL of phage virions was added per well. In competitive phage ELISA, competitive antigen was mixed with phages in washing buffer and added to the wells and incubated at room temperature for 1-2 hours with agitation. The plate was washed 6 times with washing buffer. HRP-conjugated anti-M13 antibody (GE healthcare, 1:5000 in blocking buffer) was added to each well and incubated at room temperature for 1 hour with agitation. Then, the plate was washed 6 times with washing buffer. The 100 μL HRP substrate solution (22 mg OPD (Sigma) in 100 mL of 50 mM sodium citrate, pH 4.0 with freshly added 36 μL of 30% $H_2O_2$ to 21 mL of OPD stock solution) was added to each well and incubated at room temperature for 10-60 minutes. The plates were read using a microplate reader at 490 nm.

Isolation of ssDNA for Sequencing

The single plaques were amplified by infecting 2 mL ER2738 cell culture and incubating at 37° C. for 4.5 hours. 500 μL of the phage-containing supernatant was transferred to a fresh tube, added with 200 μL PEG/NaCl and mixed. The tube was centrifuged at the top speed for 10 minutes and supernatant was discarded. The pellet was suspended thoroughly in 100 μL iodide buffer, added with 250 μL ethanol and incubated for 10 minutes at room temperature. Then the tube was centrifuged for 10 minutes and supernatant was discarded. The pellet was washed in 70% ethanol, dried briefly under vacuum. The pellet was suspended in 30 μL TE buffer and 5 μL of the re-suspended template was used for DNA sequencing. The sequences were translated with professional software (Vector NTI®, Version 10).

Synthesis of Peptide and Peptide-PEG-FITC

Peptides and peptide-PEG(6)-FITC were custom-synthesized by Chinapeptides, Shanghai, China at >95% purity. The successful syntheses of peptides were confirmed by mass spectrometry analyses.

Binding of Peptides to ITGA11 Receptor

Purified ITGA11 receptor (α11β1; 100 μg/ml—stock; R&D systems) was diluted to 5 μg/ml with 1×PBS. 96-well ELISA White Maxisorb plate (Nunc) was coated with 50 μl of 5 μg/ml ITGA11 (or as control α5β1) receptor for overnight at 4° C. Then, wells were blocked for 3-4 hours with 200 μl of blocking buffer (1×PBS containing 5% BSA). Wells were washed three times with 200 μl of washing buffer (1×PBS containing 0.5% BSA and 0.05% TWEEN®-20). Peptides conjugated with FITC were diluted to different concentrations in washing buffer and then added to the plate and incubated at 37° C. for 1 hour. In addition, the binding of the peptide was blocked by co-incubation with 10× higher amount of unlabeled peptide. Subsequently, wells were washed three times with washing buffer. Then, 100 μl of 1×PBS was added and plates were read at 485 nm/520 nm with a fluorescence plate reader.

Cell Binding Experiment

Human hepatic stellate cells (LX2, 15,000 cells/well) were cultured overnight in permanox Lab-Tek 8-well chamber slides (Nunc). After overnight incubation, cells were washed 3× with 0.5% BSA containing medium and then FITC-labeled peptides (20 μM) was added and incubated at room temperature for 2 hours with intermittent shaking. The cells were then washed 3× with 0.5% BSA containing medium and 2×PBS. Thereafter, cells were fixed with 4% paraformaldehyde (prepared in 1×PBS) for 20 minutes followed by 3 times washing with 1×PBS. Cells were then mounted with mounting medium with DAPI (vector labs) and visualized under the fluorescence microscope (Nikon E600). For phalloidin staining, cells after fixation were incubated with TRITC-conjugated Phalloidin (1:1000 prepared in 1×PBS containing 0.1% TRITON-X® 100) for 10 minutes. Then, cells were washed thrice with PBS and mounted with DAPI-containing mounting medium.

CCl4-Induced Liver Fibrosis Mouse Model

All animal experiments were approved by ethical committee of Utrecht University. C57/BL6 mice (7-8 weeks old) were obtained from Harlan (Zeist, The Netherlands) and kept at 12/12 light dark cycle with adequate food and water supply. CCl4 was intraperitoneally administered in mice (2× per week; 1.0 ml/kg prepared in olive oil) for 4 weeks (mild fibrosis) and 8 weeks (advanced fibrosis). 24 hours after the last administration, animals were sacrificed and pieces were excised out from each liver lobe and collected in Eppendorf tube and were snap frozen in liquid nitrogen for RNA isolation. Normal control mice received olive oil.

To assess the effect of AXI-I peptide on liver fibrosis, animals were injected with a single dose of CCl4 (1 ml/kg) at day 0. Subsequently, mice were injected with the peptide (200 μg/kg/d, i.p) or vehicle (PBS) on days 1 and 2. On day 4, mice were sacrificed and the liver samples were processed for immunohistochemistry analyses and gene expression studies.

In Vitro Gene Expression Studies

Hepatic stellate LX2 cells (80,000 cells/well) were plated in 12-well plates and incubated overnight at 37° C./5% CO2. Then, cells were starved in 0.5% serum containing medium overnight and then activated with 5 ng/ml TGFβ for 24 hrs. Subsequently, cells were washed with 1×PBS and lysed with 200 μl of RNA lysis buffer. Total RNA was isolated using SV Total RNA Isolation System (Promega) according to manufacturer's instructions. RNA concentration was quantified using UV spectrophotometer (Nanodrop technologies). 1 µg RNA was reverse transcribed using iScript cDNA synthesis kit (Biorad). The real-time PCR reactions were performed with 20 ng cDNA using 2×SYBR green PCR master mix (Bioline) according to manufacturer's instructions and were analyzed by Biorad CFX384 Real-Time PCR detection system. Finally, the threshold cycles (Ct) were calculated and relative gene expression was normalized with GAPDH (for mouse) as housekeeping gene.

ITGA 11 human Forward:
CAGCTCGCTGGAGAGATACG; (SEQ ID NO: 12)

Reverse:
TTACAGGACGTGTTCGCCTC; (SEQ ID NO: 13)

GAPDH human Forward:
TCCAAAATCAAGTGGGGCGA; (SEQ ID NO: 14)

Reverse:
TGATGACCCTTTTGGCTCCC; (SEQ ID NO: 15)

a-sma human Forward:
GAACCCTGTGTCCTGCATCA; (SEQ ID NO: 16)

Reverse:
TTGGAGTTCCACCTCGAAGC; (SEQ ID NO: 17)

ITGA11 mouse Forward:
TTGGGCTACTACAACCGCAG; (SEQ ID NO: 18)

Reverse:
CTTGTTGGTGCCTTCCAAGC; (SEQ ID NO: 19)

GAPDH mouse Forward:
ACAGTCCATGCCATCACTGC; (SEQ ID NO: 20)

Reverse:
GATCCACGACGGACACATTG; (SEQ ID NO: 21)

α-sma mouse Forward:
ACTACTGCCGAGCGTGAGAT; (SEQ ID NO: 22)

Reverse:
CCAATGAAAGATGGCTGGAA. (SEQ ID NO: 23)

Binding Studies on Peptide Microarray

Peptide microarray was prepared by conjugating peptides at their N-terminal to a glass slide using a PEG linker. Each peptide was displayed three times at different positions to avoid artefacts and errors. For the binding studies, the peptide array was blocked with 3% BSA in TBST for 2 hours. Then the array slide was washed 5 times in TBST and subsequently incubated with the target receptor (α11β1, 10 µg/ml dissolved in PBS) for 1 hour at 37° C. The slides were washed with TBST and then incubated with primary antibody (1 µg/ml) against ITGA11 for 1 hour at 37° C. Then slides were washed and incubated with fluorescent dye labeled secondary antibodies for 30 minutes. The slides were washed with TBST and water and then dried and scanned with a microarray scanner to detect binding of the peptides. The enlightened spots were analyzed using ImageJ software. To determine the unspecific binding, a peptide array was incubated with only primary and secondary antibodies without the receptor incubation step. Then, the signal of unspecific binding was subtracted from the total binding to calculate specific binding.

Expression of ITGA in Human Liver Cirrhosis and Pancreatic Cancer

Immunohistochemical staining was performed as described in Example 2.

AXI-PEG FITC Binding to Human Pancreatic Stellate Cells

PSCs were trypsinized using trypsin-EDTA solution and cell numbers were diluted to $4 \times 10^4$ cells/ml. Cells were incubated at 37° C. for 30 minutes to allow receptor recovery. Then different concentrations of AXI-I-FITC was added to the cells containing 2% FBS and incubated at 4° C. for 60 minutes. Thereafter, cells were centrifuged at 1500 rpm at 4° C. for 10 minutes. Supernatant was removed and cells were washed 3 times with PBS and then were fixed with 0.5% formaldehyde for 1 hour at 4° C. and measured with flow cytometry for fluorescence.

Results

ITGA11 Expression in Hepatic Stellate Cells and Liver Fibrosis

Figure 1:
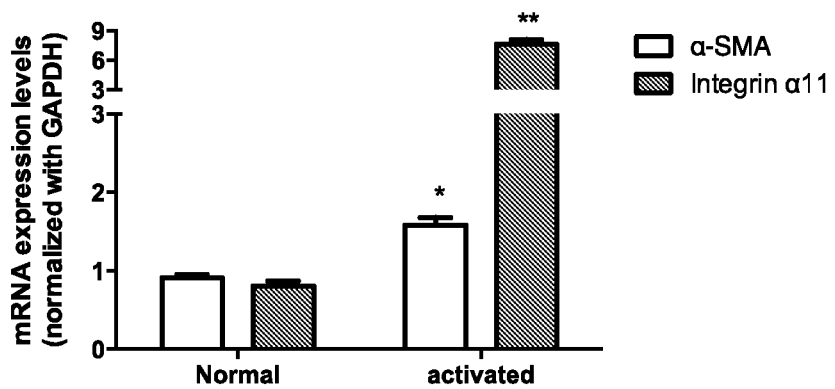
FIG. 1: Gene expression levels of α-SMA and integrin α11 in human hepatic stellate cells (Panel A) activated with TGF-β1 and in livers isolated at different stage of liver fibrosis in CCl4-induced liver fibrosis mouse models (Panel B). *p<0.05, **p<0.01 vs. normal.
Figure 1:
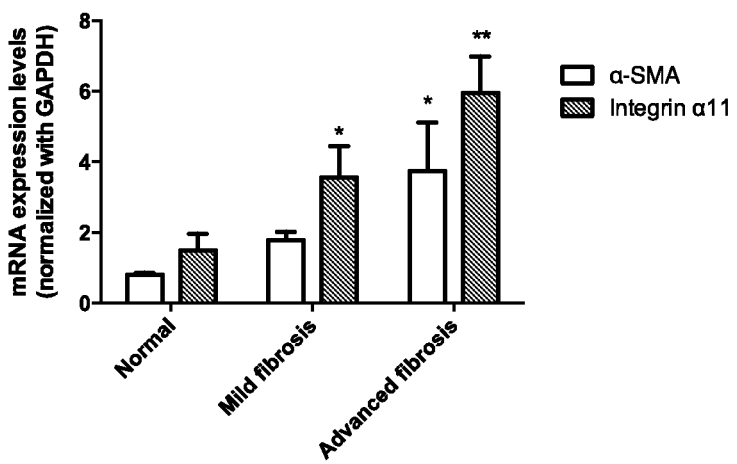

The expression of ITGA11 in hepatic stellate cells was investigated, which are the most important cell type in liver fibrosis, responsible for producing extracellular matrix. It was found that activation of stellate cells with TGFβ1 led to a significant increase in ITGA11 gene expression (FIG. 1, Panel A). These data corroborated with the increase in the expression level of the stellate cell activation marker α-SMA. Furthermore, the ITGA11 expression in CCl4-induced liver fibrosis model in mice was investigated. It was found that the expression level of ITGA11 significantly enhanced with the progression of fibrosis after the treatment of CCl4 for 4 weeks (mild fibrosis) and 8 weeks (advanced fibrosis) (FIG. 1, Panel B). This data indicates that ITGA11 is an important biomarker for liver fibrosis. Detection of ITGA11 using imaging techniques such as MRI, SPECT, PET, CT, photoacoustics or other kind of techniques with the help of a ligand against ITGA11 labeled with a radioisotope or a contrast agent can be applied for the diagnosis of liver fibrosis and to determine the progression of liver fibrosis.

Figure 2A:
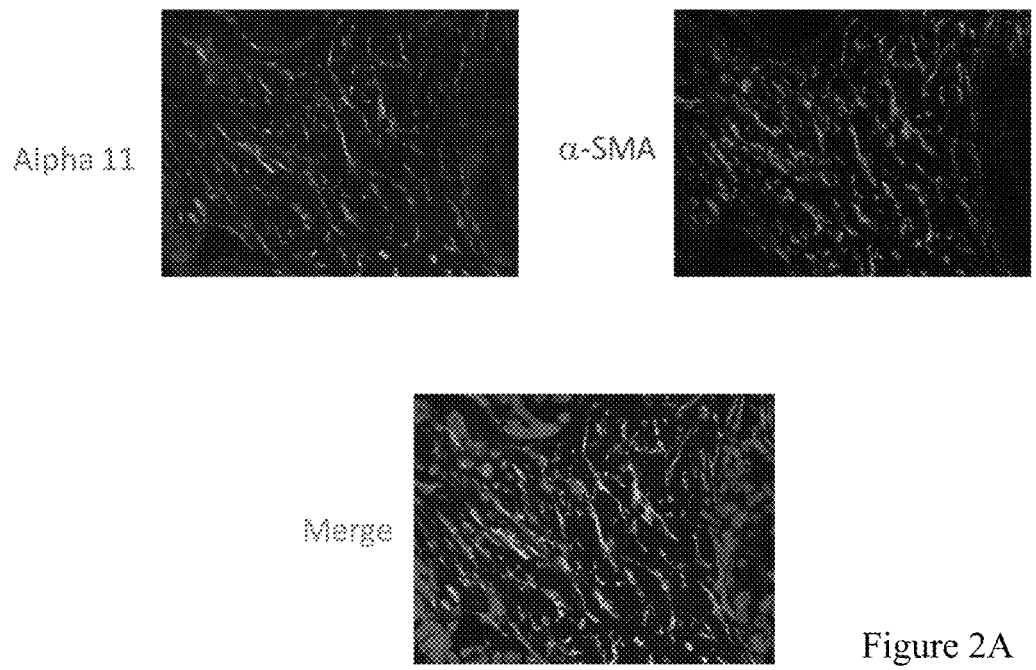
FIGS. 2A-2C.
Figure 2B:
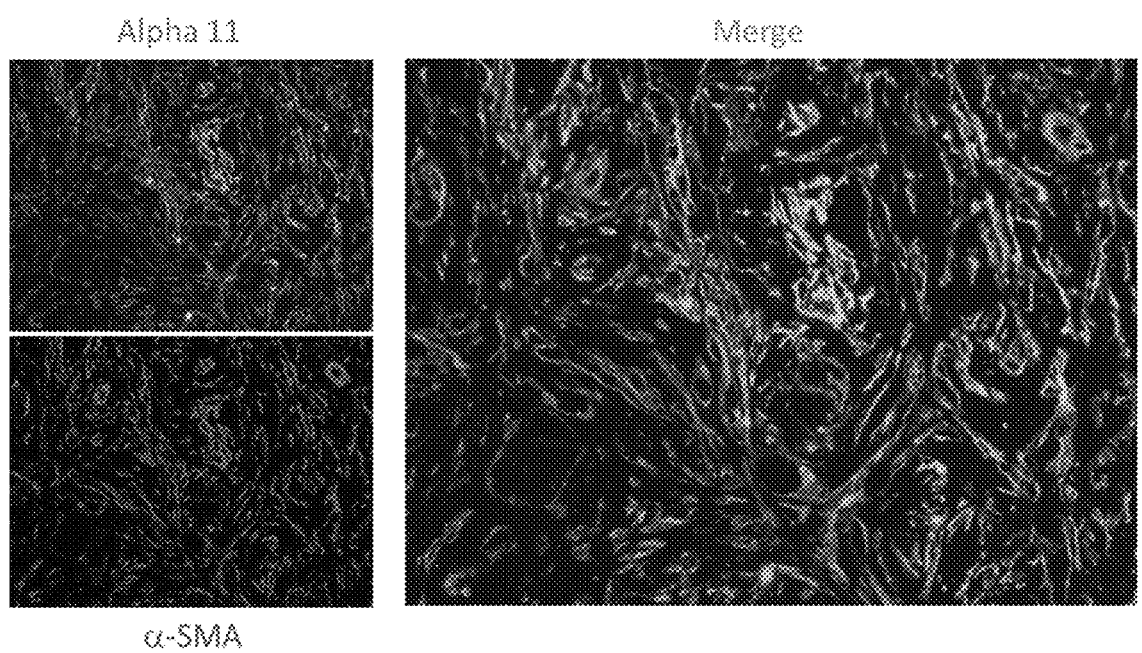
Figure 2C:
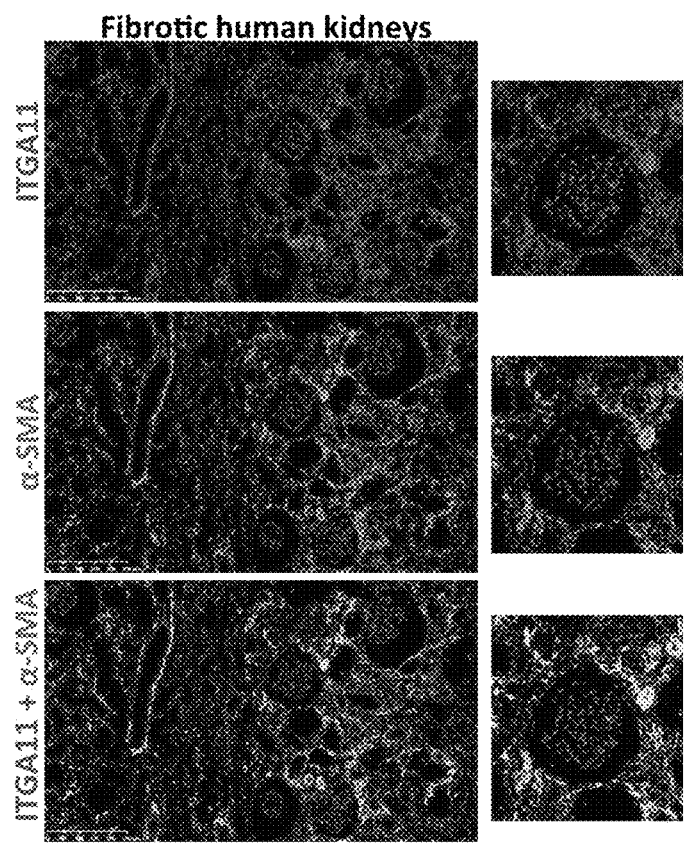

The expression of ITGA11 in different pathological conditions of human was determined. It was found that ITGA11 is strongly expressed in the fibrotic region of all examined pathological conditions such as liver cirrhosis, pancreatic tumor stroma and kidney fibrosis (FIGS. 2A-2C). The ITGA11 staining was well co-localized with the fibroblast marker α-SMA, as shown with orange-yellow color of the merge images.

Figure 3:
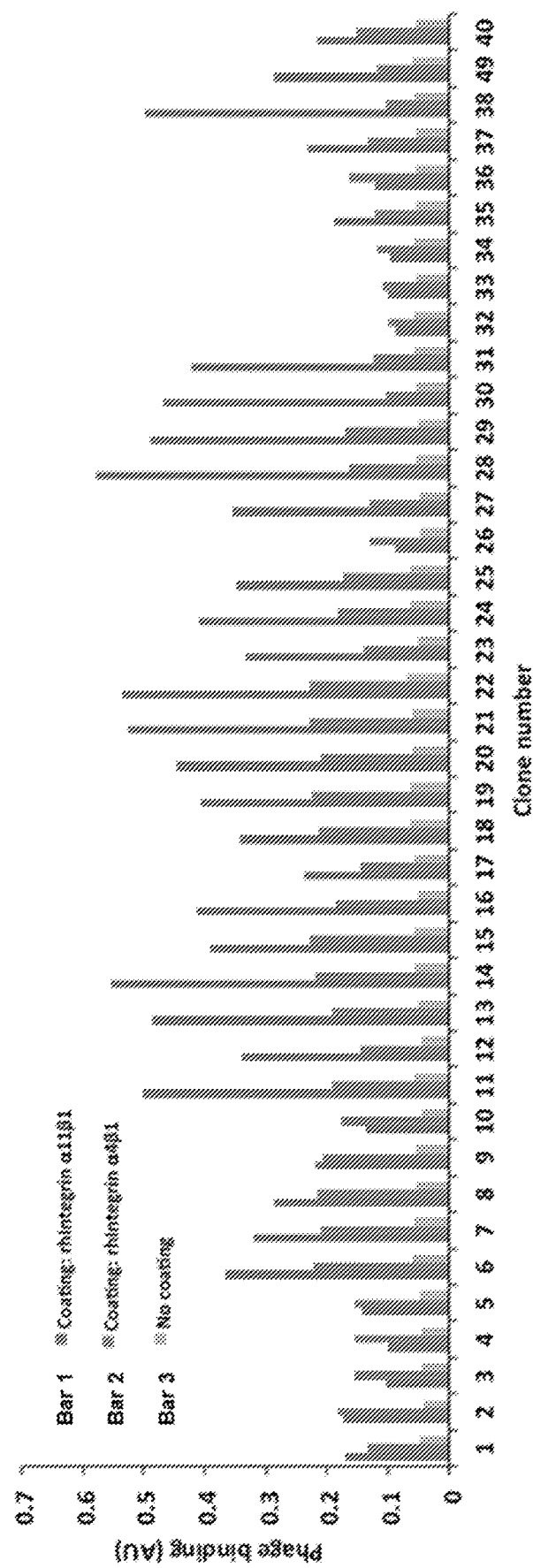
FIG. 3: Phage ELISA assay showing the binding of phages to α11β1 versus α4β1.

Phage-Display Selected Peptides:

The phage bound to the α11β1 receptor after subtracting from α4β1 receptor were eluted and amplified. Randomly 40 clones were picked and examined for binding to α11β1 and α4β1 receptors using Phage ELISA assay (FIG. 3). Clones number clones number 11, 13, 14, 16, 19, 20, 21, 22, 24, 25, 27, 28, 29, 30, 31 and 38 showed higher binding to α11β1 compared to α4β1 and non-coated well. DNA sequencing data showed that clones number 11, 13, 14, 16, 19, 20, 21, 22, 24, 25, 28, 29, 30, 31, and 38 resulted into a single sequence (5'-tctggtctgactgagtggttgaggtggtttaattcg-3') or amino acid sequence (AXI-I: SGLTEWLRWFNS (SEQ ID NO:1)) while clone 27 resulted into the DNA sequence (5' agttttgcgacgtggactccgaattttgagaggaat-3') or amino acid sequence (AXI-IL: SFATWTPNFERN (SEQ ID NO:2)).

Peptide Binding to ITGA11

Figure 4:
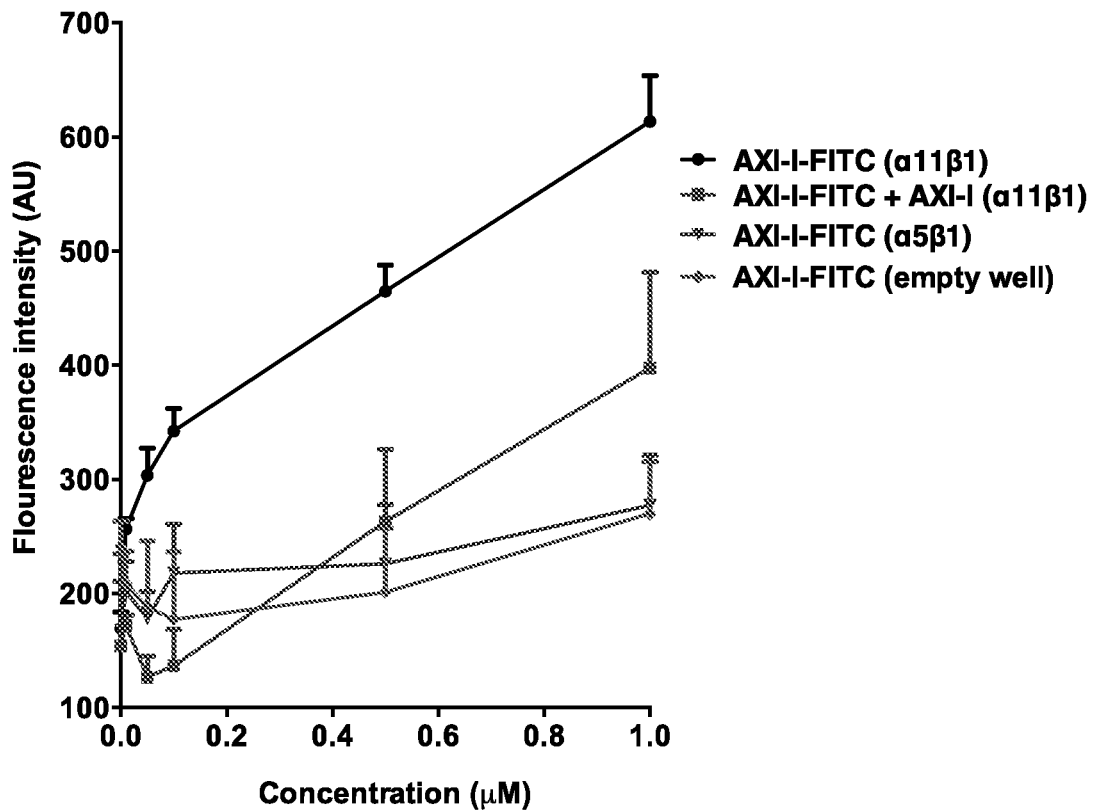
FIG. 4: Binding of the peptide to ITGA11. Panel A, showing the binding of AXI-I-PEG-FITC to the coated α11β1 receptor. AXI-I-FITC bound to the receptor with increasing concentration and the binding was blocked with excess of unlabeled AXI-I. Binding of the peptide to empty well or irrelevant receptor α5β1 led to no specific binding. Panels B and C, showing the binding of the AXI-I-FITC (Panel B) and AXI-II-FITC (Panel C) peptides to LX2 hepatic stellate cells as shown with green color.
Figure 4:
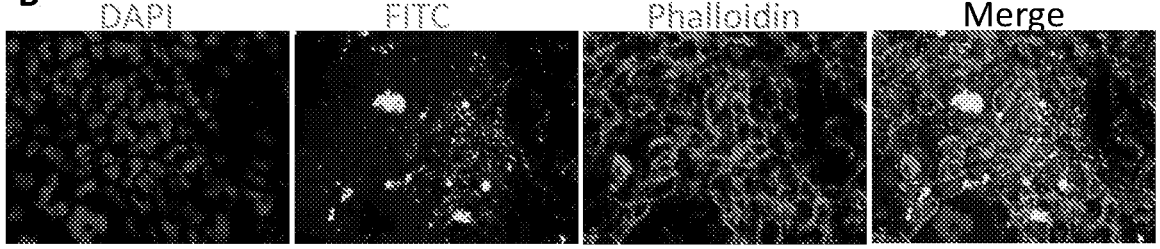
Figure 4:
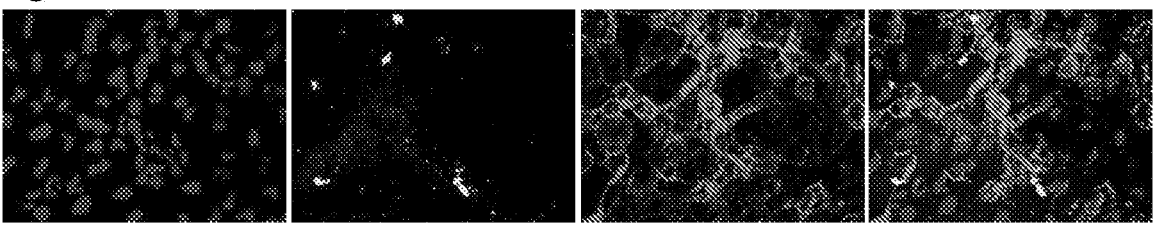

To determine whether peptides bind to ITGA11 receptor specifically, binding of FITC-labeled AXI-I peptide to the immobilized human ITGA11 (α11β1) receptor was performed. It was found that AXI-I-FITC bound to the ITGA11 receptor specifically, as the binding was blocked by 10-fold excess unlabeled peptide (FIG. 4, Panel A). In addition, the peptide showed very low binding to another integrin receptor (i.e., α5β1), which was similar to the binding to the empty wells. The β1 receptor is a common co-receptor in both α11β1 and α5β1 and no binding of the peptide to α5β1 but high binding to α11β1 indicates that the peptide is preferably bound by α11. Furthermore, the binding of AXI-I on mouse α11β1 receptor was examined and found that the peptide has similar binding affinity as for human, which attributes to about 80% homology between mouse and human ITGA11 receptors. After confirming the binding to the immobilized receptor, the binding of the peptides on the ITGA11-expressing hepatic stellate cells was examined. It was found that both AXI-I and AXI-II bound to the stellate cells but binding of AXI-I was clearly stronger than AXI-II (FIG. 4, Panel B).

Figure 5:
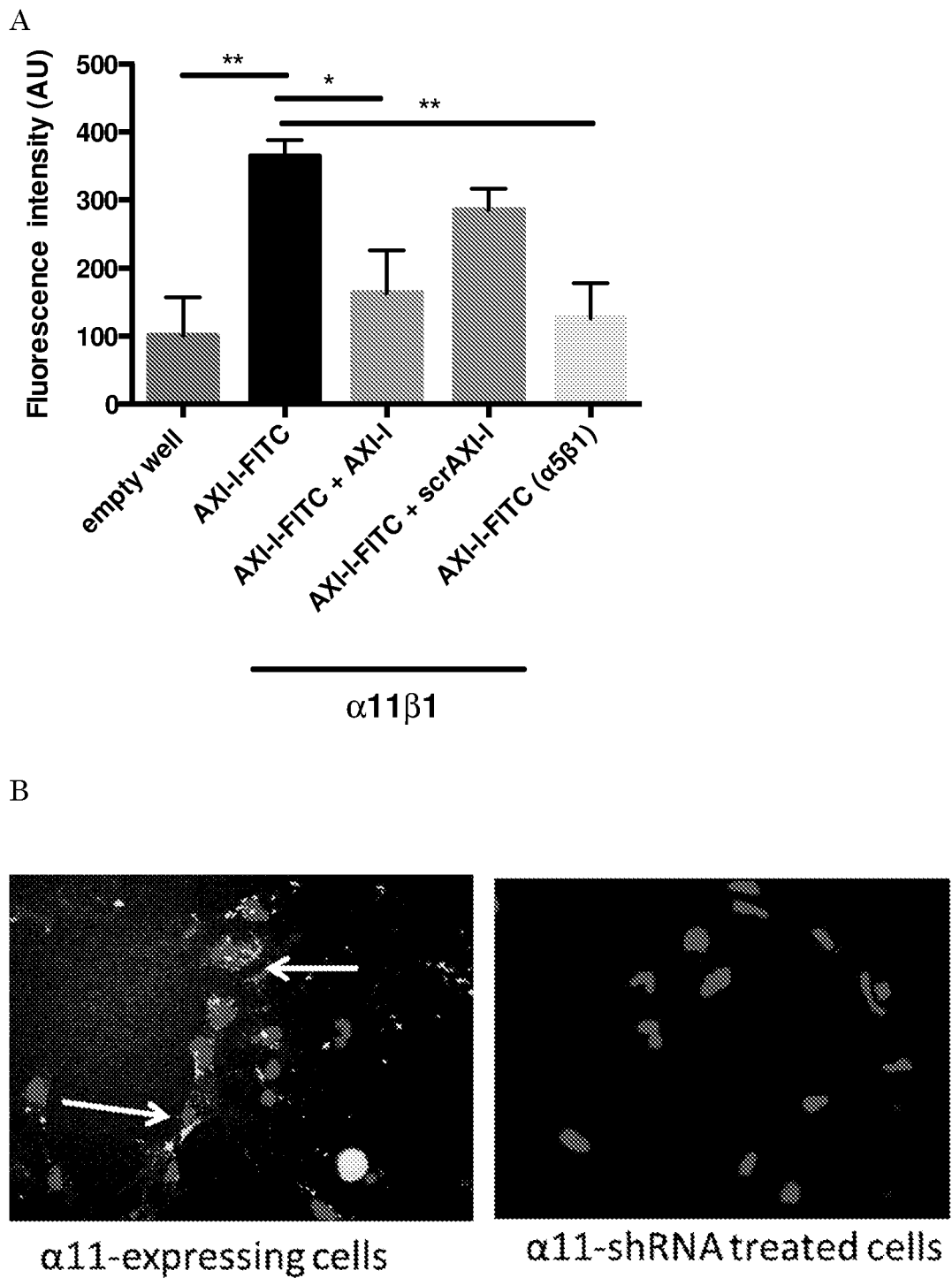
FIG. 5: Binding studies of ITGA11-binding peptide (AXI-I) labeled with FITC on the coated α11β1 receptor (Panel A) and on the LX2 cells (Panel B). On the receptor, binding was competitively blocked by adding 10-fold high concentration of unlabeled peptide. The receptor binding data is an average of n=4 independent experiments, each in duplicate. Mean+ sem. Knockdown of ITGA11 in LX2 led to complete inhibition of the peptide binding.

Binding studies of ITGA11-binding peptide (AXI-I) labeled with FITC on the coated α11β1 receptor showed that the peptide bound to the receptor specifically compared to the empty well. The binding was competitively blocked by adding 10-fold high concentration of unlabeled peptide, showing specific binding of the peptide (FIG. 5, Panel A). The binding of the peptide to the ITGA11 expressing LX2 cells was confirmed using fluorescent microscopy. Knockdown of ITGA11 using shRNA-ITGA11 in these cells led to complete inhibition of the peptide binding, as no fluorescent signal was detected (FIG. 5, Panel B).

Alanine Scanning and Peptide Chain Length Scan

Figure 7:
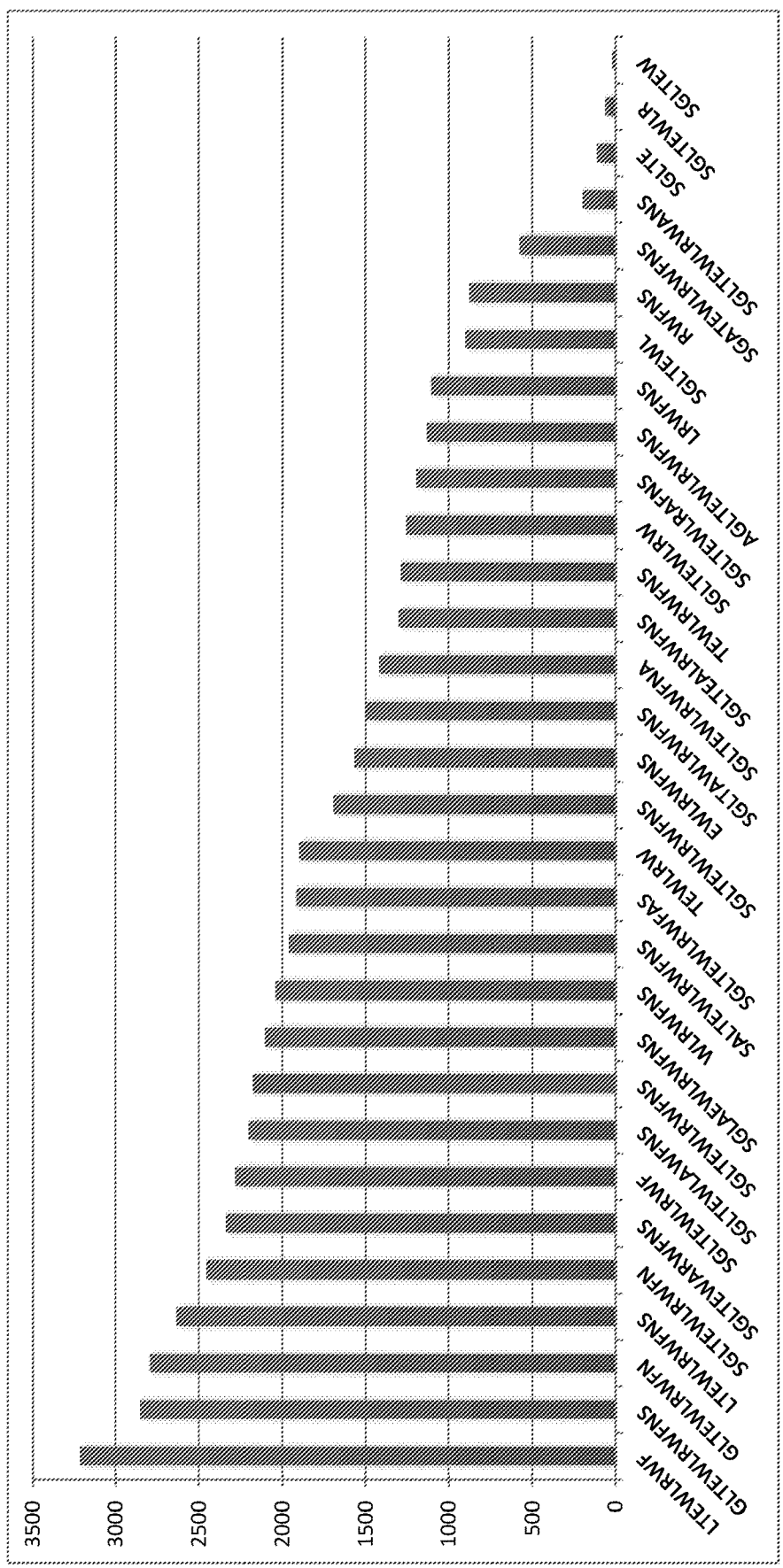
FIG. 7: Alanine scanning and peptide chain length scan for AXI-I peptide (SGLTEWLRWFNS (SEQ ID NO: 1)), and, along the x-axis, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:5, SEQ ID NO:1, SEQ ID NO:71, SEQ ID NO:73, SEQ ID NO:74, and SEQ ID NO:75.

To find out the amino acids responsible for the peptide binding and the most efficient binding peptides, peptide microarrays were developed with alanine replacement and shorter peptides for AXI-I peptide (SGLTEWLRWFNS (SEQ ID NO:1)) (FIG. 7).

For AXI-I peptide (SGLTEWLRWFNS (SEQ ID NO:1)), replacement of L3 or F10 led to remarkable decrease of the peptide binding to the α11β1 receptor, indicating that these amino acids make the epitopes. The shortening of the peptide chain showed that LTEWLRWF peptide induced the strongest binding to the receptor. As a control, the peptide array was exposed to α5β1 to check the unspecific binding of the LTEWLRWF peptide. Table 1 shows the sequences of ITGA11 binding peptides.

TABLE 1

Sequence of ITGA11 binding peptides

|    | 1 | 2 | 3 | 4 | 5 | 6 | 7 | 8 | 9 | 10 | 11 | 12 | SEQ ID NO: |
|----|---|---|---|---|---|---|---|---|---|----|----|----|-----------|
|    | S | G | L | T | E | W | L | R | W | F  | N  | S  | 1 |
| 1  |   |   | L | T | E | W | L | R | W | F  |    |    | 24 |
| 2  |   | G | L | T | E | W | L | R | W | F  | N  | S  | 25 |
| 3  |   | G | L | T | E | W | L | R | W | F  | N  |    | 26 |
| 4  |   |   | L | T | E | W | L | R | W | F  | N  | S  | 27 |
| 5  | S | G | L | T | E | W | L | R | W | F  | N  |    | 28 |
| 6  | S | G | L | T | E | W | A | R | W | F  | N  | S  | 29 |
| 7  | S | G | L | T | E | W | L | R | W | F  |    |    | 30 |
| 8  | S | G | L | T | E | W | L | A | W | F  | N  | S  | 31 |
| 9  | S | G | L | T | E | W | L | R |   | F  | N  | S  | 32 |
| 10 | S | G | L | A | E | W | L | R | W | F  | N  | S  | 33 |
| 11 |   |   |   |   |   | W | L | R | W | F  | N  | S  | 34 |
| 12 | S | A | L | T | E | W | L | R | W | F  | N  | S  | 35 |
| 13 | S | G | L | T | E | W | L | R | W | F  | A  | S  | 36 |
| 14 |   |   |   | T | E | W | L | R | W |    |    |    | 37 |
| 15 | S | G | L | T | E | W | L | R | W | F  | N  | S  | 38 |
| 16 |   |   |   |   | E | W | L | R | W | F  | N  | S  | 39 |
| 17 | S | G | L | T | A | W | L | R | W | F  | N  | S  | 40 |
| 18 | S | G | L | T | E | W | L | R | W | F  | N  | A  | 41 |
| 19 | S | G | L | T | E | A | L | R | W | F  | N  | S  | 42 |
| 20 |   |   |   | T | E | W | L | R | W | F  | N  |    | 43 |
| 21 | S | G | L | T | E | W | L | R | W |    |    |    | 44 |
| 22 | S | G | L | T | E | W | L | R | A | F  | N  | S  | 45 |
| 23 | A | G | L | T | E | W | L | R | W | F  | N  | S  | 46 |
| 24 |   |   |   |   |   |   | L | R | W | F  | N  | S  | 47 |

AXI-PEG FITC Binding to Human Pancreatic Stellate Cells

Figure 6:
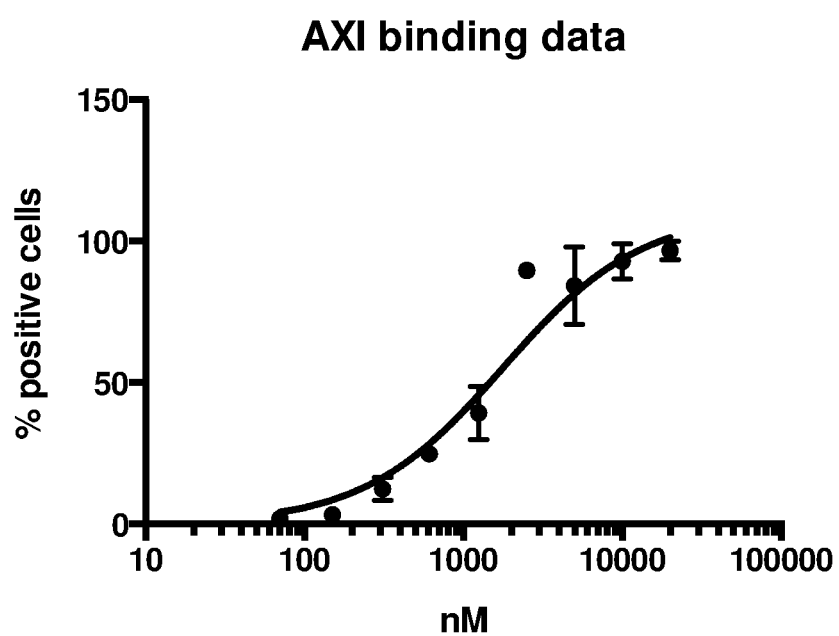
FIG. 6: AXI-I-PEG-FITC binding assay-flow cytometry in primary human pancreatic stellate cells. Different concentrations of AXI-I-PEG-FITC was incubated with suspended pancreatic stellate cells for 1 hour at 4° C., washed and fixed with 0.5% formaldehyde and measured with flow cytometry. The results show that AXI-I-PEG-FITC bound to these cells concentration dependently leading to dissociation constant (kd) value of approximately 1 μM.

Different concentrations of AXI-I-PEG-FITC was incubated with suspended PSCs for 1 hour at 4° C., washed and fixed with 0.5% formaldehyde and measured with flow cytometry. The results demonstrate that binding of AXI-I-PEG-FITC to PSCs increased with the increasing concentration and reached to plateau at 20 μt concentration (FIG. 6). The 5000 of the total binding, i.e., dissociation constant (kd) value was approximately 1 uM. Since the peptide has been modified with PEG chain and a fluorophore, the binding affinity of the peptide may be reduced due to steric hindrance.

Effect of AXI-I Peptide In Vitro on LX2 Cells and in CCl4-Induced Liver Fibrosis Model in Mice The Inhibitory Effect of AXI-I Peptide in LX2 Cells was Examined. Activation of LX2 cells with TGFβ1 induced the expression of collagen-1. Interestingly, treatment with increasing concentrations of AXI-I inhibited the expression of collagen-I (FIG. 8, Panel A). In contrast, the scrambled peptide showed no reduction in the collagen staining.

Furthermore, the effect of AXI-I in a CCl4-induced liver fibrosis model in mice was examined. It was found that treatment with AXI-I at the dose of 200 ug/kg/d i.p. led to reduction of fibrogenesis, as indicated by the decrease of gene expression of ITGA5 and ITGA11, markers of myofibroblasts and protein expression of collagen-I and III in livers compared to vehicle control (FIG. 8, Panel B). These data indicate that AXI-I possesses anti-fibrotic properties, which need to be optimized at different doses.

Example 2

Materials and Methods

ITGA5 Peptide Selection

Figure 11:
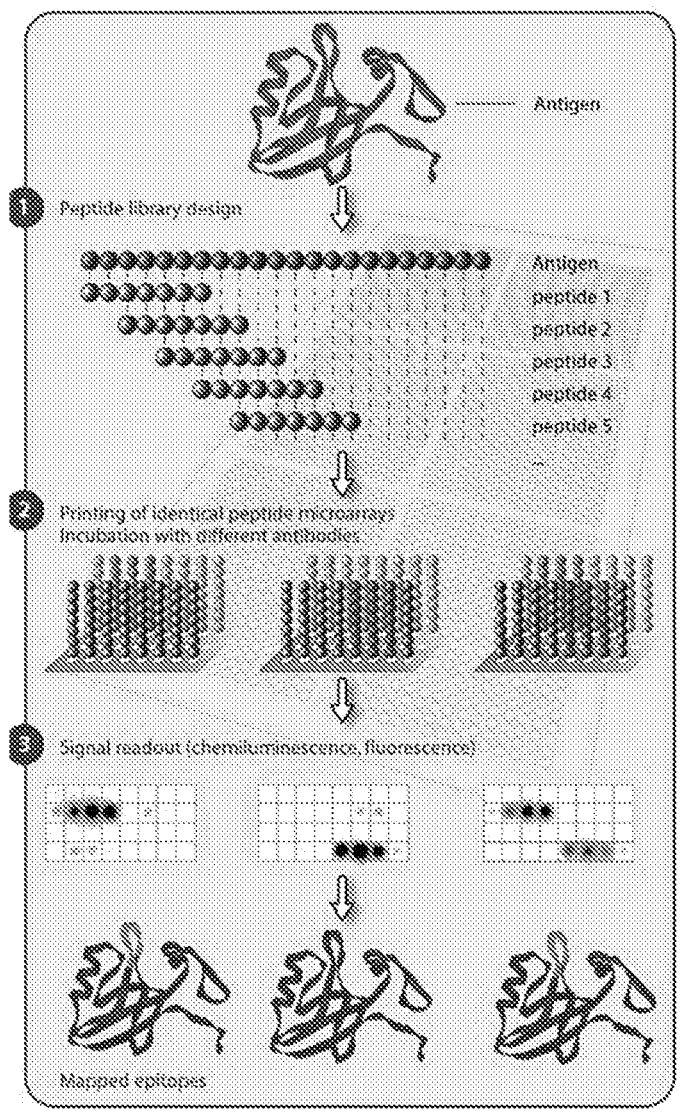
FIG. 11: Design of peptide against ITGA5. Image derived from "Protocol Multiwell Peptide Microarrays" of JPT Technologies, Berlin Germany, https://www.jpt.com/fileadmin/Multiwell-Peptide-Microarray_Protocol_Rev_1.0_V06.pdf.

To select the peptidomimetic binding to ITGA5, 12 amino acid overlapping peptides (8 overlap) from the sequence from human fibronectin-III domain 9-10 (Uniprot nr. P02751) were displayed on a cellular membrane as dots (FIG. 11). Peptides were attached to their c-terminal site using stable linker. The cysteine was exchanged with serine to enhance the stability and also because cysteine generally does not make an epitope. The peptide-displaying cellular membrane was soaked in methanol for 1 minute and rinsed in Tris-buffered saline (TBS) and washed 3 times. Then, the membrane was blocked with 3% BSA in 0.05% TWEEN®-20 containing TBS (TBST) for 3 hours at room temperature. Then, the membrane was washed for 10 minutes with TBST and incubated with 5 μg/ml α5β1 human recombinant protein (R&D systems) in 3% BSA in TBST for 1 hour at room temperature and then overnight at 4° C. Subsequently, the membrane was washed 3 times with TBST. Thereafter, the bound receptor to the membrane was transferred to the PVDF membrane. To achieve this, first, the PVDF membrane was soaked in methanol for 1 minute and then blocked with 5% skimmed fat milk for 2 hours. Then, the membrane was incubated with primary anti-alpha5 integrin antibody (Sigma-Aldrich) for overnight in 5% skimmed milk. The membrane was washed 3 times with TBST and then incubated with anti-rabbit-HRP secondary antibody (Dako), washed and developed with chemiluminescence detection kit.

The following sequences from the fibronectin were used for developing overlapping peptides.

```
Human FNIII-9 (Uniprot nr. P02751)
                              (SEQ ID NO: 48)
GLDSPTGIDFSDITANSFTVHWIAPRATITGYRIRHHPEHFSGRPREDRV
PHSRNSITLT NLTPGTEYVVSIVALNGREESPLLIGQQST Mouse FNIII-9 (P11276)
                              (SEQ ID NO: 49)
AVPPPTDLRFTNIGPDTMRVTWAPPPSIELTNLLVRYSPVKNEEDVAELS
ISPSDNAVVLTNLLPGTEYLVSVSSVYEQHESIPLRGRQKT Partial Human FNIII-10 seq.
                              (SEQ ID NO: 50)
TVRYYRITYGETGGNSPVQEFTVPGSKSTATISGLKPGVDYTITVYAVTG
RGDSPASSKPISI
```

Peptide Binding Study on the Coated Receptor

The purified human recombinant α5β1 or α11β1 receptors (5 μg/ml in PBS) were coated onto 96-well ELISA plates (White Maxisorb-Nunc) by incubating overnight at 4° C. Then, the wells were blocked with blocking buffer (5% (w/v) BSA, 150 mM Nacl, 25 mM Tris) for 2 hours at room temperature. Then, the wells were washed three times with 200 μl of washing buffer (150 mM Nacl, 25 mM Tris-base, 0.005% TWEEN® 20, 0.5% BSA). Thereafter, the peptides conjugated with PEG(6)-FITC were diluted to different concentrations in washing buffer. For the competitive studies, the wells were co-incubated with 10-fold higher amount of unlabeled peptides. The plates were incubated at 37° C. for 60 minutes. Then, the wells were washed three times with washing buffer and subsequently, the plates were read for the fluorescein signal Ex/Em 485 nm/520 nm using a fluorescent plate reader (Perkin Elmer).

Binding Studies on Peptide Microarray

Peptide microarray was prepared by conjugating peptides at their N-terminal to a glass slide using a PEG linker. Each peptide was displayed three times at different positions to avoid artefacts and errors. For the binding studies, the peptide array was blocked with 3% BSA in TBST for 2 hours. Then the array slide was washed 5 times in TBST and subsequently incubated with the target receptor (α5β1, 10 μg/ml dissolved in PBS) for 1 hour at 37° C. The slides were washed with TBST and then incubated with primary antibody (1 μg/ml) against ITGA5 for 1 hour at 37° C. Then slides were washed and incubated with fluorescent dye labeled secondary antibodies for 30 minutes. The slides were washed with TBST and water and then dried and scanned with a microarray scanner to detect binding of the peptides. The enlightened spots were analyzed using ImageJ software. To determine the unspecific binding, a peptide array was incubated with only primary and secondary antibodies without the receptor incubation step. Then, the signal of unspecific binding was subtracted from the total binding to calculate specific binding.

Effect Studies

Human primary pancreatic stellate cells (PSCs) were obtained from ScienCell (Carlsbad, Calif.) and were cultured in specified medium provided by the manufacturer, supplemented with penicillin/streptomycin. Cells were used less than the passage 9 and seeded on a Poly-L-Lysine-coated plate.

PSCs were seeded into a 12-well plate ($6 \times 10^4$ cells/well, for gene expression) or 24-well plate (for staining) in complete medium. After 24 hours, cells were starved in serum-free medium and then after 24 hours, they were added with TGF-β1 (5 ng/ml) with/without the peptide.

After 24 hours of incubation, cells were lysed with the lysis buffer and total RNA was isolated using the Gen-Elute™ Mammalian Total RNA Miniprep Kit. The RNA amount was measured by a NanoDrop® ND-1000 Spectrophotometer (Wilmington, Del.). Subsequently, cDNA was synthesized with iScript™ cDNA Synthesis Kit (BioRad, Veenendaal, The Netherlands). 10 ng cDNA was used for each PCR reaction. The real-time qPCR primers for human αSMA and RPS18 were purchased from Sigma (The Netherlands). Gene expression levels were normalized to the expression of the house-keeping gene RPS18s.

For immunostaining, the cells were washed and fixed with acetone-methanol and processed for immunocytochemical staining.

Immunohistochemical Staining

Human pancreatic specimens, human liver cirrhosis and kidney fibrosis specimen were obtained from the Department of Pathology, Laboratory Pathology East Netherlands (LabPON), Enschede, The Netherlands. Ethical approvals were obtained from the local Medical Ethical Committee at LabPON. Samples were cut into 2 μm thick sections using a microtome (Leica Microsystems, Nussloch, Germany). The sections were processed for deparaffinization and then incubated at 80° C. overnight in Dako antigen retrieval buffer to expose antigens. The endogenous peroxidase activity was blocked by 3% $H_2O_2$ prepared in methanol. Sections were then washed with PBS and incubated with the primary antibody (anti-ITGA11, anti-ITGA5 or anti-SMA or anti-CD31) for 1 hour at room temperature. Sections were then incubated with horseradish peroxidase (HRP)-conjugated secondary antibody for 1 hour at room temperature. Then incubated with Alexa488 or Alexa594-conjugated tertiary antibody for 1 hour, after which these were washed thrice with 1×PBS. Nuclei were counterstained with DAPI containing mounting medium (Sigma).

For immunocytostaining, cells were fixed with acetone-methanol (1:1) at −20° C. for 30 minutes and then dried and rehydrated for 10 minutes. Cells were then incubated with primary antibodies for 1 hour and then with HRP-labeled secondary antibodies for 30 minutes. Thereafter, peroxidase activity was developed using AEC (3-amino-9-ethyl carbazole) substrate kit (Life Technologies, Gaithersburg, Md.) for 20 minutes and nuclei were counterstained with hematoxyllin (Fluka Chemie, Buchs, Switzerland). Cells were mounted with Aquatex mounting medium (Merck, Darmstadt, Germany). The staining was visualized and the images were captured using light microscopy (Nikon eclipse E600 microscope, Nikon, Tokyo, Japan).

Results

Selection of ITGA5 Binding Peptides

ITGA5, integrin alpha5, is a known receptor for fibronectin (FN) and to select a peptide ligand against ITGA5, overlapping sequences (12 aa. long with 8 aa. overlaps) from human FN-III domains-9 and 10 were designed and displayed on a cellular membrane. The domains 9 and 10 of FN were chosen to design peptides, as these domains were reported to be responsible for binding to the α5β1 receptor, as shown with the docking experiments (Nagae et al, 2012 J. Cell Biol. 131-140). The interaction studies were performed against human recombinant integrin α5β1 receptor and the bound proteins were transferred to another membrane and ITGA5 was detected with antibodies. Many sequences appeared to bind to the α5β1 receptor from human and mouse domains, the strongest binding was obtained with 2 sequences from human FN-III domain 10 as follows.

```
From human FN-III domain 9
                                                    Seq 1.
ITANSFTVHWIA-weak Seq 2.
VALNGREESPLL-very weak From human FN-III domain 10
                                                    Seq 3.
TTVRYYRITYGE-strong Seq 4.
YYRITYGETGGN-very strong Seq 5.
GDSPASSKPISI-moderate From mouse FN-III domain 9
                                                    Seq 6.
SIELTNLLVRYS-moderate Seq 7.
TNLLVRYSPVKN-moderate
```

Since YYRITYGETGGN (SEQ ID NO:56) sequence provided the strongest signal, this sequence was further chemically synthesized and then PEG(6)-Fluorescein was introduced at the N-terminal side of the peptide for its detection during the peptide-binding assays to the coated α5β1 receptor. Surprisingly, however, no binding was observed to the coated receptor. In the peptide array on the cellular membrane, the peptides were conjugated through the C-terminal, while the N-terminal of the peptides was free to bind to the receptor. However, in the synthetic peptide PEG was conjugated to the N-terminal, which might have blocked the binding of the peptide. Therefore, a new peptide (nAV2) was synthesized in which the PEG(6)-fluorescein was conjugated to the C-terminal by introducing a lysine group to allow PEG conjugation.

Figure 12:
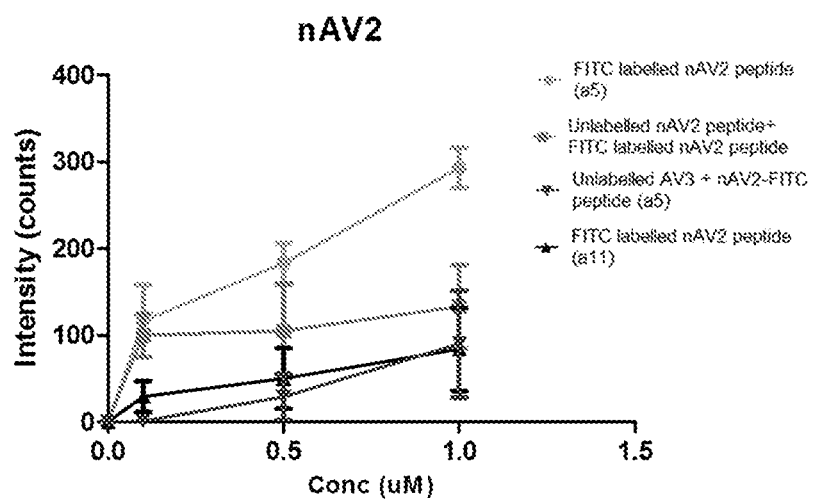
FIG. 12: Binding of peptides to the coated α5β1 receptor and LX2 cells. FITC-labeled nAV2: YYRITYGETGGN (SEQ ID NO:56)-K-PEG(6)-Fluorescein; nAV2: YYRITY-GETGGN (SEQ ID NO:56); AV3: RYYRITY (SEQ ID NO:8). Panel A, nAV2-FITC bound to the coated α5β1 receptor that was blocked by excess of nAV2 peptide and much stronger with excess of AV3 peptide. Panel B, showing the binding of nAV2-FITC to LX2 cells (stained with DAPI), as shown in green color (FITC).
Figure 12:
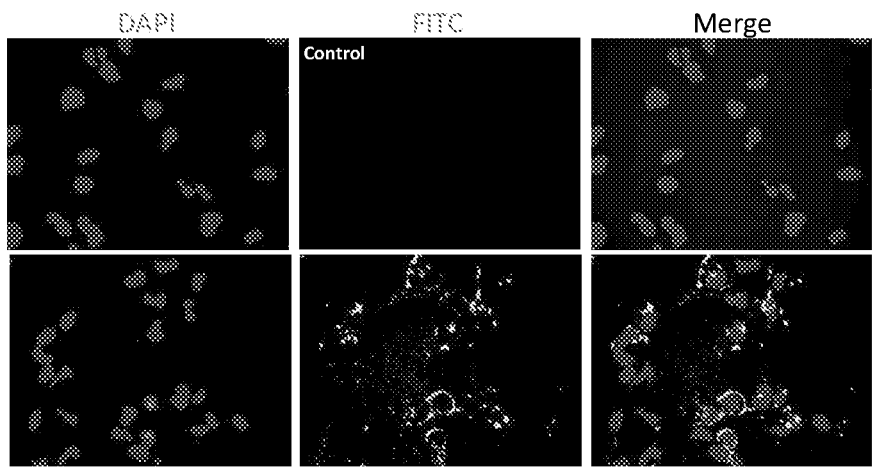

Interestingly, nAV2 showed a good binding to the coated receptor (FIG. 12, Panel A). Blocking of the peptide with 10-fold excess of unlabeled peptide blocked the binding of nAV2-PEG(6)-fluorescein. In addition, a new short peptide (RYYRITY (SEQ ID NO:8), called AV3) was also designed because seq. 3 and seq. 4 (see the sequences above) had "YYRITY" (SEQ ID NO:10) as common amino acids and the N-terminal of the seq. 4 was crucial for the binding to the receptor. Addition of the excess of AV3 to nAV2-PEG-fluorescein strongly blocked its binding to the receptor, indicating that AV3 has higher affinity to the receptor. Therefore, AV3 was selected to move with further studies. Furthermore, binding of nAV2-FITC to LX2 cells was performed and found that the peptide clearly bound to these cells compared to control cells (FIG. 12, Panel B).

Alanine Scanning and Peptide Chain Length Scan

Figure 13:
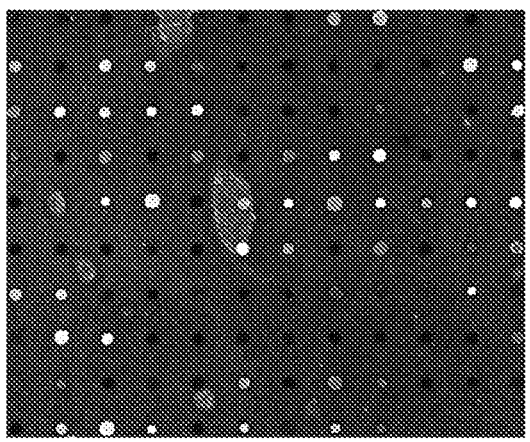
FIG. 13: Alanine replacement assay of peptide RYYRUTY (from top to bottom, SEQ ID:NO:8, SEQ ID NO:61, SEQ ID NO:62, substituted SEQ ID NO:8, SEQ ID NO:63, SEQ ID NO:64, SEQ ID NO:76, and SEQ ID NO:65) to find essential amino acids. Bold and underlined amino acids seem important for binding, in particular Y3 and T6.

To find out the amino acids responsible for the peptide binding and the most efficient binding peptides, peptide microarrays were developed with alanine replacement and shorter peptides. In addition a peptide having the sequence RYYRITYC (SEQ ID NO:11) (AV3-Cys) was developed. For AV3 (RYYRITY (SEQ ID NO:8)), the peptide microarray was incubated with α5β1 receptor, which was captured by anti-α5 and then fluorescent dye labeled secondary antibody. The binding results show that replacement of Y3 led to loss of binding while replacement of R1, R4, and Y7 led to decrease in binding of AV3 peptide. Replacement of T6 induced unspecific binding of the peptide to the incubating antibodies (FIG. 13). Table 2 shows the sequences of ITGA5 binding peptides.

TABLE 2

Sequence of ITGA5 binding peptides. (SEQ ID NO:, far right column).

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | SEQ ID NO: |
|---|---|---|---|---|---|---|---|---|----|----|----|----|----|----|----|----|----|----|----|----|----|---|
| T | T | V | R | Y | Y | R | I | T | Y | G | E | T | G | G | N | 17 | 18 | 19 | 20 | 21 | 22 | 3 |
| T | T | V | R | Y | Y | R | I | T | Y | G | E |   |   |   |   |   |   |   |   |   |   | 7 |
|   |   |   |   | Y | Y | R | I | T | Y | G | E | T | G | G | N |   |   |   |   |   |   | 56 |
|   |   |   | R | Y | Y | R | I | T | Y |   |   |   |   |   |   |   |   |   |   |   |   | 8 |
|   |   |   | A | Y | Y | R | I | T | Y |   |   |   |   |   |   |   |   |   |   |   |   | 61 |
|   |   |   | R | A | Y | R | I | T | Y |   |   |   |   |   |   |   |   |   |   |   |   | 62 |
|   |   |   | R | Y | Y | A | I | T | Y |   |   |   |   |   |   |   |   |   |   |   |   | 63 |
|   |   |   | R | Y | Y | R | A | T | Y |   |   |   |   |   |   |   |   |   |   |   |   | 64 |
|   |   |   | R | Y | Y | R | I | T | A |   |   |   |   |   |   |   |   |   |   |   |   | 65 |
|   |   |   | R | Y | Y | R | I | T | Y | C |   |   |   |   |   |   |   |   |   |   |   | 66 |

TABLE 2-continued

Sequence of ITGA5 binding peptides. (SEQ ID NO:, far right column).

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | SEQ ID NO: |
|---|---|---|---|---|---|---|---|---|---|---|---|---|---|---|---|---|---|---|---|---|---|---|
| T | T | V | R | Y | Y | R | I | T | Y | G | E | T | G | G | N |  |  |  |  |  |  | 3 |
|  |  |  |  | Y | Y | R | I | T | Y | G | E | T | G | G | N | K |  |  |  |  |  | 67 |
|  |  |  | R | Y | Y | R | I | T | Y | G | G | G | G | L | T | E | W | L | R | W | F | 68 |

Effect Studies Primary Pancreatic Stellate Cells (PSCs)

Figure 10:
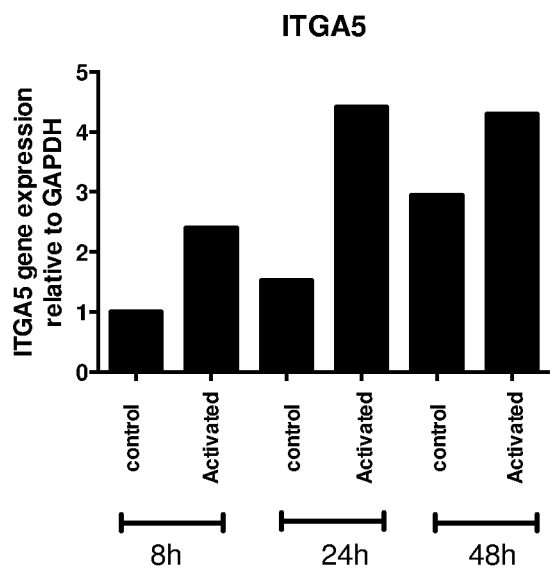
FIG. 10: ITGA5 expression in human skin fibroblasts and pancreatic stellate cells. Panel A, Human skin fibroblasts (BJhtert) expressed an increasing levels of ITGA5 after activation with TGF-β1 for 8, 24 and 48 hours. Panel B, Activation of pancreatic stellate cells with TGFβ or panc-1 tumor cell conditioned medium induced the ITGA5 expression levels after 24 hours.
Figure 10:
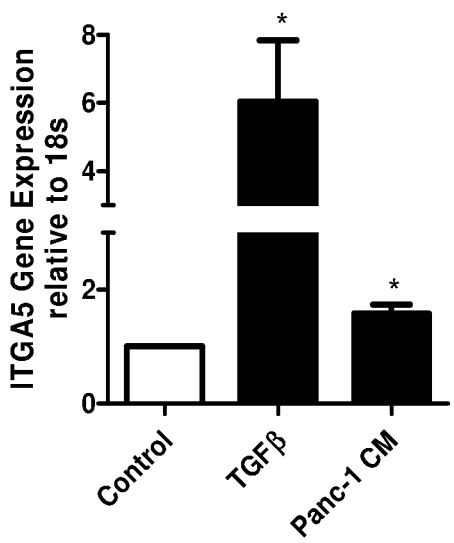

Activation of human skin fibroblasts (BJhtert) with TGFβ1 induced gene expression levels of ITGA5 at 8, 24 and 48 hours (FIG. 10). In addition, activation of pancreatic stellate cells with TGFβ or panc-1 tumor cell conditioned medium also induced the ITGA5 expression levels after 24 hours.

Effect Studies on Skin Fibroblasts and PSC

Activation of PSCs with TGFβ led to activation and differentiation of these cells to myofibroblasts, as indicated by the increased α-SMA expression. Interestingly, treatment with AV3 peptide significantly inhibited the α-SMA expression at 20 μM, showing the anti-fibrotic effects of AV3 peptide (FIG. 14, Panel A). In addition, incubation of PSCs with TGFβ1 enhanced the expression of fibrotic markers such as α-SMA, Col-1a1 and vimentin, as shown with immunohistochemical stainings. Treatment with AV3-cys peptide clearly inhibited the expression of these biomarkers, indicating that AV3-cys peptide is able to inhibit the activation and differentiation of PSCs. In contrast, scrambled AV3-cys did not show any inhibitory effects (FIG. 14, Panel B).

In addition, the effect of AV3 and its variants on the migration of human skin fibroblasts was examined. It was found that AV3-cys peptide significantly inhibited the migration of fibroblasts while its scrambled version did not show any effect (FIG. 15, Panel A). Furthermore, different peptide versions were tested for their effect on the migration of the fibroblasts. Only AV3.3 showed about 30% reduction on migration while other versions showed slight or no effects (FIG. 15, Panel B).

Immunohistochemical Staining of Human Pancreatic Specimens

Figure 9:
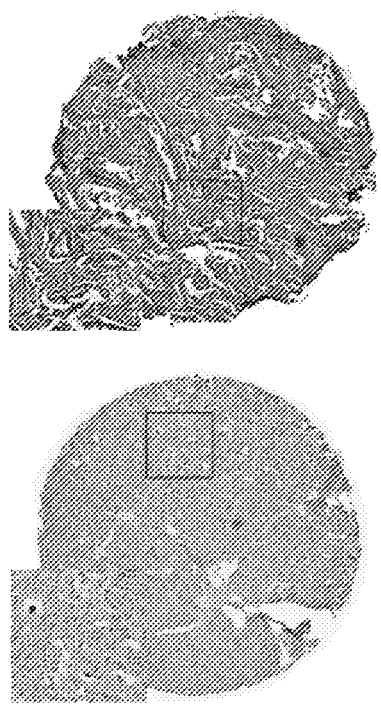
FIG. 9: ITGA5 in pancreatic cancer. Panel A, Left image shows the immunostaining of ITGA5 in normal human pancreas while right image shows the staining in pancreatic tumor. Pancreatic tumor shows a strong staining of ITGA5 while normal pancreas shows no staining. Panel B, Co-localization of ITGA5 with a-SMA (marker for myofibroblasts) and CD31 stainings (marker for endothelial cells). Double staining shows that ITGA5 perfectly coincide with α-SMA but slightly with CD31, indicating that ITGA5 is highly expressed on myofibroblasts.
Figure 9:
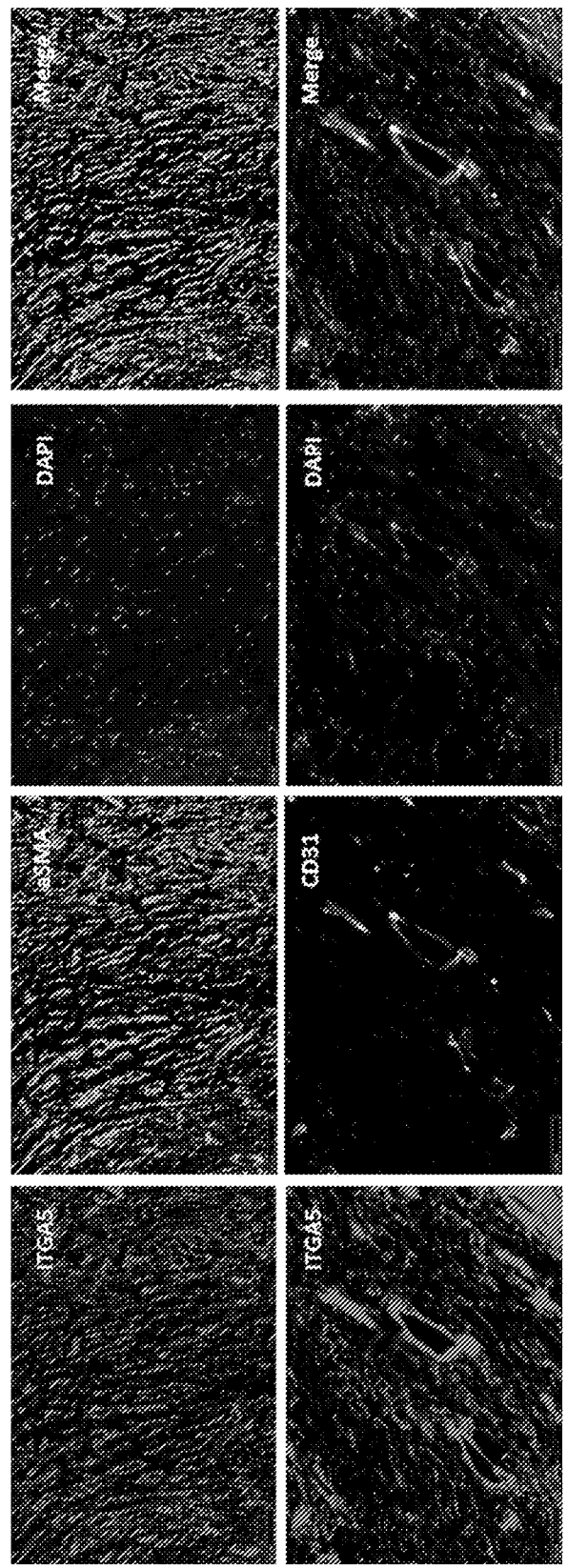

The expression of ITGA5 was examined in normal pancreas and pancreatic tumor. It was found that normal human pancreas showed no staining of ITGA5 while pancreatic tumor showed a strong staining of ITGA5 in stromal region (FIG. 9, Panel A). Co-localization of ITGA5 with α-SMA (marker for myofibroblasts) and CD31 stainings (marker for endothelial cells) revealed that ITGA5 perfectly coincide with α-SMA but slightly with CD31, indicating that ITGA5 is highly expressed on myofibroblasts and also on tumor vasculature (FIG. 9, Panel B).

Example 3

Materials and Methods
Microscale Thermophoresis

Fluorescent labeled peptide (AV3-PEG(6)-5FAM or AXI-I-PEG(6)-FITC) (1 μM) was incubated with different concentrations of a human recombinant receptor (i.e., α5β1, α11β1 or αvβ3) for 10 minutes in Eppendorf tubes. The mixture of peptide and receptor was loaded in to NT.115™ hydrophilic glass capillaries. In order to find the best thermophoretic setting, the binding of peptide to the target receptor was examined at low (20%), middle (40%), and high (80%) MST power and all other binding experiments were performed using the same MST-settings. Finally, the dissociation constant (Kd) value was calculated from an average of three experiments.

Tumor Imaging in Mice

All experiments were conducted under the animal ethical regulation under the Dutch law and protocols were approved by local animal ethical committee. Male SCID mice (approximately 20 g) were obtained from Charles River (Germany). Human pancreatic tumor cells (Panc-1) combined with human pancreatic stellate cells (PSC) were co-injected into the flank of the mice and tumors were allowed to grow to a size of about 200 mm3. AV3 peptide conjugated with 800CW (AV3-800CW) (1 nmol) was injected intravenously alone or with 50-fold excess of unlabeled AV3 (as a blocker) into the tumor-bearing mice. The animals were scanned under anesthesia at 3 hours with Pearl optical imager (LI-COR) to examine the distribution of the peptide.

Effects of AV3 Peptides on Human Dermal Fibroblasts

Human dermal fibroblasts were purchased from ScienCell (Carlsbad, Calif.) and cultured in fibroblasts medium (cat #2301, ScienCell) supplemented with penicillin and streptomycin with 2% FBS. 7×104 cells were seeded in 12-well plates and after 24 hours medium was replaced with FCS-free medium and then human recombinant TGFβ (5 ng/ml) was added without or with different concentration of AV3 (1, 5, 20 μM) and scrambled AV3 (sAV3; 5 and 20 μM) peptides. After 48 hours, the cells were lysed with lysis buffer and western blot analyses was performed for analyzing α-SMA and β-actin expression.

Results
Specificity of Peptides AV3 and AXI-I

Fluorescent labeled peptides (AV3-PEG(6)-5FAM and AXI-I-PEG(6)-FITC) were examined for their binding affinities against α5β1 and α11β1 receptors, respectively using microscale thermophoresis (MST). MST allows peptides to interact with the receptors in solution phase. These peptides were also exposed to an irrelevant receptor of the integrin family αvβ3 and MST analyses were performed.

It was found that AV3 peptide has a dissociation constant (Kd) value of 97.8 nM against α5β1 whereas the Kd value against αvβ3 is 36.1 uM (FIG. 16, Panel A). Similarly the Kd value of AXI-I peptide against α11β1 was 149 nM (FIG. 16, Panel B) while it did not show any binding to αvβ3 (graph not shown). These data indicate that AV3 and AXI-I are highly specific for their respective integrin receptors.

Effects of AV3 Peptides on Human Dermal Fibroblasts

α-SMA, a marker for fibroblasts activation and differentiation, was analyzed after 48 h of the activation with human recombinant TGFβ (5 ng/ml) without or with different concentration of AV3 (1, 5, 20 μM) and scrambled AV3 (sAV3, 5 and 20 μM) peptides.

It was shown that AV3 peptide inhibited fibroblast activation concentration dependently while sAV3 did not show any inhibition (FIG. 17). These results indicate the therapeutic application of AV3 peptide in inhibiting skin scarring.

Tumor Imaging Using AV3 Peptide

The distribution of AV3 peptide labeled with 800CW dye (AV3-800CW) in human pancreatic tumor cells was analyzed. Human pancreatic tumor cells (Panc-1) combined with human pancreatic stellate cells (PSC) were co-injected into the flank of SCID mice and allowed to grow to a size of about 200 mm3. AV3-800CW (1 nmol) was injected intravenously alone (FIG. 18, Panel A) or with (FIG. 18, Panel B) 50-fold excess of unlabeled AV3 in tumor-bearing mice.

Images show that AV3-800CW accumulates into the tumor (arrow in FIG. 18, Panel A) while blocking with excess of AV3 blocks its accumulation in tumor specifically.

The invention claimed is:

1. An isolated or recombinant integrin alpha 5 (ITGA5) binding peptide consisting of 7 to 16 amino acids and comprising the amino acid sequence
   of SEQ ID NO:64, or
   a pharmaceutically acceptable salt thereof.
2. The peptide of claim 1, wherein the peptide has α5β1 integrin and/or ITGA5 inhibiting activity.
3. A dimeric peptide comprising two peptides of claim 1.
4. The dimeric peptide of claim 3, wherein each of the two peptides of the dimeric peptide comprises a cysteine residue.
5. A compound comprising the peptide of claim 1.
6. The compound of claim 5, comprising at least one further moiety.
7. The compound of claim 6, wherein the at least one further moiety comprises a label, a linker, a N-terminal modification, a C-terminal modification and/or an internal modification.
8. The compound of claim 5, wherein the compound comprises the peptide coupled to or encapusulated into a carrier selected from the group consisting of nanoparticles, microparticles, nanocapsules, nanocomplexes, polyplexes, carbon nanotubes, quantum dots, microcapsules, liposomes, microspheres, hydrogels, polymers, micelles, dendrimers, lipid complexes, serum albumin, antibodies, antibody fragments, cyclodextrins and dextran.
9. A nucleic acid molecule comprising a nucleic acid sequence encoding the peptide of claim 1.
10. A pharmaceutical composition comprising:
    the peptide of claim 1, and
    at least one pharmaceutically acceptable carrier, diluent, and/or excipient.
11. A method for the treatment of a subject that has fibrosis or a fibrosis related disorder, an inflammatory disease or cancer, wherein the cancer expresses integrin alpha 5 (ITGA5), the method comprising: administering to the subject a therapeutically effective amount of the peptide of claim 1, or of a compound comprising the peptide.
12. A method of imaging a tissue expressing integrin alpha 5 (ITGA5), the method comprising: contacting the tissue with the peptide of claim 1, wherein the peptide further comprises an imaging label.
13. The method according to claim 12, wherein the tissue expresses α5β1 integrin.
14. A method of treating a subject suffering from fibrosis or a fibrosis related disorder, an inflammatory disease or cancer, wherein the cancer expresses integrin alpha 5 (ITGA5), the method comprising: administering to the subject a therapeutically effective amount of the dimeric peptide of claim 4.
15. The peptide of claim 2, wherein the inhibiting activity comprises inhibition of binding of α5β1 integrin and/or ITGA5 to fibroblasts, stellate cells, myofibroblasts, pericytes and/or other cells of mesenchymal origin.
16. The peptide of claim 1, wherein the ITGA5 binding peptide consists of the amino acid sequence RYYRATY (SEQ ID NO:64).
17. The peptide of claim 1, which is a cyclic or bicyclic peptide.
18. The dimeric peptide of claim 3, which is a cyclic or bicyclic peptide.
19. The method according to claim 11, wherein the peptide consists of the amino acid sequence of SEQ ID NO:64.
20. The method according to claim 14, wherein the peptide consists of the amino acid sequence of SEQ ID NO:64.

* * * * *

SEQUENCE LISTING

```
<160> NUMBER OF SEQ ID NOS: 76

<210> SEQ ID NO 1
<211> LENGTH: 12
<212> TYPE: PRT
<213> ORGANISM: Artificial Sequence
<220> FEATURE:
<223> OTHER INFORMATION: integrin binding peptide

<400> SEQUENCE: 1

Ser Gly Leu Thr Glu Trp Leu Arg Trp Phe Asn Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: integrin binding peptide

<400> SEQUENCE: 2

Ser Phe Ala Thr Trp Thr Pro Asn Phe Glu Arg Asn
1               5                   10

<210> SEQ ID NO 3
<211> LENGTH: 16
<212> TYPE: PRT
<213> ORGANISM: Artificial Sequence
<220> FEATURE:
<223> OTHER INFORMATION: integrin binding peptide

<400> SEQUENCE: 3

Thr Thr Val Arg Tyr Tyr Arg Ile Thr Tyr Gly Glu Thr Gly Gly Asn
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: disclaimed peptide

<400> SEQUENCE: 4

Met Ser Leu Arg Trp Phe Asn Ser Gly Ser Val Arg Pro Ala Thr Thr
1               5                   10                  15

Ile Leu Phe Pro
            20

<210> SEQ ID NO 5
<211> LENGTH: 7
<212> TYPE: PRT
<213> ORGANISM: Artificial Sequence
<220> FEATURE:
<223> OTHER INFORMATION: integrin binding peptide

<400> SEQUENCE: 5

Ser Gly Leu Thr Glu Trp Leu
```

```
1               5

<210> SEQ ID NO 6
<211> LENGTH: 5
<212> TYPE: PRT
<213> ORGANISM: Artificial Sequence
<220> FEATURE:
<223> OTHER INFORMATION: integrin binding peptide

<400> SEQUENCE: 6

Arg Trp Phe Asn Ser
1               5

<210> SEQ ID NO 7
<211> LENGTH: 12
<212> TYPE: PRT
<213> ORGANISM: Artificial Sequence
<220> FEATURE:
<223> OTHER INFORMATION: integrin binding peptide

<400> SEQUENCE: 7

Thr Thr Val Arg Tyr Tyr Arg Ile Thr Tyr Gly Glu
1               5                   10

<210> SEQ ID NO 8
<211> LENGTH: 7
<212> TYPE: PRT
<213> ORGANISM: Artificial Sequence
<220> FEATURE:
<223> OTHER INFORMATION: integrin binding peptide

<400> SEQUENCE: 8

Arg Tyr Tyr Arg Ile Thr Tyr
1               5

<210> SEQ ID NO 9
<211> LENGTH: 16
<212> TYPE: PRT
<213> ORGANISM: Artificial Sequence
<220> FEATURE:
<223> OTHER INFORMATION: integrin binding peptide

<400> SEQUENCE: 9

Thr Thr Val Arg Tyr Tyr Arg Ile Thr Tyr Gly Glu Thr Gly Gly Asn
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: integrin binding peptide

<400> SEQUENCE: 10

Tyr Tyr Arg Ile Thr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: integrin binding peptide

<400> SEQUENCE: 11

Arg Tyr Tyr Arg Ile Thr Tyr Cys
1               5
```

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cagctcgctg gagagatacg                                               20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
ttacaggacg tgttcgcctc                                               20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tccaaaatca agtggggcga                                               20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tgatgaccct tttggctccc                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gaaccctgtg tcctgcatca                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ttggagttcc acctcgaagc                                               20

<210> SEQ ID NO 18
<211> LENGTH: 20
<212> TYPE: DNA
<213> ORGANISM: Artificial Sequence
<220> FEATURE:

<223> OTHER INFORMATION: primer

<400> SEQUENCE: 18
ttgggctact acaaccgcag                                       20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
cttgttggtg ccttccaagc                                       20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
acagtccatg ccatcactgc                                       20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gatccacgac ggacacattg                                       20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
actactgccg agcgtgagat                                       20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ccaatgaaag atggctggaa                                       20

<210> SEQ ID NO 24
<211> LENGTH: 8
<212> TYPE: PRT
<213> ORGANISM: Artificial Sequence
<220> FEATURE:
<223> OTHER INFORMATION: ITGA11 binding peptide

<400> SEQUENCE: 24

Leu Thr Glu Trp Leu Arg Trp Phe
1               5

<210> SEQ ID NO 25
<211> LENGTH: 11
<212> TYPE: PRT
<213> ORGANISM: Artificial Sequence
<220> FEATURE:
<223> OTHER INFORMATION: ITGA11 binding peptide

<400> SEQUENCE: 25

Gly Leu Thr Glu Trp Leu Arg Trp Phe Asn Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: ITGA11 binding peptide

<400> SEQUENCE: 26

Gly Leu Thr Glu Trp Leu Arg Trp Phe Asn
1               5                   10

<210> SEQ ID NO 27
<211> LENGTH: 10
<212> TYPE: PRT
<213> ORGANISM: Artificial Sequence
<220> FEATURE:
<223> OTHER INFORMATION: ITGA11 binding peptide

<400> SEQUENCE: 27

Leu Thr Glu Trp Leu Arg Trp Phe Asn Ser
1               5                   10

<210> SEQ ID NO 28
<211> LENGTH: 11
<212> TYPE: PRT
<213> ORGANISM: Artificial Sequence
<220> FEATURE:
<223> OTHER INFORMATION: ITGA11 binding peptide

<400> SEQUENCE: 28

Ser Gly Leu Thr Glu Trp Leu Arg Trp Phe Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 29

Ser Gly Leu Thr Glu Trp Ala Arg Trp Phe Asn Ser
1               5                   10

<210> SEQ ID NO 30
<211> LENGTH: 10
<212> TYPE: PRT
<213> ORGANISM: Artificial Sequence
<220> FEATURE:
<223> OTHER INFORMATION: ITGA11 binding peptide

<400> SEQUENCE: 30

Ser Gly Leu Thr Glu Trp Leu Arg Trp Phe
1               5                   10

```
<210> SEQ ID NO 31
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 31

Ser Gly Leu Thr Glu Trp Leu Ala Trp Phe Asn Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 32

Ser Gly Leu Thr Glu Trp Leu Arg Trp Phe Asn Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 33

Ser Gly Leu Ala Glu Trp Leu Arg Trp Phe Asn Ser
1               5                   10

<210> SEQ ID NO 34
<211> LENGTH: 7
<212> TYPE: PRT
<213> ORGANISM: Artificial Sequence
<220> FEATURE:
<223> OTHER INFORMATION: ITGA11 binding peptide

<400> SEQUENCE: 34

Trp Leu Arg Trp Phe Asn Ser
1               5

<210> SEQ ID NO 35
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 35

Ser Ala Leu Thr Glu Trp Leu Arg Trp Phe Asn Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 36

Ser Gly Leu Thr Glu Trp Leu Arg Trp Phe Ala Ser
1               5                   10

<210> SEQ ID NO 37
```

```
<211> LENGTH: 6
<212> TYPE: PRT
<213> ORGANISM: Artificial Sequence
<220> FEATURE:
<223> OTHER INFORMATION: ITGA11 binding peptide

<400> SEQUENCE: 37

Thr Glu Trp Leu Arg Trp
1               5

<210> SEQ ID NO 38
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 38

Ser Gly Leu Thr Glu Trp Leu Arg Trp Phe Asn Ser
1               5                   10

<210> SEQ ID NO 39
<211> LENGTH: 8
<212> TYPE: PRT
<213> ORGANISM: Artificial Sequence
<220> FEATURE:
<223> OTHER INFORMATION: ITGA11 binding peptide

<400> SEQUENCE: 39

Glu Trp Leu Arg Trp Phe Asn Ser
1               5

<210> SEQ ID NO 40
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 40

Ser Gly Leu Thr Ala Trp Leu Arg Trp Phe Asn Ser
1               5                   10

<210> SEQ ID NO 41
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 41

Ser Gly Leu Thr Glu Trp Leu Arg Trp Phe Asn Ala
1               5                   10

<210> SEQ ID NO 42
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 42

Ser Gly Leu Thr Glu Ala Leu Arg Trp Phe Asn Ser
1               5                   10

<210> SEQ ID NO 43
<211> LENGTH: 9
```

```
<212> TYPE: PRT
<213> ORGANISM: Artificial Sequence
<220> FEATURE:
<223> OTHER INFORMATION: ITGA11 binding peptide

<400> SEQUENCE: 43

Thr Glu Trp Leu Arg Trp Phe Asn Ser
1               5

<210> SEQ ID NO 44
<211> LENGTH: 9
<212> TYPE: PRT
<213> ORGANISM: Artificial Sequence
<220> FEATURE:
<223> OTHER INFORMATION: ITGA11 binding peptide

<400> SEQUENCE: 44

Ser Gly Leu Thr Glu Trp Leu Arg Trp
1               5

<210> SEQ ID NO 45
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 45

Ser Gly Leu Thr Glu Trp Leu Arg Ala Phe Asn Ser
1               5                   10

<210> SEQ ID NO 46
<211> LENGTH: 12
<212> TYPE: PRT
<213> ORGANISM: Artificial Sequence
<220> FEATURE:
<223> OTHER INFORMATION: ITGA11 binding peptide

<400> SEQUENCE: 46

Ala Gly Leu Thr Glu Trp Leu Arg Trp Phe Asn Ser
1               5                   10

<210> SEQ ID NO 47
<211> LENGTH: 6
<212> TYPE: PRT
<213> ORGANISM: Artificial Sequence
<220> FEATURE:
<223> OTHER INFORMATION: ITGA11 binding peptide

<400> SEQUENCE: 47

Leu Arg Trp Phe Asn Ser
1               5

<210> SEQ ID NO 48
<211> LENGTH: 90
<212> TYPE: PRT
<213> ORGANISM: Homo sapiens

<400> SEQUENCE: 48

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
                20                  25                  30

Arg Ile Arg His His Pro Glu His Phe Ser Gly Arg Pro Arg Glu Asp
            35                  40                  45
```

```
Arg Val Pro His Ser Arg Asn Ser Ile Thr Leu Thr Asn Leu Thr Pro
         50                  55                  60

Gly Thr Glu Tyr Val Val Ser Ile Val Ala Leu Asn Gly Arg Glu Glu
 65                  70                  75                  80

Ser Pro Leu Leu Ile Gly Gln Gln Ser Thr
                 85                  90
```

<210> SEQ ID NO 49
<211> LENGTH: 91
<212> TYPE: PRT
<213> ORGANISM: Mus musculus

<400> SEQUENCE: 49

```
Ala Val Pro Pro Thr Asp Leu Arg Phe Thr Asn Ile Gly Pro Asp
 1               5                  10                  15

Thr Met Arg Val Thr Trp Ala Pro Pro Ser Ile Glu Leu Thr Asn
                 20                  25                  30

Leu Leu Val Arg Tyr Ser Pro Val Lys Asn Glu Glu Asp Val Ala Glu
             35                  40                  45

Leu Ser Ile Ser Pro Ser Asp Asn Ala Val Val Leu Thr Asn Leu Leu
         50                  55                  60

Pro Gly Thr Glu Tyr Leu Val Ser Val Ser Ser Val Tyr Glu Gln His
 65                  70                  75                  80

Glu Ser Ile Pro Leu Arg Gly Arg Gln Lys Thr
                 85                  90
```

<210> SEQ ID NO 50
<211> LENGTH: 63
<212> TYPE: PRT
<213> ORGANISM: Homo sapiens

<400> SEQUENCE: 50

```
Thr Val Arg Tyr Tyr Arg Ile Thr Tyr Gly Glu Thr Gly Gly Asn Ser
 1               5                  10                  15

Pro Val Gln Glu Phe Thr Val Pro Gly Ser Lys Ser Thr Ala Thr Ile
                 20                  25                  30

Ser Gly Leu Lys Pro Gly Val Asp Tyr Thr Ile Thr Val Tyr Ala Val
             35                  40                  45

Thr Gly Arg Gly Asp Ser Pro Ala Ser Ser Lys Pro Ile Ser Ile
         50                  55                  60
```

<210> SEQ ID NO 51
<211> LENGTH: 91
<212> TYPE: PRT
<213> ORGANISM: Mus musculus

<400> SEQUENCE: 51

```
Ala Val Pro Pro Thr Asp Leu Arg Phe Thr Asn Ile Gly Pro Asp
 1               5                  10                  15

Thr Met Arg Val Thr Trp Ala Pro Pro Ser Ile Glu Leu Thr Asn
                 20                  25                  30

Leu Leu Val Arg Tyr Ser Pro Val Lys Asn Glu Glu Asp Val Ala Glu
             35                  40                  45

Leu Ser Ile Ser Pro Ser Asp Asn Ala Val Val Leu Thr Asn Leu Leu
         50                  55                  60

Pro Gly Thr Glu Tyr Leu Val Ser Val Ser Ser Val Tyr Glu Gln His
 65                  70                  75                  80

Glu Ser Ile Pro Leu Arg Gly Arg Gln Lys Thr
                 85                  90
```

<210> SEQ ID NO 52
<211> LENGTH: 63
<212> TYPE: PRT
<213> ORGANISM: Artificial Sequence
<220> FEATURE:
<223> OTHER INFORMATION: Partial Human FNIII-10 seq

<400> SEQUENCE: 52

Thr Val Arg Tyr Tyr Arg Ile Thr Tyr Gly Glu Thr Gly Gly Asn Ser
1               5                   10                  15

Pro Val Gln Glu Phe Thr Val Pro Gly Ser Lys Ser Thr Ala Thr Ile
            20                  25                  30

Ser Gly Leu Lys Pro Gly Val Asp Tyr Thr Ile Thr Val Tyr Ala Val
        35                  40                  45

Thr Gly Arg Gly Asp Ser Pro Ala Ser Ser Lys Pro Ile Ser Ile
    50                  55                  60

<210> SEQ ID NO 53
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 53

Ile Thr Ala Asn Ser Phe Thr Val His Trp Ile Ala
1               5                   10

<210> SEQ ID NO 54
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 54

Val Ala Leu Asn Gly Arg Glu Glu Ser Pro Leu Leu
1               5                   10

<210> SEQ ID NO 55
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 55

Thr Thr Val Arg Tyr Tyr Arg Ile Thr Tyr Gly Glu
1               5                   10

<210> SEQ ID NO 56
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 56

Tyr Tyr Arg Ile Thr Tyr Gly Glu Thr Gly Gly Asn
1               5                   10

<210> SEQ ID NO 57
<211> LENGTH: 12

```
<212> TYPE: PRT
<213> ORGANISM: Artificial Sequence
<220> FEATURE:
<223> OTHER INFORMATION: ITGA5 binding peptide

<400> SEQUENCE: 57

Gly Asp Ser Pro Ala Ser Ser Lys Pro Ile Ser Ile
1               5                   10

<210> SEQ ID NO 58
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 58

Ser Ile Glu Leu Thr Asn Leu Leu Val Arg Tyr Ser
1               5                   10

<210> SEQ ID NO 59
<211> LENGTH: 12
<212> TYPE: PRT
<213> ORGANISM: Artificial Sequence
<220> FEATURE:
<223> OTHER INFORMATION: ITGA5 binding peptide

<400> SEQUENCE: 59

Thr Asn Leu Leu Val Arg Tyr Ser Pro Val Lys Asn
1               5                   10

<210> SEQ ID NO 60
<211> LENGTH: 16
<212> TYPE: PRT
<213> ORGANISM: Artificial Sequence
<220> FEATURE:
<223> OTHER INFORMATION: ITGA5 binding peptide

<400> SEQUENCE: 60

Thr Thr Val Arg Tyr Tyr Arg Ile Thr Tyr Gly Glu Thr Gly Gly Asn
1               5                   10                  15

<210> SEQ ID NO 61
<211> LENGTH: 7
<212> TYPE: PRT
<213> ORGANISM: Artificial Sequence
<220> FEATURE:
<223> OTHER INFORMATION: ITGA5 binding peptide

<400> SEQUENCE: 61

Ala Tyr Tyr Arg Ile Thr Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: ITGA5 binding peptide

<400> SEQUENCE: 62

Arg Ala Tyr Arg Ile Thr Tyr
1               5

<210> SEQ ID NO 63
<211> LENGTH: 7
<212> TYPE: PRT
```

```
<213> ORGANISM: Artificial Sequence
<220> FEATURE:
<223> OTHER INFORMATION: ITGA5 binding peptide

<400> SEQUENCE: 63

Arg Tyr Tyr Ala Ile Thr Tyr
1               5

<210> SEQ ID NO 64
<211> LENGTH: 7
<212> TYPE: PRT
<213> ORGANISM: Artificial Sequence
<220> FEATURE:
<223> OTHER INFORMATION: ITGA5 binding peptide

<400> SEQUENCE: 64

Arg Tyr Tyr Arg Ala Thr Tyr
1               5

<210> SEQ ID NO 65
<211> LENGTH: 7
<212> TYPE: PRT
<213> ORGANISM: Artificial Sequence
<220> FEATURE:
<223> OTHER INFORMATION: ITGA5 binding peptide

<400> SEQUENCE: 65

Arg Tyr Tyr Arg Ile Thr Ala
1               5

<210> SEQ ID NO 66
<211> LENGTH: 8
<212> TYPE: PRT
<213> ORGANISM: Artificial Sequence
<220> FEATURE:
<223> OTHER INFORMATION: ITGA5 binding peptide

<400> SEQUENCE: 66

Arg Tyr Tyr Arg Ile Thr Tyr Cys
1               5

<210> SEQ ID NO 67
<211> LENGTH: 13
<212> TYPE: PRT
<213> ORGANISM: Artificial Sequence
<220> FEATURE:
<223> OTHER INFORMATION: ITGA5 binding peptide

<400> SEQUENCE: 67

Tyr Tyr Arg Ile Thr Tyr Gly Glu Thr Gly Gly Asn Lys
1               5                   10

<210> SEQ ID NO 68
<211> LENGTH: 19
<212> TYPE: PRT
<213> ORGANISM: Artificial Sequence
<220> FEATURE:
<223> OTHER INFORMATION: ITGA5 binding peptide

<400> SEQUENCE: 68

Arg Tyr Tyr Arg Ile Thr Tyr Gly Gly Gly Gly Leu Thr Glu Trp Leu
1               5                   10                  15

Arg Trp Phe

<210> SEQ ID NO 69
<211> LENGTH: 7
```

```
<212> TYPE: PRT
<213> ORGANISM: Artificial Sequence
<220> FEATURE:
<223> OTHER INFORMATION: screened AXI-I variants

<400> SEQUENCE: 69

Ser Gly Leu Thr Glu Trp Leu
1               5

<210> SEQ ID NO 70
<211> LENGTH: 5
<212> TYPE: PRT
<213> ORGANISM: Artificial Sequence
<220> FEATURE:
<223> OTHER INFORMATION: screened AXI-I variants

<400> SEQUENCE: 70

Arg Trp Phe Asn Ser
1               5

<210> SEQ ID NO 71
<211> LENGTH: 12
<212> TYPE: PRT
<213> ORGANISM: Artificial Sequence
<220> FEATURE:
<223> OTHER INFORMATION: screened AXI-I variants

<400> SEQUENCE: 71

Ser Gly Ala Thr Glu Trp Leu Arg Trp Phe Asn Ser
1               5                   10

<210> SEQ ID NO 72
<211> LENGTH: 12
<212> TYPE: PRT
<213> ORGANISM: Artificial Sequence
<220> FEATURE:
<223> OTHER INFORMATION: screened AXI-I variants

<400> SEQUENCE: 72

Ser Gly Ala Thr Glu Trp Leu Arg Trp Ala Asn Ser
1               5                   10

<210> SEQ ID NO 73
<211> LENGTH: 5
<212> TYPE: PRT
<213> ORGANISM: Artificial Sequence
<220> FEATURE:
<223> OTHER INFORMATION: screened AXI-I variants

<400> SEQUENCE: 73

Ser Gly Leu Thr Glu
1               5

<210> SEQ ID NO 74
<211> LENGTH: 8
<212> TYPE: PRT
<213> ORGANISM: Artificial Sequence
<220> FEATURE:
<223> OTHER INFORMATION: screened AXI-I variants

<400> SEQUENCE: 74

Ser Gly Leu Thr Glu Trp Leu Arg
1               5

<210> SEQ ID NO 75
<211> LENGTH: 6
<212> TYPE: PRT
```

```
<213> ORGANISM: Artificial Sequence
<220> FEATURE:
<223> OTHER INFORMATION: screened AXI-I variants

<400> SEQUENCE: 75

Ser Gly Leu Thr Glu Trp
1               5

<210> SEQ ID NO 76
<211> LENGTH: 7
<212> TYPE: PRT
<213> ORGANISM: Artificial Sequence
<220> FEATURE:
<223> OTHER INFORMATION: RYYRITY variant with high unspecific binding

<400> SEQUENCE: 76

Arg Tyr Tyr Arg Ile Ala Tyr
1               5
```